(12) United States Patent
Goebel et al.

(10) Patent No.: US 7,271,184 B2
(45) Date of Patent: Sep. 18, 2007

(54) ACYCLIC AND CYCLIC GUANIDINE- AND ACETAMIDINE DERIVATIVES, THEIR PREPARATION AND THEIR USE AS PESTICIDES, ESP. AS PARASITICIDES

(75) Inventors: Thomas Goebel, Lorrach (DE); Eliane Humbert-Droz, Ponthaux (CH); Maurizio Schwarzenbach, Ramlinsburg (CH)

(73) Assignee: Novartis Animal Health US, Inc., Greensboro, NC (US)

( * ) Notice: Subject to any disclaimer, the term of this patent is extended or adjusted under 35 U.S.C. 154(b) by 659 days.

(21) Appl. No.: 10/779,932

(22) Filed: Feb. 17, 2004

(65) Prior Publication Data

US 2004/0162283 A1 Aug. 19, 2004

Related U.S. Application Data

(60) Division of application No. 10/348,574, filed on Jan. 21, 2003, now Pat. No. 6,759,407, which is a division of application No. 09/850,378, filed on May 7, 2001, now Pat. No. 6,538,013, which is a continuation-in-part of application No. PCT/EP99/08765, filed on Nov. 15, 1999.

(51) Int. Cl.
  *A61K 31/44* (2006.01)
  *A61K 31/425* (2006.01)
  *C07D 277/04* (2006.01)
  *C07D 277/08* (2006.01)
  *C07D 277/20* (2006.01)
  *C07D 275/02* (2006.01)
  *C07D 417/00* (2006.01)
  *C07D 513/00* (2006.01)
  *A01N 43/78* (2006.01)
  *A01N 43/80* (2006.01)

(52) U.S. Cl. .................... 514/357; 548/146; 548/202; 548/206; 548/214; 514/365; 514/372

(58) Field of Classification Search ............... None
See application file for complete search history.

(56) References Cited

U.S. PATENT DOCUMENTS

| 4,742,060 A | 5/1988 | Shiokawa et al. |
| 5,063,236 A | 11/1991 | Gsell |
| 5,302,605 A | 4/1994 | Kristiansen et al. |

FOREIGN PATENT DOCUMENTS

| DE | 42 07 604 A 1 | 3/1992 |
| EP | 0 163 855 A1 | 4/1985 |
| EP | 0 259 738 A2 | 8/1987 |
| EP | 0 285 985 A1 | 3/1988 |
| EP | 0 302 389 A2 | 7/1988 |
| EP | 0 302 389 B1 | 7/1988 |
| EP | 0 529 680 A2 | 7/1988 |
| EP | 0 302 833 A2 | 8/1988 |
| EP | 0 364 844 A1 | 10/1989 |
| EP | 0 375 907 A1 | 11/1989 |
| EP | 0 376 279 A2 | 12/1989 |
| EP | 0 493 369 A1 | 12/1989 |
| EP | 0 381 130 A2 | 1/1990 |
| EP | 0 383 091 A1 | 1/1990 |
| EP | 0 386 565 A1 | 2/1990 |
| EP | 0 471 372 A1 | 8/1991 |
| EP | 0 590 425 A1 | 9/1993 |
| GB | 2 228 003 A | 8/1990 |
| JP | 5-11251 | 5/1993 |
| WO | WO 93/24002 | 12/1993 |
| WO | WO 98/06710 | 2/1998 |

OTHER PUBLICATIONS

Chemical Abstracts, vol. 120, No. 15, Apr. 11, 1994.

*Primary Examiner*—Cecilia J. Tsang
*Assistant Examiner*—Noble Jarrell
(74) *Attorney, Agent, or Firm*—Womble Carlyle Sandridge & Rice, PLLC

(57) ABSTRACT

Novel pesticides of formula (I)

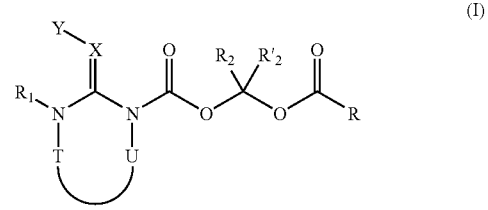

(I)

wherein the substituents, R, $R_1$, $R_2$, $R_2'$, T, U, X and Y are as defined in claim 1, are described. Also described are compositions suitable for use as parasiticides comprising those compounds as active ingredient and to methods of controlling parasites that are based on the administration of those compounds or compositions, and to the use of the said compounds and compositions in a method of controlling parasites and in the manufacture of pesticides for use against parasites. Also described are intermediates of formula (XX)

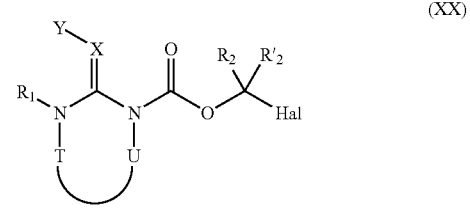

(XX)

wherein
  $R_1$, $R_2$, $R_2'$, T, U, X and Y are as defined in claim 1; and
  Hal is halogen.

The latter also exhibit parasiticidal activity and are suitable for the preparation of the compounds of formula (I).

16 Claims, No Drawings

ACYCLIC AND CYCLIC GUANIDINE- AND ACETAMIDINE DERIVATIVES, THEIR PREPARATION AND THEIR USE AS PESTICIDES, ESP. AS PARASITICIDES

This application is a divisional of U.S. patent application Ser. No. 10/348,574 filed Jan. 21, 2003 and issued Jul. 6, 2004 as U.S. Pat. No. 6,759,407, which is a divisional of U.S. patent application Ser. No. 09/850,378, filed May 7, 2001 and issued Mar. 25, 2003 as U.S. Pat. No. 6,538,013, which is a continuation-in-part of PCT Patent Application No. PCT/EP99/008765, filed Nov. 15, 1999, which applications are herein incorporated by reference.

The present invention relates to novel pesticides of the formula (I) below having improved action against parasites; to compositions suitable for use as parasiticides comprising those compounds as active ingredient and to methods of controlling parasites that are based on the administration of those compounds or compositions, and to the use of the said compounds and compositions in a method of controlling parasites and in the manufacture of pesticides for use against parasites. Also described are intermediates of formula (XX) which themselves have parasiticidal activity and are excellently suitable for the preparation of compounds of formula (I).

Numerous pesticides are known that can be used in controlling parasites on warm-blooded animals. The control is effected principally by two different methods; either by way of contact action by topical and therefore external treatment of the host animal or systemically, that is to say by oral, transdermal or percutaneous administration to the host animal and ingestion of the active ingredient by the parasites via the blood of the host animal.

Far fewer substances are available for systemic use than for topical application, because only substances that have a systemic action and are well tolerated by the host animal can be used.

Compounds having as characteristic structural element the sub-structure of formula (II)

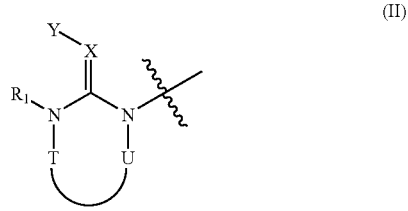

(II)

wherein $R_1$, X, Y, T and U are as defined for formula (I) hereinbelow, form a very interesting class of substances on account of their pronounced topical and systemic action.

A prominent individual example is nitenpyram, a compound of formula (III)

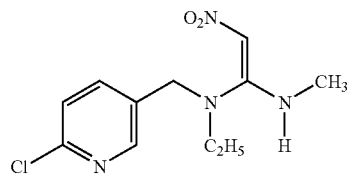

(III)

Nitenpyram and other examples of this class of substances are disclosed, together with their preparation, in EP 0 302 389. Those compounds are described as pesticides having very pronounced insecticidal activity. Further examples of this class of substances are, for example, the subjects of the following patent applications: European published specifications Nos. 285 985, 302 833, 376 279, 471 372, 364 844, 493 369, 381 130, 529 680,163 855, 375 907, 259 738, 386 565, 383 091 and 590 425; U.S. Pat. Nos. 5,063,236, 5,302,605 and 4,742,060; and also DE-4 207 604; GB-2 228 003 and WO 93/24002. Certain substituted 4-nitroiminoperhydro-1.3.5-oxadiazine derivatives and their use as pesticides and intermediates are described in WO 98/06710.

Nitenpyram and other examples of this class of substances that have the said structural element of formula (II) are extremely effective when administered as contact pesticides, for example externally, that is to say topically, to an infested host animal where they come into direct contact with the parasites. They also, however, exhibit a good systemic immediate action when they are administered to the infested host animal orally, parenterally, via injection or via implant.

The action, which is pronounced per se, has a serious disadvantage, however, in that it has been found that while the compounds have a high initial action, their action falls off rapidly only a short time after administration. This can be observed particularly clearly after systemic administration and can be monitored by reference to the bioavailability. Blood level measurements show that in many cases high blood levels are achieved even after a few minutes or, more rarely, after a few hours, but these levels then fall within a few hours, at best within a few days, and therefore fall to below an effective concentration much too rapidly.

In order to eliminate this shortcoming, numerous, but unfortunately unsuccessful, experiments have already been carried out. For example, it has been shown that a prolongation of the systemic action by increasing the dose can be achieved only to a limited extent. If, for example, depots sufficiently large for the active ingredient to be released over several weeks were to be placed under the skin or in the muscles, then the amounts to be injected or implanted would have to be so large that they would no longer be tolerated by the host animal; local irritation, skin eruptions and painful areas develop. This solution, possible per se, therefore fails on practical and, of course, also ethical grounds. Similarly, it has been found that a long-term action is not achievable by an increased oral dose.

When the known compounds having the structural element of formula (II) are administered, it is principally observed that a major part of the substance exhibits its full action only over a short period of time immediately after administration and thereafter the action very rapidly declines. This has serious consequences for preparations for use in veterinary medicine, for example, for tablets, injections or for treatment using the pour-on or spot-on method. Because of the short duration of action it is necessary to repeat treatments at short intervals, which means that the keeper of the animal must either repeat the treatment himself, or have it carried out by a veterinary surgeon, at short intervals. Such an intensive treatment program requires a high degree of discipline, however, and, as experience has shown, after only a short time gives rise to stress on the part of the animal and on the part of the animal's keeper, which not infrequently results in aversion to the treatment and leads to its premature discontinuation.

Prolongation of the action of this inherently extremely effective class of substances has therefore long been a desirable but apparently unattainable goal. The problem underlying the present invention was to achieve that goal and provide substances suitable for use as pesticides having significantly improved properties, especially having a pronounced long-term action.

By the provision of the compounds of formula (I) below it has now, surprisingly, been possible for compounds having the structural element of formula (II) to be modified chemically in such a manner that a high degree of long-term bioavailability after administration is achieved without it being necessary to accept adverse effects as a result.

The new, improved compounds are compounds of formula (I) below

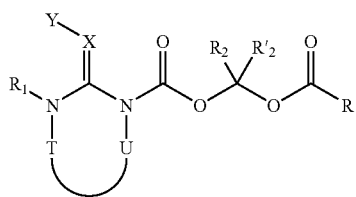

(I)

wherein
- $R_1$ is hydrogen or a radical from the group $C_1$-$C_4$alkyl, formyl, $C_1$-$C_6$alkylcarbonyl, $C_1$-$C_4$alkylsulfonyl, aryl, arylsulfonyl, arylcarbonyl, heterocyclyl and heterocyclyl-substituted $C_1$-$C_6$alkyl, which radical is unsubstituted or mono- or poly-substituted by identical or different substituents; the said substituents being $C_1$-$C_4$alkyl, $C_1$-$C_4$alkoxy, $C_1$-$C_4$alkylthio, $C_1$-$C_4$haloalkyl, halogen, hydroxy, cyano, nitro, amino, $C_1$-$C_4$alkylamino, $C_1$-$C_4$alkyl)$_2$amino, alkoxycarbonyl, $C_1$-$C_4$alkylsulfonyl and arylsulfonyl;
- X is CH or N;
- Y is an electron-withdrawing radical, preferably cyano, nitro or $C_1$-$C_6$haloalkyl-carbonyl, especially CO—$CF_3$;
- T has the meanings of $R_1$ or together with U forms a $C_1$-$C_4$alkylene bridge which is unsubstituted or substituted by a radical $R_1$, or T and U together with the group —N—C—N— form a saturated or unsaturated 5- or 6-membered heterocyclic ring which may in addition contain as further hetero atom O or S or the hetero group —N($C_1$-$C_6$alkyl)-;
- U is hydrogen or $C_1$-$C_6$alkyl, preferably hydrogen, methyl or ethyl;
- $R_2$ is hydrogen or $C_1$-$C_6$alkyl;
- $R_{2'}$ is hydrogen or $C_1$-$C_6$alkyl; and
- R is $C_1$-$C_{20}$alkyl, $C_2$-$C_{20}$alkenyl, $C_2$-$C_6$alkynyl or heterocyclyl, each of those radicals being unsubstituted or substituted by one or more identical or different substituents, the said substituents being selected from the group halogen, cyano, nitro, hydroxy, $C_1$-$C_6$alkoxy, $C_1$-$C_6$alkylthio, $C_1$-$C_6$haloalkyl, $C_1$-$C_6$haloalkoxy and phenyl; or is $C_3$-$C_7$cycloalkyl that is unsubstituted or mono- or poly-substituted by identical or different substituents selected from halogen, cyano, nitro, hydroxy, $C_1$-$C_6$alkyl, $C_2$-$C_6$alkenyl, $C_2$-$C_6$alkynyl, $C_1$-$C_6$alkoxy, $C_1$-$C_6$alkylthio, $C_1$-$C_6$haloalkyl, $C_1$-$C_{20}$haloalkoxy and phenyl;
  - wherein each phenyl moiety is itself unsubstituted or mono- or poly-substituted by identical or different substituents selected from halogen, cyano, nitro, hydroxy, $C_1$-$C_6$alkyl, $C_1$-$C_6$alkoxy, $C_1$-$C_6$alkylthio, $C_1$-$C_6$haloalkyl and $C_1$-$C_{20}$haloalkoxy; or
  - is phenyl phenoxyphenyl each of which is unsubstituted or mono- or poly-substituted by identical or different substituents selected from halogen, cyano, nitro, hydroxy, $C_1$-$C_6$alkyl, $C_1$-$C_6$alkoxy, $C_1$-$C_6$alkylthio, $C_1$-$C_6$haloalkyl and $C_1$-$C_{20}$haloalkoxy.

Within the scope of formula (I) above, preference is given to compounds, wherein R is $C_1$-$C_{20}$alkyl, $C_2$-$C_{20}$alkenyl or $C_2$-$C_6$alkynyl, each of those radicals being unsubstituted or mono- or poly-substituted by identical or different substituents, the said substituents being selected from the group halogen, cyano, nitro, hydroxy, $C_1$-$C_6$alkoxy, $C_1$-$C_6$alkylthio, $C_1$-$C_6$haloalkyl, $C_1$-$C_6$haloalkoxy and phenyl; or is $C_3$-$C_7$cycloalkyl that is unsubstituted or mono- or poly-substituted by identical or different substituents selected from halogen, cyano, nitro, hydroxy, $C_1$-$C_6$alkyl, $C_2$-$C_6$alkenyl, $C_2$-$C_6$alkynyl, $C_1$-$C_6$alkoxy, $C_1$-$C_6$alkylthio, $C_1$-$C_6$haloalkyl, $C_1$-$C_{20}$haloalkoxy and phenyl; or is phenyl phenoxyphenyl each of which is unsubstituted or mono- or poly-substituted by identical or different substituents selected from halogen, cyano, nitro, hydroxy, $C_1$-$C_6$alkyl, $C_1$-$C_6$alkoxy, $C_1$-$C_6$alkylthio, $C_1$-$C_6$haloalkyl, $C_1$-$C_{20}$haloalkoxy.

Within the group of compounds of formula (I) wherein R is $C_3$-$C_7$cycloalkyl that is mono- or poly-substituted by identical or different substituents selected from halogen, cyano, nitro, hydroxy, $C_1$-$C_6$alkyl, $C_2$-$C_6$alkenyl, $C_2$-$C_6$alkynyl, $C_1$-$C_6$alkoxy, $C_1$-$C_6$alkylthio, $C_1$-$C_6$haloalkyl, $C_1$-$C_{20}$haloalkoxy and phenyl; wherein the phenyl moiety is itself unsubstituted or mono- or poly-substituted by identical or different substituents selected from halogen, cyano, nitro, hydroxy, $C_1$-$C_6$alkyl, $C_1$-$C_6$alkoxy, $C_1$-$C_6$alkylthio, $C_1$-$C_6$haloalkyl and $C_1$-$C_{20}$haloalkoxy, special preference on account of their pronounced activity is given to those compounds in which the $C_3$-$C_7$cycloalkyl radical is substituted by one substituent and in the 1-position.

By the introduction of the side chain of formula (IV)

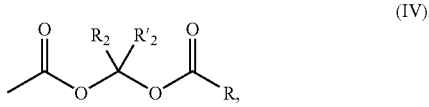

wherein $R_2$, $R_2$ and R are as defined for formula (I), it has now been possible to prepare substances that exhibit simultaneously a number of long sought and very desirable properties and are now actually suitable for practical use:
1. The compounds of formula (I) have a high level of activity against arthropods, especially blood-sucking insects.
2. They exhibit excellent tolerability when administered systemically and topically to a host animal.
3. They are distinguished by an appreciably longer duration of action in comparison with known compounds having the structural element of formula (II), which can readily be demonstrated by reference to the mortality of the parasites on the host animal.
4. They can be handled satisfactorily from the standpoint of formulation technology and have adequate storage stability.

It was not to be predicted that the chemical modification carried out here would result in these advantageous properties and would be able to impart to the novel compounds of formula (I) these positive long-term properties.

In the context of the present invention, the definitions of the substituents are to be understood as follows: each of the substituents indicated under formula (I) that can itself be poly-substituted is substituted by either identical or different substituents, that is to say multiple substitutions are to be interpreted as meaning that identical or different substituents can be present simultaneously on the same radical. For example, a radical poly-substituted by halogen may have either several identical halogen atoms or several different halogen atoms. Multiple substitutions are to be interpreted accordingly for other radicals.

The alkyl groups appearing in the definitions of substituents in terms, such as alkyl, alkylcarbonyl, alkylsulfonyl, alkoxy, alkylthio, haloalkyl, alkylamino, dialkylamino, haloalkylcarbonyl, etc. may, according to the number of carbon atoms, be straight-chain or branched and are, e.g., methyl, ethyl, propyl, butyl, pentyl, hexyl, heptyl, octyl, nonyl, decyl, undecyl, dodecyl, tetradecyl, hexadecyl, octadecyl or eicosyl; and the branched isomers thereof, e.g., isopropyl, isobutyl, sec-butyl, tert-butyl, isopentyl, neopentyl or isohexyl. Alkoxy, haloalkyl, haloalkylcarbonyl and haloalkoxy radicals are derived from the mentioned alkyl groups and accordingly are partially or fully halogenated radicals; poly-halogenated radicals carry identical or different halogen atoms.

The terms halo and halogen denote halogen atoms and generally denote fluorine, chlorine, bromine or iodine, here preferably fluorine or chlorine, as substituent of an alkyl group especially fluorine and as substituent of a heterocycle especially chlorine.

Examples of haloalkyl—as a group per se and as a structural element of other groups and compounds, such as haloalkoxy—are methyl mono- to tri-substituted by fluorine, chlorine and/or bromine, such as $CHF_2$ or $CF_3$; ethyl mono- to penta-substituted by fluorine, chlorine and/or bromine, such as $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CHBrF$ or $CClFCHClF$; propyl or isopropyl mono- to hepta-substituted by fluorine, chlorine and/or bromine, such as $CH_2CHBrCH_2Br$, $CF_2CHFCF_3$, $CH_2CF_2CF_3$ or $CH(CF_3)_2$; and butyl mono- to nona-substituted by fluorine, chlorine and/or bromine, or one of its isomers, such as $CF(CF_3)CHFCF_3$ or $CH_2(CF_2)_2CF_3$.

In the context of the present invention, Het and heterocyclyl are to be understood as meaning aliphatic or aromatic cyclic radicals that contain at least one oxygen, sulfur or nitrogen atom. Five- and six-membered heterocycles are preferred. Heterocyclyl accordingly typically includes substituents such as dioxolanyl, pyrrolidinyl, piperidinyl, morpholinyl, pyridyl, pyrrolyl, furyl, thienyl, imidazolyl, tetrahydrofuryl, tetrahydropyranyl, dihydrofuryl, dihydropyranyl, isoxazolyl, oxazolyl, thiazolyl, oxazolinyl, oxazolidinyl, imidazolinyl, imidazolidinyl and dioxanyl. Special preference is given to those which are unsubstituted or contain one or two halogen atoms, halogen here being fluorine, chlorine or bromine, but especially chlorine. Of those heterocyclic radicals special mention should be made of pyridyl, thiazolyl and tetrahydrofuryl. More especially preferred sub-groups of formula (I) contain as heterocyclyl radicals 5,6-dichloro-pyridin-3-yl, 6-chloro-pyridin-3-yl, 2-chlorothiazol-5-yl and tetrahydrofuran-3-yl.

Aryl by itself or as part of a substituent, e.g., arylsulfonyl, arylcarbonyl or aralkyl, is phenyl or naphthyl, preferably phenyl.

Alkenyl is, in each case giving due consideration to the number of carbon atoms contained in the group in question, either straight-chain, e.g., vinyl, 1-methylvinyl, allyl, 1-butenyl or 2-hexenyl; or branched, e.g., isopropenyl. Alkynyl is, in each case giving due consideration to the number of carbon atoms contained in the group in question, either straight-chain, e.g., propargyl, 2-butynyl or 5-hexynyl, or branched, e.g., 2-ethynylpropyl or 2-propargylisopropyl. $C_3$-$C_7$Cycloalkyl is cyclopropyl, cyclobutyl, cyclopentyl, cyclohexyl or cycloheptyl.

Typical $C_1$-$C_4$alkylene bridges are —$CH_2$—, —$CH_2$—$CH_2$—, —$CH_2$—$CH_2$—$CH_2$—, —$CH_2$—$CH_2$—$CH_2$—$CH_2$—, —$CH(CH_3)$—$CH_2$—, —$CH(C_2H_5)$—$CH_2$—, —$CH_2$—$CH(CH_3)$—$CH_2$—, —$CH(CH_3)$—$CH(CH_3)$—, —$C(CH_3)_2$—, —$C(CH_3)(C_2H_5)$— and —$C(C_2H_5)_2$—.

Compounds of formula (I) having at least one basic centre may form acid addition salts with strong acids. Physiologically tolerable acid addition salts are of special interest.

An interesting sub-group within the compounds according to the invention is formed by compounds of formula (I) wherein Y is $NO_2$;

$R_1$ is hydrogen or a radical from the group $C_1$-$C_4$alkyl, formyl, $C_1$-$C_6$alkylcarbonyl, $C_1$-$C_4$alkylsulfonyl, aryl, arylsulfonyl, arylcarbonyl, heterocyclyl and heterocyclyl-substituted $C_1$-$C_6$alkyl, which radical is unsubstituted or mono- or poly-substituted by identical or different substituents; the said substituents being $C_1$-$C_4$alkyl, $C_1$-$C_4$alkoxy, $C_1$-$C_4$alkylthio, $C_1$-$C_4$haloalkyl, halogen, hydroxy, cyano, nitro, amino, $C_1$-$C_4$alkylamino, $C_1$-$C_4$alkyl$_2$amino, alkoxycarbonyl, $C_1$-$C_4$alkylsulfonyl and arylsulfonyl;

T has the meanings of $R_1$ or together with U forms a $C_1$-$C_4$alkylene bridge which is unsubstituted or substituted by a radical $R_1$, or T and U together with the group —N—C—N— form a saturated or unsaturated 5- or 6-membered heterocyclic ring which may in addition contain as further hetero atom O or S or the hetero group —N($C_1$-$C_6$alkyl)-;

U is hydrogen or $C_1$-$C_6$alkyl, preferably hydrogen, methyl or ethyl; and $R_2$, $R_{2'}$ and R are as defined for formula (I).

Another interesting group is formed by compounds of formula (I) wherein $R_1$ is —CH$_2$-Het;
X is CH;
Y is NO$_2$;

Het is heterocyclyl that is unsubstituted or mono- or poly-substituted by identical or different substituents; the substituents being $C_1$-$C_4$alkyl, $C_1$-$C_4$alkoxy, $C_1$-$C_4$alkylthio, $C_1$-$C_4$haloalkyl, halogen, hydroxy, cyano, nitro, amino, $C_1$-$C_4$alkylamino, $C_1$-$C_4$alkyl$_2$amino, alkoxycarbonyl, $C_1$-$C_4$alkylsulfonyl and arylsulfonyl;

T (1) is a radical from the group formyl, $C_1$-$C_6$alkylcarbonyl, $C_1$-$C_4$alkylsulfonyl, aryl, arylsulfonyl, arylcarbonyl, heterocyclyl and heterocyclyl-substituted $C_1$-$C_6$alkyl, which radical is unsubstituted or mono- or poly-substituted by identical or different substituents; the said substituents being $C_1$-$C_4$alkyl, $C_1$-$C_4$alkoxy, $C_1$-$C_4$haloalkyl, halogen, hydroxy, cyano, nitro, amino, $C_1$-$C_4$alkylamino, $C_1$-$C_4$alkyl$_2$amino, $C_1$-$C_4$alkylsulfonyl and arylsulfonyl; or (2) T together with U forms a $C_1$-$C_4$alkylene bridge which is unsubstituted or substituted by a radical selected from the group $C_1$-$C_4$alkyl, formyl, $C_1$-$C_6$alkylcarbonyl, $C_1$-$C_4$alkylsulfonyl, aryl, arylsulfonyl, arylcarbonyl, heterocyclyl and heterocyclyl-substituted $C_1$-$C_6$alkyl; each radical from the said group itself being unsubstituted or substituted by $C_1$-$C_4$alkyl, $C_1$-$C_4$alkoxy, $C_1$-$C_4$haloalkyl, halogen, hydroxy, cyano, nitro, amino, $C_1$-$C_4$alkylamino, $C_1$-$C_4$alkyl$_2$amino, $C_1$-$C_4$alkylsulfonyl or arylsulfonyl; or (3) T and U together with the group —N—C—N— form a saturated or unsaturated 5- or 6-membered heterocyclic ring which may in addition contain as further hetero atom O or S or the hetero group —N($C_1$-$C_6$alkyl)-;

U is hydrogen or $C_1$-$C_6$alkyl, preferably hydrogen, methyl or ethyl; and $R_2$, $R_{2'}$ and R are as defined for formula (I).

Very especially preferred within the scope of formula (I), however, are compounds of formula (X)

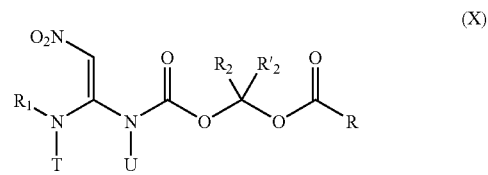

(X)

wherein
$R_1$ is —CH$_2$-Het;
R is $C_1$-$C_{20}$alkyl, $C_2$-$C_{20}$alkenyl or $C_2$-$C_6$alkynyl, each of those radicals being unsubstituted or mono- or poly-substituted by identical or different substituents, the said substituents being selected from the group halogen, cyano, nitro, hydroxy, $C_1$-$C_6$alkoxy, $C_1$-$C_6$alkylthio, $C_1$-$C_6$haloalkyl, $C_1$-$C_6$haloalkoxy and phenyl; or is $C_3$-$C_7$cycloalkyl that is unsubstituted or mono- or poly-substituted by identical or different substituents selected from halogen, cyano, nitro, hydroxy, $C_1$-$C_6$alkyl, $C_2$-$C_6$alkenyl, $C_2$-$C_6$alkynyl, $C_1$-$C_6$alkoxy, $C_1$-$C_6$alkylthio, $C_1$-$C_6$haloalkyl, $C_1$-$C_{20}$haloalkoxy and phenyl; or is phenyl phenoxyphenyl each of which is unsubstituted or mono- or poly-substituted by identical or different substituents selected from halogen, cyano, nitro, hydroxy, $C_1$-$C_6$alkyl, $C_1$-$C_6$alkoxy, $C_1$-$C_6$alkylthio, $C_1$-$C_6$haloalkyl, $C_1$-$C_{20}$haloalkoxy;

T and U are each independently of the other hydrogen or $C_1$-$C_6$alkyl, preferably hydrogen, methyl or ethyl;
$R_2$ is hydrogen or $C_1$-$C_6$alkyl;
$R_{2'}$ is hydrogen or $C_1$-$C_6$alkyl; and
Het is heterocyclyl that is unsubstituted or mono- or poly-substituted by identical or different halogen atoms.

A further especially preferred sub-group of compounds of formula (I) is formed, on account of their pronounced activity, by compounds of formula (XI)

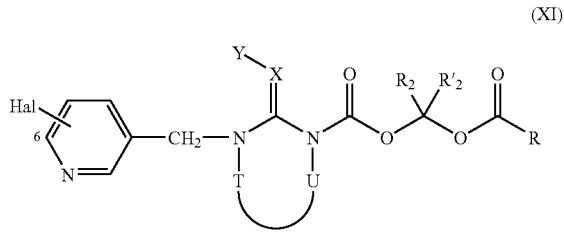

(XI)

wherein
Hal is halogen, preferably fluorine, chlorine or bromine and especially chlorine; and especially occupies the 6-position in the pyridine;
X is CH or N and especially N;
Y is an electron-withdrawing radical, preferably cyano, nitro or $C_1$-$C_6$haloalkyl-carbonyl, especially CO—CF$_3$; more especially nitro;
T together with U forms a $C_1$-$C_4$alkylene bridge, preferably an ethylene bridge, which is preferably unsubstituted or substituted by methyl or ethyl; and
$R_2$, $R_{2'}$ and R are as defined for formula (I).

Equally preferred on account of their pronounced activity is a sub-group of compounds of formula (I) having the following formula (XII)

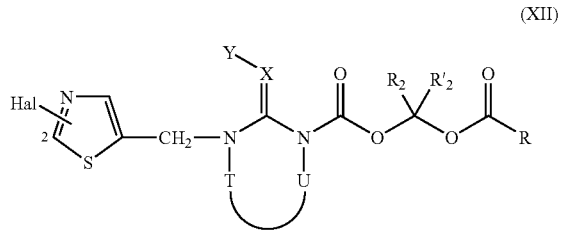

wherein
Hal is halogen, preferably fluorine, chlorine or bromine and especially chlorine; and especially occupies the 2-position in the thiazole;
X is CH or N and especially N;
Y is an electron-withdrawing radical, preferably cyano, nitro or $C_1$-$C_6$haloalkyl-carbonyl, especially CO—$CF_3$; more especially nitro;
T together with U forms one of the groups —$CH_2$—$CH_2$—, —$CH_2$—$CH_2$—$CH_2$—, —$CH_2$—O—$CH_2$— and —$CH_2$—N($CH_3$)—$CH_2$—, wherein all methylene groups are unsubstituted or one of said methylen groups is substituted by methyl or ethyl; and
$R_2$, $R_{2'}$ and R are as defined in claim 1 for formula (I).

A preferred sub-group of compounds within the scope of formula (X) is formed by those compounds, wherein U is methyl or ethyl.

A further preferred group of compounds within the scope of formula (X) is formed by those compounds, wherein T is methyl or ethyl.

A further preferred sub-group of compounds within the scope of formula (X) is formed by those compounds, wherein $R_2$ and $R_{2'}$ are hydrogen, methyl or ethyl.

Especially preferred among the compounds within the scope of formula (X) and within the scope of preferred sub-groups mentioned above are those compounds in which the radical Het is pyridyl, thiazolyl or tetrahydrofuryl that is unsubstituted or mono- or di-substituted by halogen; especially 5,6-dichloro-pyridin-3-yl, 6-chloro-pyridin-3-yl, 2-chlorothiazol-5-yl and tetrahydrofuran-3-yl.

Within the scope of mentioned sub-groups, preference is given to compounds of formula (I), wherein R is $C_1$-$C_{20}$alkyl, $C_2$-$C_{20}$alkenyl or $C_2$-$C_6$alkynyl and especially straight-chain or branched $C_6$-$C_{20}$alkyl.

Especially preferred on account of its biological activity is any compound selected from the group of compounds 1.001; 1.008; 1.011; 1.012; 1.013; 1.014; 1.015; 1.018; 1.019; 1.020; 1.021; 1.022; 1.054; 1.055; 1.056; 1.057; 1.058; 1.059; 1.060; 1.061; 1.062; 1.063; 1.064; 1.065; 1.066; 1.067; 1.068; 1.069; 1.070; 1.071; 1.072; 1.073; 1.074; 1.075; 1.076; 1.077; 1.078; 1.079; 1.080; 1.081; 1.082; 1.083; 1.084; 1.085; 1.086 and 1.087.

Parasites in the context of the present invention are parasitic arthropods and, of those, especially blood-sucking insects. Insects of the following orders are included: Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera.

Special mention should also be made, however, of pests that trouble human beings or animals and transmit pathogens, e.g., flies, such as *Musca domestica, Musca vetustissima, Musca autumnalis, Fannia canicularis, Sarcophaga carnaria, Lucilia sericata, Lucilia cuprina, Hypoderma bovis, Hypoderma lineatum, Chrysomyia chloropyga, Dermatobia hominis, Cochliomyia hominivorax, Gasterophilus intestinalis, Oestrus ovis, Callipora erythrocephala* (=blowfly), *Haematobia* (=hornfly) and mosquitos, and also blood-sucking pests, e.g., fleas, such as *Ctenocephalides felis* and *Ctenocephalides canis* (cat and dog fleas), *Xenopsylla cheopis, Pulex irritans, Dermatophilus penetrans*, lice, such as *Damalina ovis, Pediculus humanis*, stable flies and horse-flies, such as *Stomoxys calcitrans, Haematopota pluvialis, Tabanus nigrovittatus, Chrysops caecutiens*, tabanids, tsetse flies, such as Glossinia species, and biting insects, more especially cockroaches, such as *Blatella germanic* or *Blatta orientalis* and *Periplaneta americana*. The said parasites attack warm-blooded animals, including farm animals, such as cows, pigs, sheep and goats; poultry, such as hens, turkeys and geese; animals bred for their fur, such as mink, foxes, chinchillas, rabbits and the like; as well as domestic animals and pets, such as cats and dogs, and even human beings do not escape attack.

Likewise, flea infestation in domestic animals and pets is a problem for the animal owner to which as yet only unsatisfactory solutions have been found. Owing to the complicated life cycle of the flea, none of the known methods of controlling fleas is totally satisfactory, especially since most of the known methods are aimed principally at controlling the fully grown fleas in the animal's coat and take no account at all of the various juvenile stages of the fleas, which live not only in the animal's coat but also on the floor, on carpets, on the animal's sleeping place, on chairs, in the garden and in all the other places with which the infested animal comes into contact. Flea treatment is generally expensive and must be continued for a prolonged period, success generally only being achieved when the treatment is applied not only to the infested animal, e.g., the dog or cat, but also simultaneously to any places frequented by the infested animal.

The compounds of formula (I) according to the invention can be used alone or in combination with other biocides. For example, in order to increase the effect they can be combined with pesticides having the same direction of action or in order to broaden the spectrum of action they can be combined with substances having a different direction of action. It may also be of advantage to add repelling substances, so-called repellents. Where it is desired to extend the spectrum of action to endoparasites, e.g., worms, the compounds of formula (I) are advantageously combined with substances having endoparasiticidal properties. They can, of course, also be used in combination with anti-bacterial agents. Since the compounds of formula (I) are "adulticides", that is to say since they are effective especially against the fully grown stages of the target parasites, the addition of pesticides that are effective rather against the juvenile stages of the parasite may be very advantageous, since in that way the majority of parasites causing large-scale economic damage will be covered. Furthermore, a substantial contribution is made to avoiding the development of resistance. Some combinations may also lead to synergistic effects, that is to say the total amount of active ingredient applied can be reduced, which is desirable from the ecological standpoint. Preferred groups of combination partners and especially preferred combination partners are given below, it being possible for the combinations to comprise one or more of these partners in addition to a compound of formula (I).

Suitable mixing partners include biocides, e.g., the insecticides and acaricides listed below, which have various mechanisms of action and are well-known to the person skilled in the art, e.g., chitin synthesis inhibitors and growth regulators; active ingredients that act in the same way as juvenile hormones; active ingredients that act as adulticides; broad spectrum insecticides; broad spectrum acaricides and nematicides; and also the well-known anthelmintics and substances that repel insects and/or acarina, the aforementioned repellents or detachers.

Non-limiting examples of suitable insecticides and acaricides are:

(I) aldicarb;
(II) azinphos-methyl;
(III) benfuracarb;
(IV) bifenthrin;
(V) buprofezin;
(VI) carbofuran;
(VII) dibutylaminothio;
(VIII) cartap;
(IX) chlorfluazuron;
(X) chlorpyrifos;
(XI) cyfluthrin;
(XII) lambda-cyhalothrin;
(XIII) alpha-cypermethrin;
(XIV) zeta-cypermethrin;
(XV) deltamethrin;
(XVI) diflubenzuron;
(XVII) endosulfan;
(XVIII) ethiofencarb;
(XIX) fenitrothion;
(XX) fenobucarb;
(XXI) fenvalerate;
(XXII) formothion;
(XXIII) methiocarb;
(XXIV) heptenophos;
(XXV) imidacloprid;
(XXVI) isoprocarb;
(XXVII) methamidophos;
(XXVIII) methomyl;
(XXIX) mevinphos;
(XXX) parathion;
(XXXI) parathion-methyl;
(XXXII) phosalone;
(XXXIII) pirimicarb;
(XXXIV) propoxur;
(XXXV) teflubenzuron;
(XXXVI) terbufos;
(XXXVII) triazamate;
(XXXVIII) abamectin;
(XXXIX) fenobucarb;
(XL) tebufenozide;
(XLI) fipronil;
(XLII) beta-cyfluthrin;
(XLIII) silafluofen;
(XLIV) fenpyroximate;
(XLV) pyridaben;
(XLVI) fenazaquin;
(XLVII) pyriproxyfen;
(XLVIII) pyrimidifen;
(XLIX) nitenpyram;
(L) NI-25, acetamiprid;
(LI) avermectin $B_1$;
(LII) an insect-active extract from a plant;
(LIII) a preparation containing insect-active nematodes;
(LIV) a preparation obtainable from *Bacillus subtilis*;
(LV) a preparation containing insect-active fungi;
(LVI) a preparation containing insect-active viruses;
(LVII) AC 303 630;
(LVIII) acephat;
(LIX) acrinathrin;
(LX) alanycarb;
(LXI) alphamethrin;
(LXII) amitraz;
(LXIII) AZ 60541;
(LXIV) azinphos A;
(LXV) azinphos M;
(LXVI) azocyclotin;
(LXVII) bendiocarb;
(LXVIII) bensultap;
(LXIX) beta-cyfluthrin;
(LXX) BPMC;
(LXXI) brofenprox;
(LXXII) bromophos A;
(LXXIII) bufencarb;
(LXXIV) butocarboxime;
(LXXV) butylpyridaben;
(LXXVI) cadusafos;
(LXXVII) carbaryl;
(LXXVIII) carbophenothion;
(LXXIX) chloethocarb;
(LXXX) chlorethoxyfos;
(LXXXI) chlormephos;
(LXXXII) cis-Res-methrin;
(LXXXIII) clocythrin;
(LXXXIV) clofentezin;
(LXXXV) cyanophos;
(LXXXVI) cycloprothrin;
(LXXXVII) cyhexatin;
(LXXXVIII) demeton M;
(LXXXIX) demeton S;
(XC) demeton-S-methyl;
(XCI) dichlofenthion;
(XCII) dicliphos;
(XCIII) diethion;
(XCIV) dimethoat;
(XCV) dimethylvinphos;
(XCVI) dioxathion;
(XCVII) edifenphos;
(XCVIII) emamectin;
(XCIX) esfenvalerat;
(C) ethion;
(CI) ethofenprox;
(CII) ethoprophos;
(CIII) etrimphos;
(CIV) fenamiphos;
(CV) fenbutatinoxid;
(CVI) fenothiocarb;
(CVII) fenpropathrin;
(CVIII) fenpyrad;
(CIX) fenthion;
(CX) fluazinam;
(CXI) flucycloxuron;
(CXII) flucythrinat;
(CXIII) flufenoxuron;
(CXIV) flufenprox;
(CXV) fonophos;
(CXVI) fosthiazat;
(CXVII) fubfenprox;
(CXVIII) HCH;
(CXIX) hexaflumuron;
(CXX) hexythiazox;
(CXXI) iprobenfos;
(CXXII) isofenphos;
(CXXIII) isoxathion;
(CXXIV) ivermectin;
(CXXV) lambda-cyhalothrin;
(CXXVI) malathion;
(CXXVII) mecarbam;
(CXXVIII) mesulfenphos;
(CXXIX) metaldehyd;
(CXXX) metolcarb;

-continued (CXXXI) milbemectin;
(CXXXII) moxidectin;
(CXXXIII) naled;
(CXXXIV) NC 184;
(CXXXV) omethoat;
(CXXXVI) oxamyl;
(CXXXVII) oxydemethon M;
(CXXXVIII) oxydeprofos;
(CXXXIX) permethrin;
(CXL) phenthoat;
(CXLI) phorat;
(CXLII) phosmet;
(CXLIII) phoxim;
(CXLIV) pirimiphos M;
(CXLV) pirimiphos A;
(CXLVI) promecarb;
(CXLVII) propaphos;
(CXLVIII) prothiofos;
(CXLIX) prothoat;
(CL) pyrachlophos;
(CLI) pyrada-phenthion;
(CLII) pyresmethrin;
(CLIII) pyrethrum;
(CLIV) RH 5992;
(CLV) salithion;
(CLVI) sebufos;
(CLVII) sulfotep;
(CLVIII) sulprofos;
(CLIX) tebufenpyrad;
(CLX) tebupirimphos;
(CLXI) tefluthrin;
(CLXII) temephos;
(CLXIII) terbam;
(CLXIV) tetrachlor-vinphos;
(CLXV) thiafenox;
(CLXVI) thiodicarb;
(CLXVII) thiofanox;
(CLXVIII) thionazin;
(CLXIX) thuringiensin;
(CLXX) tralomethrin;
(CLXXI) triarthen;
(CLXXII) triazophos;
(CLXXIII) triazuron;
(CLXXIV) trichlorfon;
(CLXXV) triflumuron;
(CLXXVI) trimethacarb;
(CLXXVII) vamidothion;
(CLXXVIII) xylylcarb;
(CLXXIX) YI 5301/5302;
(CLXXX) zetamethrin;
(CLXXXI) DPX-MP062;
(CLXXXII) RH-2485;
(CLXXXIII) D 2341;
(CLXXXIV) XMC (3,5-xylylmethylcarbamate),
(CLXXXV) lufenuron
(CLXXXVI) fluazuron
(CLXXXVII) methoprene
(CLXXXVIII) hydroprene
(CLXXXIX) fenoxycarb
(CXC) chlorfenapyr or
(CXCI) spinosad Non-limiting examples of suitable anthelmintics are mentioned below, some examples, in addition to having the anthelmintic activity, also having an insecticidal and acaricidal activity and, in some cases, being already contained in the list above:

(A1) praziguantel=2-cyclohexylcarbonyl-4-oxo-1,2,3,6,7,11b-hexahydro-4H-pyrazino[2,1-α]isoquinoline
(A2) closantel=3,5-diiodo-N-[5-chloro-2-methyl-4-(a-cyano-4-chlorobenzyl)phenyl]salicylamide
(A3) triclabendazole=5-chloro-6-(2,3-dichlorophenoxy)-2-methylthio-1H-benzimidazole
(A4) levamisol=L-(−)-2,3,5,6-tetrahydro-6-phenylimidazo[2,1b]thiazole
(A5) mebendazole=(5-benzoyl-1H-benzimidazol-2-yl)carbamic acid methyl ester
(A6) omphalotin=a macrocyclic fermentation product of the fungus *Omphalotus olearius* described in WO 97/20857
(A7) abamectin=avermectin B1
(A8) ivermectin=22,23-dihydroavermectin B1
(A9) moxidectin=5-O-demethyl-28-deoxy-25-(1,3-dimethyl-1-butenyl)-6,28-epoxy-23-(methoxyimino)-milbemycin B
(A10) doramectin=25-cyclohexyl-5-O-demethyl-25-de(1-methylpropyl)-avermectin A1a
(A11) milbemectin=mixture of milbemycin A3 and milbemycin A4
(A12) milbemycinoxim=5-oxime of milbemectin Non-limiting examples of suitable repelling substances (repellents or detachers) are:

(R1) DEET (N,N-diethyl-m-toluamide)
(R2) KBR 3023 N-butyl-2-oxycarbonyl-(2-hydroxy)-piperidine
(R3) cymiazole=N-2,3-dihydro-3-methyl-1,3-thiazol-2-ylidene-2,4-xylidene The said mixing partners are well-known to experts in the field. Most of them are described in the various editions of the *Pesticide Manual*, The British Crop Protection Council, London, and others are described in the various editions of *The Merck Index*, Merck & Co., Inc., Rahway, N.J., USA or in the patent literature. The following list therefore confines itself to giving some examples of sources.

(I) 2-methyl-2-(methylthio)propionaldehyde-O-methylcarbamoyloxime(aldicarb), from *The Pesticide Manual*, $11^{th}$ ed. (1997), The British Crop Protection Council, London, page 26;
(II) S-(3,4-dihydro-4-oxobenzo[d]-[1,2,3]-triazin-3-ylmethyl)O,O-dimethyl-phosphorodithioate(azinphos-methyl), from *The Pesticide Manual*, $11^{th}$ ed. (1997), The British Crop Protection Council, London, page 67;
(III) ethyl-N-[2,3-dihydro-2,2-dimethylbenzofuran-7-yloxycarbonyl-(methyl)aminothio]-N-isopropyl-β-alaninate(benfuracarb), from *The Pesticide Manual*, $11^{th}$ ed. (1997), The British Crop Protection Council, London, page 96;
(IV) 2-methylbiphenyl-3-ylmethyl-(Z)-(1RS)-cis-3-(2-chloro-3,3,3-trifluoroprop-1-enyl)-2,2-dimethylcyclopropanecarboxylate(bifenthrin), from *The Pesticide Manual*, $11^{th}$ ed. (1997), The British Crop Protection Council, London, page 118;
(V) 2-tert-butylimino-3-isopropyl-5-phenyl-1,3,5-thiadiazian-4-one(buprofezin), from *The Pesticide Manual*, $11^{th}$ ed. (1997), The British Crop Protection Council, London, page 157;
(VI) 2,3-dihydro-2,2-dimethylbenzofuran-7-yl-methylcarbamate(carbofuran), from *The Pesticide Manual*, $11^{th}$ ed. (1997), The British Crop Protection Council, London, page 186;
(VII) 2,3-dihydro-2,2-dimethylbenzofuran-7-yl-(dibutylaminothio)methylcarbamate(carbosulfan), from *The Pesticide Manual*, $11^{th}$ ed. (1997), The British Crop Protection Council, London, page 188;
(VIII) S,S'-(2-dimethylaminotrimethylene)-bis(thiocarbamate)(cartap), from *The Pesticide Manual*, $11^{th}$ ed. (1997), The British Crop Protection Council, London, page 193;
(IX) 1-[3,5-dichloro-4-(3-chloro-5-trifluoromethyl-2-pyridyloxy)phenyl]-3-(2,6-difluorobenzoyl)-urea(chlorfluazuron), from *The Pesticide Manual*, $11^{th}$ ed. (1997), The British Crop Protection Council, London, page 213;

(X) O,O-diethyl-O-3,5,6-trichloro-2-pyridyl-phosphorothioate(chlorpyrifos), from *The Pesticide Manual*, 11th ed. (1997), The British Crop Protection Council, London, page 235;

(XI) (RS)-α-cyano-4-fluoro-3-phenoxybenzyl-(1RS,3RS; 1RS,3RS)-3-(2,2-dichlorovinyl)-2,2-dimethylcyclopropanecarboxylate(cyfluthrin), from *The Pesticide Manual*, 11th ed. (1997), The British Crop Protection Council, London, page 293;

(XII) mixture of (S)-α-cyano-3-phenoxybenzyl-(Z)-(1R, 3R)-3-(2-chloro-3,3,3-trifluoropropenyl)-2,2-dimethyl-cyclopropanecarboxylate and (R)-α-cyano-3-phenoxybenzyl-(Z)-(1R,3R)-3-(2-chloro-3,3,3-trifluoropropenyl)-2,2-dimethylcyclopropanecarboxylate(lambda-cyhalothrin), from *The Pesticide Manual*, 11th ed. (1997), The British Crop Protection Council, London, page 300;

(XIII) racemate consisting of (S)-α-cyano-3-phenoxybenzyl-(1R,3R)-3-(2,2-dichlorovinyl)-2,2-dimethylcyclopropanecarboxylate and (R)-α-cyano-3-phenoxybenzyl-(1S, 3S)-3-(2,2-dichlorovinyl)-2,2-dimethylcyclopropanecarboxylate(alpha-cypermethrin), from *The Pesticide Manual*, 11th ed. (1997), The British Crop Protection Council, London, page 308;

(XIV) a mixture of the stereoisomers of (S)-α-cyano-3-phenoxybenzyl (1RS,3RS,1RS,3RS)-3-(2,2-dichlorovinyl)-2,2-dimethylcyclopropanecarboxylate(zeta-cypermethrin), from *The Pesticide Manual*, 11th ed. (1997), The British Crop Protection Council, London, page 314;

(XV) (S)-α-cyano-3-phenoxybenzyl-(1R,3R)-3-(2,2-dibromovinyl)-2,2-dimethylcyclopropanecarboxylate(deltamethrin), from *The Pesticide Manual*, 11th ed. (1997), The British Crop Protection Council, London, page 344;

(XVI) (4-chlorophenyl)-3-(2,6-difluorobenzoyl)urea(diflubenzuron), from *The Pesticide Manual*, 11th ed. (1997), The British Crop Protection Council, London, page 395;

(XVII) (1,4,5,6,7,7-hexachloro-8,9,10-trinorborn-5-en-2,3-ylenebismethylene)-sulfite(endosulfan), from *The Pesticide Manual*, 11th ed. (1997), The British Crop Protection Council, London, page 459;

(XVIII) α-ethylthio-o-tolyl-methylcarbamate(ethiofencarb), from *The Pesticide Manual*, 11th ed. (1997), The British Crop Protection Council, London, page 479;

(XIX) O,O-dimethyl-O-4-nitro-m-tolyl-phosphorothioate (fenitrothibn), from *The Pesticide Manual*, 11th ed. (1997), The British Crop Protection Council, London, page 514;

(XX) 2-sec-butylphenyl-methylcarbamate(fenobucarb), from *The Pesticide Manual*, 11th ed. (1997), The British Crop Protection Council, London, page 516;

(XXI) (RS)-α-cyano-3-phenoxybenzyl-(RS)-2-(4-chlorophenyl)-3-methylbutyrate(fenvalerate), from *The Pesticide Manual*, 11th ed. (1997), The British Crop Protection Council, London, page 539;

(XXII) S-[formyl(methyl)carbamoylmethyl]-O,O-dimethyl-phosphorodithioate(formothion), from *The Pesticide Manual*, 11th ed. (1997), The British Crop Protection Council, London, page 625;

(XXIII) 4-methylthio-3,5-xylyl-methylcarbamate(methiocarb), from *The Pesticide Manual*, 11th ed. (1997), The British Crop Protection Council, London, page 813;

(XXIV) 7-chlorobicyclo[3.2.0]hepta-2,6-dien-6-yl-dimethylphosphate(heptenophos), from *The Pesticide Manual*, 11th ed. (1997), The British Crop Protection Council, London, page 670;

(XXV) 1-(6-chloro-3-pyridylmethyl)-N-nitroimidazolidin-2-ylideneamine(imidacloprid), from *The Pesticide Manual*, 11th ed. (1997), The British Crop Protection Council, London, page 706;

(XXVI) 2-isopropylphenyl-methylcarbamate(isoprocarb), from *The Pesticide Manual*, 11th ed. (1997), The British Crop Protection Council, London, page 729;

(XXVII) O,S-dimethyl-phosphoramidothioate(methamidophos), from *The Pesticide Manual*, 11th ed. (1997), The British Crop Protection Council, London, page 808;

(XXVIII) S-methyl-N-(methylcarbamoyloxy)thioacetimidate(methomyl), from *The Pesticide Manual*, 11th ed. (1997), The British Crop Protection Council, London, page 815;

(XXIX) methyl-3-(dimethoxyphosphinoyloxy)but-2-enoate (mevinphos), from *The Pesticide Manual*, 11th ed. (1997), The British Crop Protection Council, London, page 844;

(XXX) O,O-diethyl-O-4-nitrophenyl-phosphorothioate(parathion), from *The Pesticide Manual*, 11th ed. (1997), The British Crop Protection Council, London, page 926;

(XXXI) O,O-dimethyl-O-4-nitrophenyl-phosphorothioate (parathion-methyl), from *The Pesticide Manual*, 11th ed. (1997), The British Crop Protection Council, London, page 928;

(XXXII) S-6-chloro-2,3-dihydro-2-oxo-1,3-benzoxazol-3-ylmethyl-O,O-diethyl-phosphoro-dithioate(phosalone), from *The Pesticide Manual*, 11th ed. (1997), The British Crop Protection Council, London, page 963;

(XXXIII) 2-dimethylamino-5,6-dimethylpyrimidin-4-yl-dimethylcarbamate(pirimicarb), from *The Pesticide Manual*, 11th ed. (1997), The British Crop Protection Council, London, page 985;

(XXXIV) 2-isopropoxyphenyl-methylcarbamate(propoxur), from *The Pesticide Manual*, 11th ed. (1997), The British Crop Protection Council, London, page 1036;

(XXXV) 1-(3,5-dichloro-2,4-difluorophenyl)-3-(2,6-difluorobenzoyl)urea(teflubenzuron), from *The Pesticide Manual*, 11th ed. (1997), The British Crop Protection Council, London, page 1158;

(XXXVI) S-tert-butylthiomethyl-O,O-dimethyl-phosphorodithioate(terbufos), from *The Pesticide Manual*, 11th ed. (1997), The British Crop Protection Council, London, page 1165;

(XXXVII) ethyl-(3-tert-butyl-1-dimethylcarbamoyl-1H-1,2, 4-triazol-5-yl-thio)-acetate, (triazamate), from *The Pesticide Manual*, 11th ed. (1997), The British Crop Protection Council, London, page 1224;

(XXXVIII) abamectin, from *The Pesticide Manual*, 11th ed. (1997), The British Crop Protection Council, London, page 3;

(XXXIX) 2-sec-butylphenyl-methylcarbamate(fenobucarb), from *The Pesticide Manual*, 11th ed. (1997), The British Crop Protection Council, London, page 516;

(XL) N-tert-butyl-N'-(4-ethylbenzoyl)-3,5-dimethylbenzohydrazide(tebufenozide), from *The Pesticide Manual*, 11th ed. (1997), The British Crop Protection Council, London, page 1147;

(XLI) (±)-5-amino-1-(2,6-dichloro-α,α,α-trifluoro-p-tolyl)-4-trifluoromethyl-sulfinylpyrazole-3-carbonitrile (fipronil), from *The Pesticide Manual*, 11th ed. (1997), The British Crop Protection Council, London, page 545;

(XLII) (RS)-α-cyano-4-fluoro-3-phenoxybenzyl(1RS,3RS; 1RS,3RS)-3-(2,2-dichlorovinyl)-2,2-dimethylcyclopropanecarboxylate(beta-cyfluthrin), from *The Pesticide Manual*, 11th ed. (1997), The British Crop Protection Council, London, page 295;

(XLIII) (4-ethoxyphenyl)-[3-(4-fluoro-3-phenoxyphenyl) propyl](dimethyl)silane(silafluofen), from *The Pesticide Manual*, 11$^{th}$ ed. (1997), The British Crop Protection Council, London, page 1105;

(XLIV) tert-butyl (E)-α-(1,3-dimethyl-5-phenoxypyrazol-4-yl-methyleneamino-oxy)-p-toluate(fenpyroximate), from *The Pesticide Manual*, 11$^{th}$ ed. (1997), The British Crop Protection Council, London, page 530;

(XLV) 2-tert-butyl-5-(4-tert-butylbenzylthio)-4-chloropyridazin-3(2H)-one(pyridaben), from *The Pesticide Manual*, 11$^{th}$ ed. (1997), The British Crop Protection Council, London, page 1161;

(XLVI) 4-[[4-(1,1-dimethylphenyl)phenyl]ethoxy]-quinazoline(fenazaquin), from *The Pesticide Manual*, 11$^{th}$ ed. (1997), The British Crop Protection Council, London, page 507;

(XLVII) 4-phenoxyphenyl-(RS)-2-(pyridyloxy)propyl ether (pyriproxyfen), from *The Pesticide Manual*, 11$^{th}$ ed. (1997), The British Crop Protection Council, London, page 1073;

(XLVIII) 5-chloro-N-{2-[4-(2-ethoxyethyl)-2,3-dimethylphenoxy]ethyl}-6-ethylpyrimidine-4-amine(pyrimidifen), from *The Pesticide Manual*, 11$^{th}$ ed. (1997), The British Crop Protection Council, London, page 1070;

(XLIX) (E)-N-(6-chloro-3-pyridylmethyl)-N-ethyl-N'-methyl-2-nitrovinylidenediamine(nitenpyram), from *The Pesticide Manual*, 11$^{th}$ ed. (1997), The British Crop Protection Council, London, page 880;

(L) (E)-N$^1$-[(6-chloro-3-pyridyl)methyl]-N$^2$-cyano-N$^1$-methylacetamidine (NI-25, acetamiprid), from *The Pesticide Manual*, 11$^{th}$ ed. (1997), The British Crop Protection Council, London, page 9;

(LI) avermectin B$_1$, from *The Pesticide Manual*, 11$^{th}$ ed. (1997), The British Crop Protection Council, London, page 3;

(LII) an insect-active extract from a plant, especially (2R, 6aS,12aS)-1,2,6,6a,12,12a-hexahydro-2-isopropenyl-8,9-dimethoxy-chromeno[3,4-b]furo[2,3-h]chromen-6-one (rotenone), from *The Pesticide Manual*, 11$^{th}$ ed. (1997), The British Crop Protection Council, London, page 1097; and an extract from *Azadirachta indica*, especially azadirachtin, from *The Pesticide Manual*, 11$^{th}$ ed. (1997), The British Crop Protection Council, London, page 59; and (LIII) a preparation containing insect-active nematodes, preferably *Heterorhabditis bacteriophora* and *Heterorhabditis megidis*, from *The Pesticide Manual*, 11$^{th}$ ed. (1997), The British Crop Protection Council, London, page 671; *Steinernema feltiae*, from *The Pesticide Manual*, 11$^{th}$ ed. (1997), The British Crop Protection Council, London, page 1115, and *Steinernema scapterisci*, from *The Pesticide Manual*, 11$^{th}$ ed. (1997), The British Crop Protection Council, London, page 1116;

(LIV) a preparation, obtainable from *Bacillus subtilis*, from *The Pesticide Manual*, 11$^{th}$ ed. (1997), The British Crop Protection Council, London, page 72; or from a *Bacillus thuringiensis* strain with the exception of compounds isolated from GC91 or from NCTC11821; *The Pesticide Manual*, 11$^{th}$ ed. (1997), The British Crop Protection Council, London, page 73;

(LV) a preparation containing insect-active fungi, preferably *Verticillium lecanii*, from *The Pesticide Manual*, 11$^{th}$ ed. (1997), The British Crop Protection Council, London, page 1266; *Beauveria brogniartii*, from *The Pesticide Manual*, 11$^{th}$ ed. (1997), The British Crop Protection Council, London, page 85; and *Beauveria bassiana*, from *The Pesticide Manual*, 11$^{th}$ ed. (1997), The British Crop Protection Council, London, page 83;

(LVI) a preparation containing insect-active viruses, preferably Neodipridon Sertifer NPV, from *The Pesticide Manual*, 11$^{th}$ ed. (1997), The British Crop Protection Council, London, page 1342; *Mamestra brassicae* NPV, from *The Pesticide Manual*, 11$^{th}$ ed. (1997), The British Crop Protection Council, London, page 759; and *Cydia pomonella granulosis* virus, from *The Pesticide Manual*, 11$^{th}$ ed. (1997), The British Crop Protection Council, London, page 291;

(CLXXXI) 7-chloro-2,3,4a,5-tetrahydro-2-[methoxycarbonyl(4-trifluoromethoxyphenyl)carbamoyl]indol[1,2e]oxazoline-4a-carboxylate (DPX-MP062, indoxycarb), from *The Pesticide Manual*, 11$^{th}$ ed. (1997), The British Crop Protection Council, London, page 453;

(CLXXXII) N'-tert-butyl-N'-(3,5-dimethylbenzoyl)-3-methoxy-2-methylbenzohydrazide (RH-2485, methoxyfenozide), from *The Pesticide Manual*, 11$^{th}$ ed. (1997), The British Crop Protection Council, London, page 1094; and (CLXXXIII) (N'-[4-methoxy-biphenyl-3-yl]-hydrazinecarboxylic acid isopropyl ester (D 2341), from Brighton Crop Protection Conference, pp. 487-493 (1996);

(R2) Book of Abstracts, 212th ACS National Meeting Orlando, Fla., Aug. 25-29 1996, AGRO-020. Publisher: American Chemical Society, Washington, D.C. CONEN: 63BFAF.

In accordance with the above remarks, a further important aspect of the present invention relates to combination preparations for controlling parasites on warm-blooded animals which comprise, in addition to a compound of formula (I), at least one further active ingredient having the same or a different direction of action and at least one physiologically tolerable carrier. The present invention is not restricted to two-component combinations.

Within the scope of the present invention preference is given, for example, to the following two-component combinations, the figure in parenthesis representing one of the combination partners mentioned above and the number following the symbol "&" representing a compound from the Tables which follow:

(IX) & 1.001; (IX) & 1.008; (IX) & 1.011; (IX) & 1.012; (IX) & 1.013; (IX) & 1.014; (IX) & 1.015; (IX) & 1.018; (IX) & 1.019; (IX) & 1.020; (IX) & 1.021; (IX) & 1.022; (IX) & 1.054; (IX) & 1.055; (IX) & 1.056; (IX) & 1.057; (IX) & 1.058; (XIII) & 1.001; (XIII) & 1.008; (XIII) & 1.011; (XIII) & 1.012; (XIII) & 1.013; (XIII) & 1.014; (XIII) & 1.015; (XIII) & 1.018; (XIII) & 1.019; (XIII) & 1.020; (XIII) & 1.021; (XIII) & 1.022; (XIII) & 1.054; (XIII) & 1.055; (XIII) & 1.056; (XIII) & 1.057; (XIII) & 1.058; (XIV) & 1.001; (XIV) & 1.008; (XIV) & 1.011; (XIV) & 1.012; (XIV) & 1.013; (XIV) & 1.014; (XIV) & 1.015; (XIV) & 1.018; (XIV) & 1.019; (XIV) & 1.020; (XIV) & 1.021; (XIV) & 1.022; (XIV) & 1.054; (XIV) & 1.055; (XIV) & 1.056; (XIV) & 1.057; (XIV) & 1.058; (LI) & 1.001; (LI) & 1.008; (LI) & 1.011; (LI) & 1.012; (LI) & 1.013; (LI) & 1.014; (LI) & 1.015; (LI) & 1.018; (LI) & 1.019; (LI) & 1.020; (LI) & 1.021; (LI) & 1.022; (LI) & 1.054; (LI) & 1.055; (LI) & 1.056; (LI) & 1.057; (LI) & 1.058; (XXV) & 1.001; (XXV) & 1.008; (XXV) & 1.011; (XXV) & 1.012; (XXV) & 1.013; (XXV) & 1.014; (XXV) & 1.015; (XXV) & 1.018; (XXV) & 1.019; (XXV) & 1.020; (XXV) & 1.021; (XXV) & 1.022; (XXV) & 1.054; (XXV) & 1.055;

(XXV) & 1.056; (XXV) & 1.057; (XXV) & 1.058; (XXXV) & 1.001; (XXXV) & 1.008; (XXXV) & 1.011; (XXXV) & 1.012; (XXXV) & 1.013; (XXXV) & 1.014; (XXXV) & 1.015; (XXXV) & 1.018; (XXXV) & 1.019; (XXXV) & 1.020; (XXXV) & 1.021; (XXXV) & 1.022; (XXXV) & 1.054; (XXXV) & 1.055; (XXXV) & 1.056; (XXXV) & 1.057; (XXXV) & 1.058; (XXXVIII) & 1.001; (XXXVIII) & 1.008; (XXXVIII) & 1.011; (XXXVIII) & 1.012; (XXXVIII) & 1.013; (XXXVIII) & 1.014; (XXXVIII) & 1.015; (XXXVIII) & 1.018; (XXXVIII) & 1.019; (XXXVIII) & 1.020; (XXXVIII) & 1.021; (XXXVIII) & 1.022; (XXXVIII) & 1.054; (XXXVIII) & 1.055; (XXXVIII) & 1.056; (XXXVIII) & 1.057; (XXXVIII) & 1.058; (XLI) & 1.001; (XLI) & 1.008; (XLI) & 1.011; (XLI) & 1.012; (XLI) & 1.013; (XLI) & 1.014; (XLI) & 1.015; (XLI) & 1.018; (XLI) & 1.019; (XLI) & 1.020; (XLI) & 1.021; (XLI) & 1.022; (XLI) & 1.054; (XLI) & 1.055; (XLI) & 1.056; (XLI) & 1.057; (XLI) & 1.058; (XLVII) & 1.001; (XLVII) & 1.008; (XLVII) & 1.011; (XLVII) & 1.012; (XLVII) & 1.013; (XLVII) & 1.014; (XLVII) & 1.015; (XLVII) & 1.018; (XLVII) & 1.019; (XLVII) & 1.020; (XLVII) & 1.021; (XLVII) & 1.022; (XLVII) & 1.054; (XLVII) & 1.055; (XLVII) & 1.056; (XLVII) & 1.057; (XLVII) & 1.058; (XLIX) & 1.001; (XLIX) & 1.008; (XLIX) & 1.011; (XLIX) & 1.012; (XLIX) & 1.013; (XLIX) & 1.014; (XLIX) & 1.015; (XLIX) & 1.018; (XLIX) & 1.019; (XLIX) & 1.020; (XLIX) & 1.021; (XLIX) & 1.022; (XLIX) & 1.054; (XLIX) & 1.055; (XLIX) & 1.056; (XLIX) & 1.057; (XLIX) & 1.058; (LXI) & 1.001; (LXI) & 1.008; (LXI) & 1.011; (LXI) & 1.012; (LXI) & 1.013; (LXI) & 1.014; (LXI) & 1.015; (LXI) & 1.018; (LXI) & 1.019; (LXI) & 1.020; (LXI) & 1.021; (LXI) & 1.022; (LXI) & 1.054; (LXI) & 1.055; (LXI) & 1.056; (LXI) & 1.057; (LXI) & 1.058; (LXII) & 1.001; (LXII) & 1.008; (LXII) & 1.011; (LXII) & 1.012; (LXII) & 1.013; (LXII) & 1.014; (LXII) & 1.015; (LXII) & 1.018; (LXII) & 1.019; (LXII) & 1.020; (LXII) & 1.021; (LXII) & 1.022; (LXII) & 1.054; (LXII) & 1.055; (LXII) & 1.056; (LXII) & 1.057; (LXII) & 1.058; (CIX) & 1.001; (CIX) & 1.008; (CIX) & 1.011; (CIX) & 1.012; (CIX) & 1.013; (CIX) & 1.014; (CIX) & 1.015; (CIX) & 1.018; (CIX) & 1.019; (CIX) & 1.020; (CIX) & 1.021; (CIX) & 1.022; (CIX) & 1.054; (CIX) & 1.055; (CIX) & 1.056; (CIX) & 1.057; (CIX) & 1.058; (CXIII) & 1.001; (CXIII) & 1.008; (CXIII) & 1.011; (CXIII) & 1.012; (CXIII) & 1.013; (CXIII) & 1.014; (CXIII) & 1.015; (CXIII) & 1.018; (CXIII) & 1.019; (CXIII) & 1.020; (CXIII) & 1.021; (CXIII) & 1.022; (CXIII) & 1.054; (CXIII) & 1.055; (CXIII) & 1.056; (CXIII) & 1.057; (CXIII) & 1.058; (CXIX) & 1.001; (CXIX) & 1.008; (CXIX) & 1.011; (CXIX) & 1.012; (CXIX) & 1.013; (CXIX) & 1.014; (CXIX) & 1.015; (CXIX) & 1.018; (CXIX) & 1.019; (CXIX) & 1.020; (CXIX) & 1.021; (CXIX) & 1.022; (CXIX) & 1.054; (CXIX) & 1.055; (CXIX) & 1.056; (CXIX) & 1.057; (CXIX) & 1.058; (CXXIV) & 1.001; (CXXIV) & 1.008; (CXXIV) & 1.011; (CXXIV) & 1.012; (CXXIV) & 1.013; (CXXIV) & 1.014; (CXXIV) & 1.015; (CXXIV) & 1.018; (CXXIV) & 1.019; (CXXIV) & 1.020; (CXXIV) & 1.021; (CXXIV) & 1.022; (CXXIV) & 1.054; (CXXIV) & 1.055; (CXXIV) & 1.056; (CXXIV) & 1.057; (CXXIV) & 1.058; (CXXXI) & 1.001; (CXXXI) & 1.008; (CXXXI) & 1.011; (CXXXI) & 1.012; (CXXXI) & 1.013; (CXXXI) & 1.014; (CXXXI) & 1.015; (CXXXI) & 1.018; (CXXXI) & 1.019; (CXXXI) & 1.020; (CXXXI) & 1.021; (CXXXI) & 1.022; (CXXXI) & 1.054; (CXXXI) & 1.055; (CXXXI) & 1.056; (CXXXI) & 1.057; (CXXXI) & 1.058; (CXXXII) & 1.001; (CXXXII) & 1.008; (CXXXII) & 1.011; (CXXXII) & 1.012; (CXXXII) & 1.013; (CXXXII) & 1.014; (CXXXII) & 1.015; (CXXXII) & 1.018; (CXXXII) & 1.019; (CXXXII) & 1.020; (CXXXII) & 1.021; (CXXXII) & 1.022; (CXXXII) & 1.054; (CXXXII) & 1.055; (CXXXII) & 1.056; (CXXXII) & 1.057; (CXXXII) & 1.058; (CXXXIX) & 1.001; (CXXXIX) & 1.008; (CXXXIX) & 1.011; (CXXXIX) & 1.012; (CXXXIX) & 1.013; (CXXXIX) & 1.014; (CXXXIX) & 1.015; (CXXXIX) & 1.018; (CXXXIX) & 1.019; (CXXXIX) & 1.020; (CXXXIX) & 1.021; (CXXXIX) & 1.022; (CXXXIX) & 1.054; (CXXXIX) & 1.055; (CXXXIX) & 1.056; (CXXXIX) & 1.057; (CXXXIX) & 1.058; (CLII) & 1.001; (CLII) & 1.008; (CLII) & 1.011; (CLII) & 1.012; (CLII) & 1.013; (CLII) & 1.014; (CLII) & 1.015; (CLII) & 1.018; (CLII) & 1.019; (CLII) & 1.020; (CLII) & 1.021; (CLII) & 1.022; (CLII) & 1.054; (CLII) & 1.055; (CLII) & 1.056; (CLII) & 1.057; (CLII) & 1.058; (CLIII) & 1.001; (CLIII) & 1.008; (CLIII) & 1.011; (CLIII) & 1.012; (CLIII) & 1.013; (CLIII) & 1.014; (CLIII) & 1.015; (CLIII) & 1.018; (CLIII) & 1.019; (CLIII) & 1.020; (CLIII) & 1.021; (CLIII) & 1.022; (CLIII) & 1.054; (CLIII) & 1.055; (CLIII) & 1.056; (CLIII) & 1.057; (CLIII) & 1.058; (CLIX) & 1.001; (CLIX) & 1.008; (CLIX) & 1.011; (CLIX) & 1.012; (CLIX) & 1.013; (CLIX) & 1.014; (CLIX) & 1.015; (CLIX) & 1.018; (CLIX) & 1.019; (CLIX) & 1.020; (CLIX) & 1.021; (CLIX) & 1.022; (CLIX) & 1.054; (CLIX) & 1.055; (CLIX) & 1.056; (CLIX) & 1.057; (CLIX) & 1.058; (CLXXIII) & 1.001; (CLXXIII) & 1.008; (CLXXIII) & 1.011; (CLXXIII) & 1.012; (CLXXIII) & 1.013; (CLXXIII) & 1.014; (CLXXIII) & 1.015; (CLXXIII) & 1.018; (CLXXIII) & 1.019; (CLXXIII) & 1.020; (CLXXIII) & 1.021; (CLXXIII) & 1.022; (CLXXIII) & 1.054; (CLXXIII) & 1.055; (CLXXIII) & 1.056; (CLXXIII) & 1.057; (CLXXIII) & 1.058; (CLXXV) & 1.001; (CLXXV) & 1.008; (CLXXV) & 1.011; (CLXXV) & 1.012; (CLXXV) & 1.013; (CLXXV) & 1.014; (CLXXV) & 1.015; (CLXXV) & 1.018; (CLXXV) & 1.019; (CLXXV) & 1.020; (CLXXV) & 1.021; (CLXXV) & 1.022; (CLXXV) & 1.054; (CLXXV) & 1.055; (CLXXV) & 1.056; (CLXXV) & 1.057; (CLXXV) & 1.058; (CLXXXI) & 1.001; (CLXXXI) & 1.008; (CLXXXI) & 1.011; (CLXXXI) & 1.012; (CLXXXI) & 1.013; (CLXXXI) & 1.014; (CLXXXI) & 1.015; (CLXXXI) & 1.018; (CLXXXI) & 1.019; (CLXXXI) & 1.020; (CLXXXI) & 1.021; (CLXXXI) & 1.022; (CLXXXI) & 1.054; (CLXXXI) & 1.055; (CLXXXI) & 1.056; (CLXXXI) & 1.057; (CLXXXI) & 1.058; (CLXXXV) & 1.001; (CLXXXV) & 1.008; (CLXXXV) & 1.011; (CLXXXV) & 1.012; (CLXXXV) & 1.013; (CLXXXV) & 1.014; (CLXXXV) & 1.015; (CLXXXV) & 1.018; (CLXXXV) & 1.019; (CLXXXV) & 1.020; (CLXXXV) & 1.021; (CLXXXV) & 1.022; (CLXXXV) & 1.054; (CLXXXV) & 1.055; (CLXXXV) & 1.056; (CLXXXV) & 1.057; (CLXXXV) & 1.058; (CLXXXVI) & 1.001; (CLXXXVI) & 1.008;

(CLXXXVI) & 1.011; (CLXXXVI) & 1.012; (CLXXXVI) & 1.013; (CLXXXVI) & 1.014; (CLXXXVI) & 1.015; (CLXXXVI) & 1.018; (CLXXXVI) & 1.019; (CLXXXVI) & 1.020; (CLXXXVI) & 1.021; (CLXXXVI) & 1.022; (CLXXXVI) & 1.054; (CLXXXVI) & 1.055; (CLXXXVI) & 1.056; (CLXXXVI) & 1.057; (CLXXXVI) & 1.058; (CLXXXVII) & 1.001; (CLXXXVII) & 1.008; (CLXXXVII) & 1.011; (CLXXXVII) & 1.012; (CLXXXVII) & 1.013; (CLXXXVII) & 1.014; (CLXXXVII) & 1.015; (CLXXXVII) & 1.018; (CLXXXVII) & 1.019; (CLXXXVII) & 1.020; (CLXXXVII) & 1.021; (CLXXXVII) & 1.022; (CLXXXVII) & 1.054; (CLXXXVII) & 1.055; (CLXXXVII) & 1.056; (CLXXXVII) & 1.057; (CLXXXVII) & 1.058; (CLXXXVIII) & 1.001; (CLXXXVIII) & 1.008; (CLXXXVIII) & 1.011; (CLXXXVIII) & 1.012; (CLXXXVIII) & 1.013; (CLXXXVIII) & 1.014; (CLXXXVIII) & 1.015; (CLXXXVIII) & 1.018; (CLXXXVIII) & 1.019; (CLXXXVIII) & 1.020; (CLXXXVIII) & 1.021; (CLXXXVIII) & 1.022; (CLXXXVIII) & 1.054; (CLXXXVIII) & 1.055; (CLXXXVIII) & 1.056; (CLXXXVIII) & 1.057; (CLXXXVIII) & 1.058; (CLXXXIX) & 1.001; (CLXXXIX) & 1.008; (CLXXXIX) & 1.011; (CLXXXIX) & 1.012; (CLXXXIX) & 1.013; (CLXXXIX) & 1.014; (CLXXXIX) & 1.015; (CLXXXIX) & 1.018; (CLXXXIX) & 1.019; (CLXXXIX) & 1.020; (CLXXXIX) & 1.021; (CLXXXIX) & 1.022; (CLXXXIX) & 1.054; (CLXXXIX) & 1.055; (CLXXXIX) & 1.056; (CLXXXIX) & 1.057; (CLXXXIX) & 1.058; (CXC) & 1.001; (CXC) & 1.008; (CXC) & 1.011; (CXC) & 1.012; (CXC) & 1.013; (CXC) & 1.014; (CXC) & 1.015; (CXC) & 1.018; (CXC) & 1.019; (CXC) & 1.020; (CXC) & 1.021; (CXC) & 1.022; (CXC) & 1.054; (CXC) & 1.055; (CXC) & 1.056; (CXC) & 1.057; (CXC) & 1.058; (CXCL) & 1.001; (CXCL) & 1.008; (CXCL) & 1.011; (CXCL) & 1.012; (CXCL) & 1.013; (CXCL) & 1.014; (CXCL) & 1.015; (CXCL) & 1.018; (CXCL) & 1.019; (CXCL) & 1.020; (CXCL) & 1.021; (CXCL) & 1.022; (CXCL) & 1.054; (CXCL) & 1.055; (CXCL) & 1.056; (CXCL) & 1.057; (CXCL) & 1.058; (A1) & 1.001; (A1) & 1.008; (A1) & 1.011; (A1) & 1.012; (A1) & 1.013; (A1) & 1.014; (A1) & 1.015; (A1) & 1.018; (A1) & 1.019; (A1) & 1.020; (A1) & 1.021; (A1) & 1.022; (A1) & 1.054; (A1) & 1.055; (A1) & 1.056; (A1) & 1.057; (A1) & 1.058; (A2) & 1.001; (A2) & 1.008; (A2) & 1.011; (A2) & 1.012; (A2) & 1.013; (A2) &1.014; (A2) & 1.015; (A1) & 1.018; (A2) & 1.019; (A2) & 1.020; (A2) & 1.021; (A2) & 1.022; (A2) & 1.054; (A2) & 1.055; (A2) & 1.056; (A2) & 1.057; (A2) & 1.058; (A3) & 1.001; (A3) & 1.008; (A3) & 1.011; (A3) & 1.012; (A3) & 1.013; (A3) & 1.014; (A3) & 1.015; (A3) & 1.018; (A3) & 1.019; (A3) & 1.020; (A3) & 1.021; (A3) & 1.022; (A3) & 1.054; (A3) & 1.055; (A3) & 1.056; (A3) & 1.057; (A3) & 1.058; (A4) & 1.001; (A4) & 1.008; (A4) & 1.011; (A4) & 1.012; (A4) & 1.013; (A4) & 1.014; (A4) & 1.015; (A4) & 1.018; (A4) & 1.019; (A4) & 1.020; (A4) & 1.021; (A4) & 1.022; (A4) & 1.054; (A4) & 1.055; (A4) & 1.056; (A4) & 1.057; (A4) & 1.058; (A5) & 1.001; (A5) & (A5) & 1.008; (A5) & 1.011; (A5) & 1.012; (A5) & 1.013; (A5) & 1.014; (A5) & 1.015; (A5) & 1.018; (A5) & 1.019; (A5) & 1.020; (A5) & 1.021; (A5) & 1.022; (A5) & 1.054; (A5) & 1.055; (A5) & (A5) & 1.056; (A5) & 1.057; (A5) & 1.058; (A6) & 1.001; (A6) & 1.008; (A6) & 1.011; (A6) & 1.012; (A6) & 1.013; (A6) & 1.014; (A6) & 1.015; (A6) & 1.018; (A6) & 1.019; (A6) & 1.020; (A6) & 1.021; (A6) & 1.022; (A6) & 1.054; (A6) & 1.055; (A6) & 1.056; (A6) & 1.057; (A6) & 1.058; (A10) & 1.001; (A10) & 1.008; (A10) & 1.011; (A10) & 1.012; (A10) & 1.013; (A10) & 1.014; (A10) & 1.015; (A10) & 1.018; (A10) & 1.019; (A10) & 1.020; (A10) & 1.021; (A10) & 1.022; (A10) & 1.054; (A10) & 1.055; (A10) & 1.056; (A10) & 1.057; (A10) & 1.058; (A11) & 1.001; (A11) & 1.008; (A11) & 1.011; (A11) & 1.012; (A11) & 1.013; (A11) & 1.014; (A11) & 1.015; (A11) & 1.018; (A11) & 1.019; (A11) & 1.020; (A11) & 1.021; (A11) & 1.022; (A11) & 1.054; (A11) & 1.055; (A11) & 1.056; (A11) & 1.057; (A11) & 1.058; (R1) & 1.001; (R1) & 1.008; (R1) & 1.011; (R1) & 1.012; (R1) & 1.013; (R1) & 1.014; (R1) & 1.015; (R1) & 1.018; (R1) & 1.019; (R1) & 1.020; (R1) & 1.021; (R1) & 1.022; (R1) & 1.054; (R1) & 1.055; (R1) & 1.056; (R1) & 1.057; (R1) & 1.058; (R2) & 1.001; (R2) & 1.008; (R2) & 1.011; (R2) & 1.012; (R2) & 1.013; (R2) & 1.014; (R2) & 1.015; (R2) & 1.018; (R2) & 1.019; (R2) & 1.020; (R2) & 1.021; (R2) & 1.022; (R2) & 1.054; (R2) & 1.055; (R2) & 1.056; (R2) & 1.057; (R2) & 1.058; (R3) & 1.001; (R3) & 1.008; (R3) & 1.011; (R3) & 1.012; (R3) & 1.013; (R3) & 1.014; (R3) & 1.015; (R3) & 1.018; (R3) & 1.019; (R3) & 1.020; (R3) & 1.021; (R3) & 1.022; (R3) & 1.054; (R3) & 1.055; (R3) & 1.056; (R3) & 1.057; (R3) & 1.058; (IX) & 1.059; (IX) & 1.060; (IX) & 1.061; (IX) & 1.062; (IX) & 1.063; (IX) & 1.064; (IX) & 1.065; (IX) & 1.066; (IX) & 1.067; (IX) & 1.068; (IX) & 1.069; (IX) & 1.070; (IX) & 1.071; (IX) & 1.072; (IX) & 1.073; (IX) & 1.074; (IX) & 1.075; (IX) & 1.076; (IX) & 1.077; (IX) & 1.078; (IX) & 1.079; (IX) & 1.080; (IX) & 1.081; (IX) & 1.082; (IX) & 1.083; (IX) & 1.084; (IX) & 1.085; (IX) & 1.086; (IX) & 1.087; (XIII) & 1.059; (XIII) & 1.060; (XIII) & 1.061; (XIII) & 1.062; (XIII) & 1.063; (XIII) & 1.064; (XIII) & 1.065; (XIII) & 1.066; (XIII) & 1.067; (XIII) & 1.068; (XIII) & 1.069; (XIII) & 1.070; (XIII) & 1.071; (XIII) & 1.072; (XIII) & 1.073; (XIII) & 1.074; (XIII) & 1.075; (XIII) & 1.076; (XIII) & 1.077; (XIII) & 1.078; (XIII) & 1.079; (XIII) & 1.080; (XIII) & 1.081; (XIII) & 1.082; (XIII) & 1.083; (XIII) & 1.084; (XIII) & 1.085; (XIII) & 1.086; (XIII) & 1.087; (XIV) & 1.059; (XIV) & 1.060; (XIV) & 1.061; (XIV) & 1.062; (XIV) & 1.063; (XIV) & 1.064; (XIV) & 1.065; (XIV) & 1.066; (XIV) & 1.067; (XIV) & 1.068; (XIV) & 1.069; (XIV) & 1.070; (XIV) & 1.071; (XIV) & 1.072; (XIV) & 1.073; (XIV) & 1.074; (XIV) & 1.075; (XIV) & 1.076; (XIV) & 1.077; (XIV) & 1.078; (XIV) & 1.079; (XIV) & 1.080; (XIV) & 1.081; (XIV) & 1.082; (XIV) & 1.083; (XIV) & 1.084; (XIV) & 1.085; (XIV) & 1.086; (XIV) & 1.087; (LI) & 1.059; (LI) & 1.060; (LI) & 1.061; (LI) & 1.062; (LI) & 1.063; (LI) & 1.064; (LI) & 1.065; (LI) & 1.066; (LI) & 1.067; (LI) & 1.068; (LI) & 1.069; (LI) & 1.070; (LI) & 1.071; (LI) & 1.072; (LI) & 1.073; (LI) & 1.074; (LI) & 1.075; (LI) & 1.076; (LI) & 1.077; (LI) & 1.078; (LI) & 1.079; (LI) & 1.080; (LI) & 1.081; (LI) & 1.082; (LI) & 1.083; (LI) & 1.084; (LI) & 1.085; (LI) & 1.086; (LI) & 1.087; (XXV) & 1.059; (XXV) & 1.060; (XXV) & 1.061; (XXV) & 1.062; (XXV) & 1.063; (XXV) & 1.064; (XXV) & 1.065; (XXV) & 1.066; (XXV) & 1.067; (XXV) & 1.068; (XXV) & 1.069; (XXV) & 1.070; (XXV) & 1.071; (XXV) & 1.072; (XXV) & 1.073; (XXV) & 1.074; (XXV) & 1.075; (XXV) & 1.076; (XXV) & 1.077; (XXV) & 1.078; (XXV) & 1.079; (XXV) & 1.080; (XXV) & 1.081; (XXV) & 1.082; (XXV) & 1.083; (XXV) & 1.084; (XXV) & 1.085; (XXV) & 1.086; (XXV) & 1.087; (XXXV) & 1.059; (XXXV) & 1.060; (XXXV) & 1.061;

(XXXV) & 1.062; (XXXV) & 1.063; (XXXV) & 1.064; (XXXV) & 1.065; (XXXV) & 1.066; (XXXV) & 1.067; (XXXV) & 1.068; (XXXV) & 1.069; (XXXV) & 1.070; (XXXV) & 1.071; (XXXV) & 1.072; (XXXV) & 1.073; (XXXV) & 1.074; (XXXV) & 1.075; (XXXV) & 1.076; (XXXV) & 1.077; (XXXV) & 1.078; (XXXV) & 1.079; (XXXV) & 1.080; (XXXV) & 1.081; (XXXV) & 1.082; (XXXV) & 1.083; (XXXV) & 1.084; (XXXV) & 1.085; (XXXV) & 1.086; (XXXV) &-1.087; (XXXVIII) & 1.059; (XXXVIII) & 1.060; (XXXVIII) & 1.061; (XXXVIII) & 1.062; (XXXVIII) & 1.063; (XXXVIII) & 1.064; (XXXVIII) & 1.065; (XXXVIII) & 1.066; (XXXVIII) & 1.067; (XXXVIII) & 1.068; (XXXVIII) & 1.069; (XXXVIII) & 1.070; (XXXVIII) & 1.071; (XXXVIII) & 1.072; (XXXVIII) & 1.073; (XXXVIII) & 1.074; (XXXVIII) & 1.075; (XXXVIII) & 1.076; (XXXVIII) & 1.077; (XXXVIII) & 1.078; (XXXVIII) & 1.079; (XXXVIII) & 1.080; (XXXVIII) & 1.081; (XXXVIII) & 1.082; (XXXVIII) & 1.083; (XXXVIII) & 1.084; (XXXVIII) & 1.085; (XXXVIII) & 1.086; (XXXVIII) & 1.087; (XLI) & 1.059; (XLI) & 1.060; (XLI) & 1.061; (XLI) & 1.062; (XLI) & 1.063; (XLI) & 1.064; (XLI) & 1.065; (XLI) & 1.066; (XLI) & 1.067; (XLI) & 1.068; (XLI) & 1.069; (XLI) & 1.070; (XLI) & 1.071; (XLI) & 1.072; (XLI) & 1.073; (XLI) & 1.074; (XLI) & 1.075; (XLI) & 1.076; (XLI) & 1.077; (XLI) & 1.078; (XLI) & 1.079; (XLI) & 1.080; (XLI) & 1.081; (XLI) & 1.082; (XLI) & 1.083; (XLI) & 1.084; (XLI) & 1.085; (XLI) & 1.086; (XLI) & 1.087; (XLVII) & 1.059; (XLVII) & 1.060; (XLVII) & 1.061; (XLVII) & 1.062; (XLVII) & 1.063; (CIX) & 1.064; (XLVII) & 1.065; (XLVII) & 1.066; (XLVII) & 1.067; (XLVII) & 1.068; (XLVII) & 1.069; (XLV!I) & 1.070; (XLVII) & 1.071; (XLVII) & 1.072; (XLVII) & 1.073; (XLVII) & 1.074; (XLVII) & 1.075; (XLVII) & 1.076; (XLVII) & 1.077; (XLVII) & 1.078; (XLVII) & 1.079; (XLVII) & 1.080; (XLVII) & 1.081; (XLVII) & 1.082; (XLVII) & 1.083; (XLVII) & 1.084; (XLVII) & 1.085; (XLVII) & 1.086; (XLVII) & 1.087; (XLIX) & 1.059; (XLIX) & 1.060; (XLIX) & 1.061; (XLIX) & 1.062; (XLIX) & 1.063; (CIX) & 1.064; (XLIX) & 1.065; (XLIX) & 1.066; (XLIX) & 1.067; (XLIX) & 1.068; (XLIX) & 1.069; (XLIX) & 1.070; (XLIX) & 1.071; (XLIX) & 1.072; (XLIX) & 1.073; (XLIX) & 1.074; (XLIX) & 1.075; (XLIX) & 1.076; (XLIX) & 1.077; (XLIX) & 1.078; (XLIX) & 1.079; (XLIX) & 1.080; (XLIX) & 1.081; (XLIX) & 1.082; (XLIX) & 1.083; (XLIX) & 1.084; (XLIX) & 1.085; (XLIX) & 1.086; (XLIX) & 1.087; (LXI) & 1.059; (LXI) & 1.060; (LXI) & 1.061; (LXI) & 1.062; (LXI) & 1.063; (CIX) & 1.064; (LXI) & 1.065; (LXI) & 1.066; (LXI) & 1.067; (LXI) & 1.068; (LXI) & 1.069; (LXI) & 1.070; (LXI) & 1.071; (LXI) & 1.072; (LXI) & 1.073; (LXI) & 1.074; (LXI) & 1.075; (LXI) & 1.076; (LXI) & 1.077; (LXI) & 1.078; (LXI) & 1.079; (LXI) & 1.080; (LXI) & 1.081; (LXI) & 1.082; (LXI) & 1.083; (LXI) & 1.084; (LXI) & 1.085; (LXI) & 1.086; (LXI) & 1.087; (LXII) & 1.059; (LXII) & 1.060; (LXII) & 1.061; (LXII) & 1.062; (LXII) & 1.063; (CIX) & 1.064; (LXII) & 1.065; (LXII) & 1.066; (LXII) & 1.067; (LXII) & 1.068; (LXII) & 1.069; (LXII) & 1.070; (LXII) & 1.071; (LXII) & 1.072; (LXII) & 1.073; (LXII) & 1.074; (LXII) & 1.075; (LXII) & 1.076; (LXII) & 1.077; (LXII) & 1.078; (LXII) & 1.079; (LXII) & 1.080; (LXII) & 1.081; (LXII) & 1.082; (LXII) & 1.083; (LXII) & 1.084; (LXII) & 1.085; (LXII) & 1.086; (LXII) & 1.087; (CIX) & 1.059; (CIX) & 1.060; (CIX) & 1.061; (CIX) & 1.062; (CIX) & 1.063; (CIX) & 1.064; (CIX) & 1.065; (CIX) & 1.066; (CIX) & 1.067; (CIX) & 1.068; (CIX) & 1.069; (CIX) & 1.070; (CIX) & 1.071; (CIX) & 1.072; (CIX) & 1.073; (CIX) & 1.074; (CIX) & 1.075; (CIX) & 1.076; (CIX) & 1.077; (CIX) & 1.078; (CIX) & 1.079; (CIX) & 1.080; (CIX) & 1.081; (CIX) & 1.082; (CIX) & 1.083; (CIX) & 1.084; (CIX) & 1.085; (CIX) & 1.086; (CIX) & 1.087; (CXIII) & 1.059; (CXIII) & 1.060; (CXIII) & 1.061; (CXIII) & 1.062; (CXIII) & 1.063; (CXIII) & 1.064; (CXIII) & 1.065; (CXIII) & 1.066; (CXIII) & 1.067; (CXIII) & 1.068; (CXIII) & 1.069; (CXIII) & 1.070; (CXIII) & 1.071; (CXIII) & 1.072; (CXIII) & 1.073; (CXIII) & 1.074; (CXIII) & 1.075; (CXIII) & 1.076; (CXIII) & 1.077; (CXIII) & 1.078; (CXIII) & 1.079; (CXIII) & 1.080; (CXIII) & 1.081; (CXIII) & 1.082; (CXIII) & 1.083; (CXIII) & 1.084; (CXIII) & 1.085; (CXIII) & 1.086; (CXIII) & 1.087; (CXIX) & 1.059; (CXIX) & 1.060; (CXIX) & 1.061; (CXIX) & 1.062; (CXIX) & 1.063; (CXIX) & 1.064; (CXIX) & 1.065; (CXIX) & 1.066; (CXIX) & 1.067; (CXIX) & 1.068; (CXIX) & 1.069; (CXIX) & 1.070; (CXIX) & 1.071; (CXIX) & 1.072; (CXIX) & 1.073; (CXIX) & 1.074; (CXIX) & 1.075; (CXIX) & 1.076; (CXIX) & 1.077; (CXIX) & 1.078; (CXIX) & 1.079; (CXIX) & 1.080; (CXIX) & 1.081; (CXIX) & 1.082; (CXIX) & 1.083; (CXIX) & 1.084; (CXIX) & 1.085; (CXIX) & 1.086; (CXIX) & 1.087; (CXXIV) & 1.059; (CXXIV) & 1.060; (CXXIV) & 1.061; (CXXIV) & 1.062; (CXXIV) & 1.063; (CXXIV) & 1.064; (CXXIV) & 1.065; (CXXIV) & 1.066; (CXXIV) & 1.067; (CXXIV) & 1.068; (CXXIV) & 1.069; (CXXIV) & 1.070; (CXXIV) & 1.071; (CXXIV) & 1.072; (CXXIV) & 1.073; (CXXIV) & 1.074; (CXXIV) & 1.075; (CXXIV) & 1.076; (CXXIV) & 1.077; (CXXIV) & 1.078; (CXXIV) & 1.079; (CXXIV) & 1.080; (CXXIV) & 1.081; (CXXIV) & 1.082; (CXXIV) & 1.083; (CXXIV) & 1.084; (CXXIV) & 1.085; (CXXIV) & 1.086; (CXXIV) & 1.087; (CXXXI) & 1.059; (CXXXI) & 1.060; (CXXXI) & 1.061; (CXXXI) & 1.062; (CXXXI) & 1.063; (CXXXI) & 1.064; (CXXXI) & 1.065; (CXXXI) & 1.066; (CXXXI) & 1.067; (CXXXI) & 1.068; (CXXXI) & 1.069; (CXXXI) & 1.070; (CXXXI) & 1.071; (CXXXI) & 1.072; (CXXXI) & 1.073; (CXXXI) & 1.074; (CXXXI) & 1.075; (CXXXI) & 1.076; (CXXXI) & 1.077; (CXXXI) & 1.078; (CXXXI) & 1.079; (CXXXI) & 1.080; (CXXXI) & 1.081; (CXXXI) & 1.082; (CXXXI) & 1.083; (CXXXI) & 1.084; (CXXXI) & 1.085; (CXXXI) & 1.086; (CXXXI) & 1.087; (CXXXII) & 1.059; (CXXXII) & 1.060; (CXXXII) & 1.061; (CXXXII) & 1.062; (CXXXII) & 1.063; (CXXXII) & 1.064; (CXXXII) & 1.065; (CXXXII) & 1.066; (CXXXII) & 1.067; (CXXXII) & 1.068; (CXXXII) & 1.069; (CXXXII) & 1.070; (CXXXII) & 1.071; (CXXXII) & 1.072; (CXXXII) & 1.073; (CXXXII) & 1.074; (CXXXII) & 1.075; (CXXXII) & 1.076; (CXXXII) & 1.077; (CXXXII) & 1.078; (CXXXII) & 1.079; (CXXXII) & 1.080; (CXXXII) & 1.081; (CXXXII) & 1.082; (CXXXII) & 1.083; (CXXXII) & 1.084; (CXXXII) & 1.085; (CXXXII) & 1.086; (CXXXII) & 1.087; (CXXXIX) & 1.059; (CXXXIX) & 1.060; (CXXXIX) & 1.061; (CXXXIX) & 1.062; (CXXXIX) & 1.063; (CXXXIX) & 1.064; (CXXXIX) & 1.065; (CXXXIX) & 1.066; (CXXXIX) & 1.067; (CXXXIX) & 1.068; (CXXXIX) & 1.069; (CXXXIX) & 1.070; (CXXXIX) & 1.071; (CXXXIX) & 1.072; (CXXXIX) & 1.073; (CXXXIX) & 1.074; (CXXXIX) &

1.075; (CXXXIX) & 1.076; (CXXXIX) & 1.077; (CXXXIX) & 1.078; (CXXXIX) & 1.079; (CXXXIX) &1.080; (CXXXIX) & 1.081; (CXXXIX) & 1.082; (CXXXIX) & 1.083; (CXXXIX) & 1.084; (CXXXIX) & 1.085; (CXXXIX) & 1.086; (CXXXIX) & 1.087; (A1) & 1.059; (A1) & 1.060; (A1) & 1.061; (A1) & 1.062; (A1) & 1.063; (A1) & 1.064; (A1) & 1.065; (A1) & 1.066; (A1) & 1.067; (A1) & 1.068; (A1) & 1.069; (A1) & 1.070; (A1) & 1.071; (A1) & 1.072; (A1) & 1.073; (A1) & 1.074; (A1) & 1.075; (A1) & 1.076; (A1) & 1.077; (A1) & 1.078; (A1) & 1.079; (A1) & 1.080; (A1) & 1.081; (A1) & 1.082; (A1) & 1.083; (A1) & 1.084; (A1) & 1.085; (A1) & 1.086; (Al) & 1.087; (A2) & 1.059; (A2) & 1.060; (A2) & 1.061; (A2) & 1.062; (A2) & 1.063; (A2) & 1.064; (A2) & 1.065; (A2) & 1,.066; (A2) & 1.067; (A2) & 1.068; (A2) & 1.069; (A2) & 1.070; (A2) & 1.071; (A2) & 1.072 & (A2) & 1.073; (A2) & 1.074; (A2) & 1.075; (A2) & 1.076; (A2) & 1.077; (A2) & 1.078; (A2) & 1.079; (A2) & 1.080; (A2) & 1.081; (A2) & 1.082; (A2) & 1.083; (A2) & 1.084; (A2) & 1.085; (A2) & 1.086; (A2) & 1.087; (A3) & 1.059; (A3) & 1.060; (A3) & 1.061; (A3) & 1.062; (A3) & 1.063; (A3) & 1.064; (A3) & 1.065; (A3) & 1.066; (A3) & 1.067; (A3) & 1.068; (A3) & 1.069; (A3) & 1.070; (A3) & 1.071; (A3) & 1.072; (A3) & 1.073; (A3) & 1.074; (A3) & 1.075; (A3) & 1.076; (A3) & 1.077; (A3) & 1.078; (A3) & 1.079; (A3) & 1.080; (A3) & 1.081; (A3) & 1.083; (A3) & 1.083; (A3) & 1.084; (A3) & 1.085; (A3) & 1.086; (A3) & 1.087; (A4) & 1.059; (A4) & 1.060; (A4) & 1.061; (A4) & 1.062; (A4) & 1.063; (A4) & 1.064; (A4) & 1.065; (A4) & 1.066; (A4) & 1.067; (A4) & 1.068; (A4) & 1.069; (A4) & 1.070; (A4) & 1.071; (A4) & 1.072; (A4) & 1.073; (A4) & 1.074; (A4) & 1.075; (A4) & 1.076; (A4) & 1.077; (A4) & 1.078; (A4) & 1.079; (A4) & 1.080; (A4) & 1.081; (A4) & 1.082; (A4) & 1.083; (A4) & 1.084; (A4) & 1.085; (A4) & 1.086; (A4) & 1.087; (A6) & 1.059; (A6) & 1.060; (A6) & 1.061; (A6) & 1.062; (A6) & 1.063; (A6) & 1.064; (A6) & 1.065; (A6) & 1.066; (A6) & 1.067; (A6) & 1.068; (A6) & 1.069; (A6) & 1.070; (A6) & 1.071; (A6) & 1.072; (A6) & 1.073; (A6) & 1.074; (A6) & 1.075; (A6) & 1.076; (A6) & 1.077; (A6) & 1.078; (A6) & 1.079; (A6) & 1.080; (A6) & 1.081; (A6) & 1.082; (A6) & 1.083; (A6) & 1.084; (A6) & 1.085; (A6) & 1.086; (A6) & 1.087; (R2) & 1.059; (R2) & 1.060; (R2) & 1.061; (R2) & 1.062; (R2) & 1.063; (R2) & 1.064; (R2) & 1.065; (R2) & 1.066; (R2) & 1.067; (R2) & 1.068; (R2) & 1.069; (R2) & 1.070; (R2) & 1.071; (R2) & 1.072; (R2) & 1.073; (R2) & 1.074; (R2) & 1.075; (R2) & 1.076; (R2) & 1.077; (R2) & 1.078; (R2) & 1.079; (R2) & 1080; (R2) & 1.081; (R2) & 1.082; (R2) & 1.083; (R2) & 1.084; (R2) & 1.085; (R2) & 1.086; and (R2) & 1.087, preference being given to those combinations in which a partner is underlined.

The following reaction scheme gives a diagrammatic overview of the preparation of the compounds of formula (I):

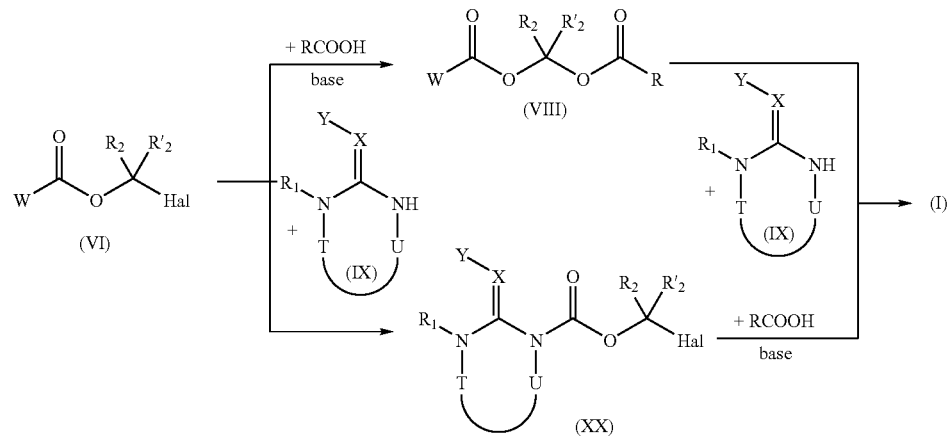

wherein
the substituents R, $R_1$, $R_2$, $R_2'$, X, Y, T and U indicated in the above scheme are as defined for formula (I);
W is a leaving group; and
Hal is halogen, such as fluorine, chlorine, bromine or iodine, preferably chlorine, bromine or iodine.

Leaving groups W in the compounds of formulae (VI) and (VIII) that are suitable for the reactions are known from the literature and are described, e.g., in Houben-Weyl-Methoden der organischen Chemie, Vol. E4-carbonic acid derivatives, pp. 149-165; Hagemann, Eds., Georg Thieme Verlag, Stuttgart (1983). Especially preferred leaving groups are halogen, preferably iodine or chlorine; $C_1$-$C_8$alkoxy, $C_1$-$C_8$alkylthio, phenoxy, N-hydroxy-succinimide, N-hydroxy-phthalimide, imidazole, triazoles and 1-hydroxybenzotriazole-N-oxyl. It will be understood that all leaving groups that contain aliphatic or aromatic rings may be unsubstituted or substituted at those rings by customary substituents.

The compounds of formula (XX) are novel except of 1-(1-chloroethoxycarbonyl)-3-(2-chloro-5-thiatolylmethyl)-1-methyl-2-nitroguanidin, which is described in EP 0 471 371 and in JP-A-05 11251. They exhibit a pesticidal spectrum of action similar to that of the compounds of formula (I). The present invention relates to those compounds also. In the compounds of formula (XX), as regards the substituents $R_1$, $R_2$, $R_2'$, X, Y, T and U preference is given to the same substituents as those already mentioned for the preferred sub-groups of compounds of formula (I), Hal preferably being fluorine or chlorine, especially chlorine. As a result of the Hal substituent, these novel compounds are excellently suitable for further derivatisation and therefore for the preparation of parasiticides, for example, the compounds of formula (I).

The reactions illustrated and described hereinabove and hereinbelow are carried out in a manner known per se, for example, in the absence or, usually, in the presence of a suitable solvent or diluent or a mixture thereof, the operation being carried out, as required, with cooling, at room temperature or with heating, for example in a temperature range of from about −80° C. to the boiling temperature of the reaction medium, preferably from about −40° C. to about +120° C., especially from −20° C. to 40° C. and, if necessary, in a closed vessel, under pressure, in an inert gas atmosphere and/or under anhydrous conditions. Especially advantageous reaction conditions for each individual reaction step can be found in the explanations which follow and in the specific Preparation Examples.

Unless special conditions are mentioned, the reactants can in principle be reacted with one another as such, that is to say without the addition of a solvent or diluent, for example, in the molten state. It is more advantageous, however, to add an inert solvent or diluent or a mixture thereof. Examples of such solvents or diluents that may be mentioned include aromatic, aliphatic and alicyclic hydrocarbons and halogenated hydrocarbons, such as benzene, toluene, xylene, mesitylene, Tetralin, chlorobenzene, dichlorobenzene, bromobenzene, petroleum ether, hexane, cyclohexane, dichloromethane, trichloromethane, tetrachloromethane, dichloroethane, trichloroethene or tetrachloroethene; esters, such as ethyl acetate; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethyl ether, dimethoxydiethyl ether, tetrahydrofuran or dioxane; ketones, such as acetone, methyl ethyl ketone or methyl isobutyl ketone; alcohols, such as methanol, ethanol, propanol, isopropanol, butanol, ethylene glycol or glycerol; amides, such as N,N-dimethylformamide, N,N-diethylformamide, N,N-dimethylacetamide, N-methylpyrrolidone or hexamethylphosphoric acid triamide; nitriles, such as acetonitrile or propionitrile; and sulfoxides, such as dimethyl sulfoxide. If the reaction in question is carried out in the presence of a base, bases used in excess, such as triethylamine, pyridine, N-methylmorpholine or N,N-diethylaniline, may also serve as solvent or diluent. If the reaction is carried out in the presence of an acid catalyst, it is also possible to employ as solvent or diluent acids used in excess, e.g., strong organic carboxylic acids, such as unsubstituted or substituted, e.g., halo-substituted, $C_1$-$C_4$alkanecarboxylic acids, e.g., formic acid, acetic acid or propionic acid. Suitable solvents for the reaction in question can be taken from the Examples given below.

Bases suitable for facilitating those reactions in which base catalysts may optionally be used are, e.g., alkali metal or alkaline earth metal hydroxides, hydrides, alkylides, amides, alkanolates, acetates, carbonates, dialkylamides or alkylsilylamides; alkylamines, alkylenediamines, free or N-alkylated, saturated or unsaturated cycloalkylamines, basic heterocycles, ammonium hydroxides and also carbocyclic amines. Examples are butyllithium, sodium hydroxide, sodium hydride, sodium amide, sodium methanolate, sodium acetate, sodium carbonate, potassium, tert-butanolate, potassium hydroxide, potassium carbonate, potassium hydride, lithium diisopropylamide, potassium bis (trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and also 1,5-diazabicyclo[5.4.0]undec-5-ene (DBU). For replacing chlorine by iodine in a compound of formula (VI), the base used is preferably silver carbonate and the reagent used sodium iodide.

The procedure in detail is as follows: the compounds of formula (I) are prepared by either (a) reacting a compound of formula (IX) in an aprotic, advantageously polar, solvent in the presence of a suitable base and at relatively low temperatures with a compound of formula (VII) or preferably (b) reacting a compound of formula (XX) with an acid RCOOH and isolating the end product from the reaction mixture, the substituents R, $R_1$, $R_2$, $R_{2'}$, X, Y, T and U being as defined for formula (I); W being a leaving group; and Hal being halogen, such as fluorine, chlorine, bromine or iodine, preferably chlorine, bromine or iodine. The reaction is advantageously carried out in an anhydrous medium and under an inert gas atmosphere, e.g., under nitrogen or argon. The said reactions take place within a period of minutes up to several hours.

A preferred embodiment comprises the following features: the compound of formula (IX) is first dissolved in an anhydrous, aprotic, polar solvent, and then at a relatively low temperature, for example, at ambient temperature or lower, an equimolar amount of one of the suitable bases described above, for example, sodium hydride, is added and the mixture is stirred for a little longer at the same temperature. An equimolar amount of the compound of formula (VIII) dissolved in the same solvent is then added in portions, e.g., by dropwise addition, and stirring of the reaction mixture is continued at the same low temperature for a little longer. Any excess base is then neutralized and the reaction mixture is stirred for a few minutes longer and finally concentrated. The residue is advantageously taken up in a polar solvent, such as ethyl acetate, and optionally washed with water, and the organic phase is separated off and dried over a drying agent, e.g., an alkali or alkaline earth metal sulfate or carbonate, preferably magnesium or sodium sulfate, concentrated and purified. A suitable purification step is chromatography, e.g., on silica gel (ethyl acetate: hexane/1:1). Compounds of formula (I) are generally obtained in the form of colourless to dark yellow oils, resins or in the form of solids. The said oils and resins crystallise after a few days or weeks when stored, e.g., in a freezer at about from −18° to −25° C.

In the context of the present invention, relatively low temperatures are to be understood as being temperatures around room temperature and below or a temperature range of from about +25° C. to about −80° C., preferably from room temperature to about −20° C.

The compounds of formula (IX) are known per se from the literature or can be prepared analogously to the examples described in the literature. For example, compounds of formula (IX) wherein Het is pyridyl that is unsubstituted or mono- or poly-substituted by halogen are described, together with their preparation, in European published speci fication EP 0 302 833. Further compounds of formula (IX) are disclosed in the following patent references, e.g., in European published specifications Nos. 285 985; 302 389, 376 279, 471 372, 364 844, 493 369, 381 130, 529 680,163 855, 375 907, 259 738, 386 565, 383 091 and 590 425; U.S. Pat. Nos. 5,063,236, 5,302,605 and 4,742,060; and also in DE 4 207 604; GB 2 228 003 and WO 93/24002.

The compounds of formula (VIII) wherein R, $R_2$ and $R_{2'}$ are as defined for formula (I) and W is one of the leaving groups mentioned above can be prepared by introducing the radical RCOO— into a compound of formula (VI). For that purpose it is advantageous to prepare a suspension of a compound of formula (VI), wherein Hal is iodine and an organic acid R—COOH, an example of which is benzoic acid, and silver carbonate in an aprotic solvent, e.g., toluene or xylene. The suspension is heated at from about 50° C. to about 100° C. for a few hours and then the reaction mixture is cooled to room temperature and insoluble constituents are filtered off. The filtrate is washed with water and/or aqueous sodium chloride solution and dried over a customary drying agent, such as magnesium or sodium sulfate. On concentration, the compound of formula (VIII) is obtained in the form of an oil or a crystalline solid. It is generally unnecessary to carry out further purification before use in the next reaction step.

The preparation of compounds of formula (VI), wherein $R_2$ and $R_{2'}$ are as defined for formula (I);

W is one of the leaving groups mentioned hereinabove; and

Hal is iodine is effected by replacing by iodine the chlorine atom in a compound of formula (VI), wherein Hal is chlorine.

For this purpose a suspension of the compound of formula (VI) wherein Hal is chlorine, an equimolar amount of sodium iodide and sodium hydrogen carbonate in a polar solvent, such as acetone, is prepared and is stirred at slightly elevated temperature, about 40° C., for from 12-24 hours. The resulting precipitate is filtered off and washed with acetone. The filtrate is concentrated, and diethyl ether and water are added. The organic phase is separated off and washed with aqueous potassium sulfite solution, then washed with aqueous sodium chloride solution and dried over a customary drying agent, such as magnesium or sodium sulfate. On concentration, the compound of formula (VI) is obtained in the form of a colourless, crystalline product, which can be filtered off and freed of solvent residues, e.g., in vacuo. Further purification before use in the next reaction step is unnecessary.

Compounds of formula (VI) can be prepared by dissolving compounds of formula (VI), wherein $R_2$ and $R_{2'}$ are as defined for formula (I) and W is chlorine in a halogenated solvent, such as dichloromethane, and at low temperature, advantageously about 0° C., adding a solution of a compound of the formula H—W in portions and then stirring the reaction mixture at the low temperature for about 1-3 hours. Water is then added and the organic phase is separated off, washed with 1 N sodium hydroxide solution and then with aqueous sodium chloride solution and dried over a drying agent, e.g., magnesium sulfate. On concentration, the compound of formula (VI) is obtained in the form of a colorless, crystalline product, which can be filtered off and freed of solvent residues in vacuo.

As illustrated in the above reaction scheme, the novel compounds of formula (XX) are prepared by reacting a compound of formula (IX) in an aprotic, advantageously polar, solvent in the presence of a suitable base and at relatively low temperatures, with a compound of formula (VI), the substituents $R_1$, $R_2$, $R_{2'}$, X, Y, T and U in the formulae (XX), (IX) and (VI) being as defined for formula (I); W being a leaving group; and Hal being halogen, such as fluorine, chlorine, bromine or iodine and preferably chlorine or iodine. The compound of formula (IX) is first dissolved in an anhydrous, aprotic, polar solvent, and then at relatively low temperature, e.g., ambient temperature or lower, an equimolar amount of one of the suitable bases described above, e.g., sodium hydride, is added and the mixture is stirred for a little longer at the same temperature. An equimolar amount of the compound of formula (VI) dissolved in the same solvent is then added in portions, e.g., by dropwise addition, and stirring of the reaction mixture is continued at the same low temperature for a little longer. Any excess base is then neutralised and the reaction mixture is stirred for a few minutes longer and finally concentrated. The residue is advantageously taken up in a polar solvent, such as ethyl acetate, and optionally washed with water, and the organic phase is separated off and dried over a drying agent, e.g., an alkali or alkaline earth metal sulfate or carbonate, preferably magnesium or sodium sulfate, concentrated and purified. A suitable purification step is chromatography, e.g., on silica gel (ethyl acetate:hexane/1:1). Compounds of formula (XX) are generally obtained in the form of colorless to dark yellow oils, resins or, predominantly, in the form of solids.

PREPARATION EXAMPLES

Preparation of Preliminary Products

Preparation of carbonic acid(chloromethyl ester)(4-nitrophenyl ester)

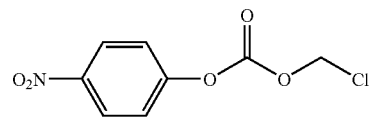

At 0° C., a solution of 69.6 g of 4-nitrophenol and 39.6 g of pyridine in 500 mL of dichloromethane is added dropwise in the course of 30 minutes to a solution of 71 g of chloromethyl chloroformate in 1000 mL of dichloromethane. The reaction mixture is stirred at 0° C. for a further 2 hours and then 1000 mL of $H_2O$ are added. The organic phase is washed using 250 mL each of 1 N NaOH and aqueous sodium chloride solution and dried over $MgSO_4$. After concentration of the solvent, 111 g of a white solid having a melting point of 61-62° C. are obtained.

Preparation of carbonic acid(iodomethyl ester)(4-nitrophenyl ester)

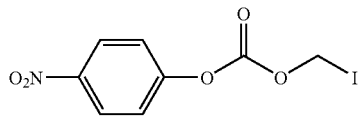

34.8 g of carbonic acid(chloromethyl ester)(4-nitrophenyl ester), 45.0 g of NaI and 2.52 g of NaHCO$_3$ are suspended in 350 mL of acetone and the resulting suspension is stirred at a temperature of 40° C. for 16 hours. The precipitate is filtered off and washed with 100 mL of acetone. The filtrate is concentrated and the residue is taken up in 500 mL of diethyl ether and 100 mL of H$_2$O. The organic phase is washed with 100 mL each of saturated potassium disulfite solution and aqueous sodium chloride solution, dried over MgSO$_4$ and concentrated. 47.4 g of a white solid having a melting point of 45-46° C. are obtained.

Preparation of benzoic acid 4-nitrophenoxycarbonyloxymethyl ester

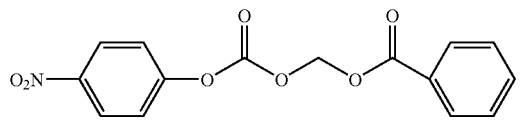

0.97 g of carbonic acid(iodomethyl ester)(4-nitrophenyl ester), 0.55 g of benzoic acid and 1.24 g of Ag$_2$CO$_3$ are suspended in 30 mL of toluene and stirred at 80° C. for 3 hours. The mixture is cooled to room temperature and the precipitate is filtered off. The filtrate is washed with 15 mL each of H$_2$O and aqueous sodium chloride solution, dried over MgSO$_4$ and concentrated. 0.75 g of the desired product is obtained in the form of a white solid having a melting point of 69-71° C.

Preparation of carbonic acid(chloromethyl ester)(N-hydroxysuccinimide ester)

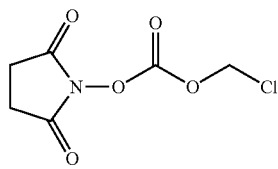

At 0° C., a solution of 99.3 g of N-hydroxysuccinimide and 55.4 g of pyridine in 250 mL of dichloromethane is added in the course of 60 minutes to a solution of 80.6 g of chloromethyl chloroformate in 750 mL of dichloromethane. The reaction mixture is stirred at 0° C. for a further 5 hours and then 1000 mL of H$_2$O are added. The organic phase is washed with 250 mL each of 1 N NaOH and aqueous sodium chloride solution and dried over MgSO$_4$. After concentration of the solvent, 119 g of a white solid having a melting point of 103-105° C. are obtained.

Preparation of {1-[(6-chloro-pyridin-3-ylmethyl)-ethyl-amino]-2-nitro-vinyl}-methyl-carbamic acid) chloromethyl ester

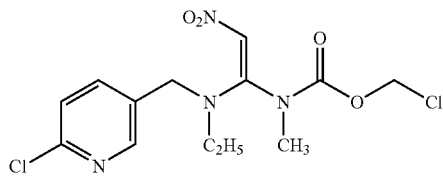

6.35 g of sodium hydride are added in portions at 0° C. under a N$_2$ atmosphere to a solution of 65 g of N-(6-chloro-pyridin-3-ylmethyl)-N-ethyl-N'-methyl]-2-nitro-vinylidene-diamine in 300 mL of DMF. The mixture is stirred at 0° C. for 1 hour and then, at –20° C., 50 g of carbonic acid (chloromethyl ester)(N-hydroxysuccinimide ester) dissolved in 200 mL of DMF are added dropwise thereto. After 1 hour at –20° C., 250 mL of saturated NH$_4$Cl solution and 300 mL of ethyl acetate are added. The organic phase is separated off and washed with 300 mL of 1 N NaOH, 300 mL of water and 300 mL of saturated sodium chloride solution. After drying over MgSO$_4$, the solvent system is concentrated and the residue is stirred at reflux temperature with 300 mL of MeOH. After cooling to room temperature, 33.5 g of whitish-yellow crystals having a melting point of 142-143° C. are obtained.

Preparation of End Products

Preparation of benzoic acid({1-[(6-chloro-pyridin-3-ylmethyl)-ethyl-amino]-2-nitro-vinyl}-methyl-carbamoyloxy)-methyl ester

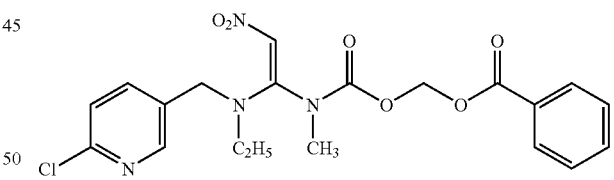

Under a N$_2$ atmosphere, 53 mg of NaH are added to a solution of 270 mg of N-(6-chloro-pyridin-3-ylmethyl)-N-ethyl-N'-methyl]-2-nitro-vinylidenediamine in 20 mL of DMF. The mixture is stirred at room temperature for 1 hour. Then, at –20° C., 635 mg of benzoic acid 4-nitro-phenoxycarbonyloxymethyl ester dissolved in 5 mL of DMF are added dropwise. After 6 hours at –20° C., 1 mL of saturated NH$_4$Cl solution is added and the solvent system is concentrated. The residue is taken up in 50 mL of ethyl acetate and washed with 25 mL of H$_2$O. The organic phase is dried over MgSO$_4$ and concentrated, and the residue is chromatographed on silica gel (ethyl acetate:hexane; 1:1). 450 mg of whitish-yellow crystals having a melting point of 62-63° C. are obtained.

Preparation of 2,2-dimethylbutyric acid {1-[(6-chloro-pyridin-3-ylmethyl)-ethyl-amino]-2-nitro-yinyl}-methyl-carbamoyloxy)-methyl ester

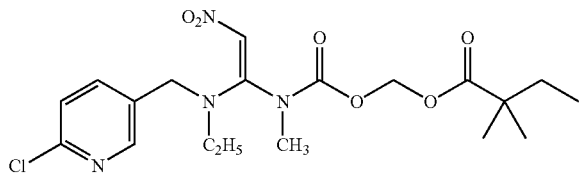

A mixture of 10.9 g of {1-[(6-chloro-pyridin-3-ylmethyl)-ethyl-amino]-2-nitro-vinyl}-methyl-carbamic acid chloromethyl ester, 4.18 g of 2,2-dimethylbutyric acid and 5.39 g of potassium carbonate in 125 mL of DMF is stirred at a temperature of 50° C. for 12 hours. The mixture is cooled to room temperature, the precipitate is filtered off and 250 mL of diethyl ether and 250 mL of 1 N NaOH are added to the filtrate. The organic phase is separated off and washed with 250 mL of water and 250 mL of saturated sodium chloride solution. After drying over $MgSO_4$, the solvent system is concentrated and the residue is stirred with 200 mL of diethyl ether and 100 mL of hexane. 11.1 g of white crystals having a melting point of 79-80° C. are obtained.

In an analogous manner it is also possible to prepare the following typical compounds listed in the Table.

Typical compounds of formula (I) are listed in Tables 1-4, while Tables 5-8 give typical examples of intermediates of formula (XX). The present invention is not limited to the typical examples shown, however.

TABLE 1

Compounds of formula (Xa)

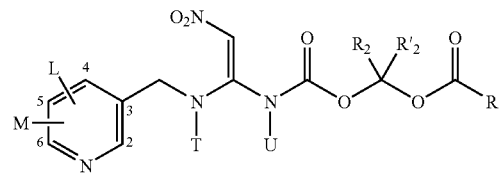

(Xa)

| No. | M | L | T | U | $R_2$ | $R'_2$ | R | Physical Data |
|---|---|---|---|---|---|---|---|---|
| 1.001 | 6-Cl | H | $C_2H_5$ | $CH_3$ | H | H | $CH_3$ | yellow resin |
| 1.002 | 6-Cl | 5-Cl | $C_2H_5$ | $CH_3$ | H | H | $CH_3$ | |
| 1.003 | 6-Cl | H | $CH_3$ | $CH_3$ | H | H | $CH_3$ | |
| 1.004 | 6-Cl | H | $C_2H_5$ | $CH_3$ | $CH_3$ | H | $CH_3$ | |
| 1.005 | 6-Cl | H | $C_2H_5$ | $CH_3$ | H | H | $C_2H_5$ | |
| 1.006 | 6-Cl | H | $C_2H_5$ | $CH_3$ | H | H | $i-C_3H_7$ | |
| 1.007 | 6-Cl | H | $C_2H_5$ | $CH_3$ | H | H | $n-C_3H_7$ | |
| 1.008 | 6-Cl | H | $C_2H_5$ | $CH_3$ | H | H | $n-C_4H_9$ | m.p. 66-68° C. |
| 1.009 | 6-Cl | H | H | $CH_3$ | H | H | $s-C_4H_9$ | |
| 1.010 | H | 5-Cl | $C_2H_5$ | $CH_3$ | H | H | $t-C_4H_9$ | |
| 1.011 | 6-Cl | H | $C_2H_5$ | $CH_3$ | H | H | $n-C_7H_{15}$ | m.p. 84-85° C. |
| 1.012 | 6-Cl | H | $C_2H_5$ | $CH_3$ | H | H | $n-C_{11}H_{23}$ | yellow resin |
| 1.013 | 6-Cl | H | $C_2H_5$ | $CH_3$ | H | H | $n-C_{13}H_{27}$ | m.p. 52-54° C. |
| 1.014 | 6-Cl | H | $C_2H_5$ | $CH_3$ | H | H | $n-C_{15}H_{31}$ | m.p. 56-58° C. |
| 1.015 | 6-Cl | H | $C_2H_5$ | $CH_3$ | H | H | $n-C_{17}H_{35}$ | m.p. 60-61° C. |
| 1.016 | 6-Cl | 5-Cl | $C_2H_5$ | $CH_3$ | H | H | $n-C_{11}H_{23}$ | |
| 1.017 | 6-Cl | 5-F | $CH_3$ | $CH_3$ | H | H | $n-C_7H_{15}$ | |
| 1.018 | 6-Cl | H | $C_2H_5$ | $CH_3$ | H | H | phenyl | glassy m.p. 62-63° C. |
| 1.019 | 6-Cl | H | $C_2H_5$ | $CH_3$ | H | H | $n-C_5H_{11}$ | resin |
| 1.020 | 6-Cl | H | $C_2H_5$ | $CH_3$ | H | H | biphenyl | glassy m.p. 72-69° C. |
| 1.021 | 6-Cl | H | $C_2H_5$ | $CH_3$ | H | H | phenoxyphenyl | glassy m.p. 60-61° C. |
| 1.022 | 6-Cl | H | $C_2H_5$ | $CH_3$ | H | H | 4-t-butyl-phenyl | glassy m.p. 103-5° C. |
| 1.023 | 6-Cl | H | $C_2H_5$ | $CH_3$ | H | H | 2-chloro-phenyl | |
| 1.024 | 6-Cl | H | $C_2H_5$ | $CH_3$ | H | H | 2,6-difluoro-phenyl | |
| 1.025 | 6-Cl | H | $C_2H_5$ | H | H | H | $n-C_{17}H_{35}$ | |
| 1.026 | 6-Cl | H | $C_2H_5$ | $C_2H_5$ | $CH_3$ | H | $n-C_7H_{15}$ | |
| 1.027 | 6-Cl | H | $C_2H_5$ | $CH_3$ | $C_2H_5$ | H | $CH_3$ | |
| 1.028 | 6-Cl | H | $C_2H_5$ | $CH_3$ | $n-C_3H_7$ | H | $CH_3$ | |
| 1.029 | 6-Cl | H | $C_2H_5$ | $CH_3$ | $s-C_4H_9$ | H | $CH_3$ | |
| 1.030 | 6-Cl | H | $C_2H_5$ | $CH_3$ | $n-C_6H_{13}$ | H | $CH_3$ | |
| 1.031 | 6-Cl | H | $CH_3$ | $CH_3$ | $CH_3$ | H | $CH_3$ | |
| 1.032 | 6-Cl | 4-F | $CH_3$ | $CH_3$ | $CH_3$ | H | $CH_3$ | |
| 1.033 | 6-Cl | H | $C_2H_5$ | $CH_3$ | H | H | cyclohexyl | |
| 1.034 | 6-Cl | H | $C_2H_5$ | $CH_3$ | H | H | vinyl | |
| 1.035 | 6-Cl | H | $C_2H_5$ | $CH_3$ | H | H | allyl | |
| 1.036 | 6-Cl | H | $C_2H_5$ | $CH_3$ | H | H | 2-propargyl | |

TABLE 1-continued

Compounds of formula (Xa)

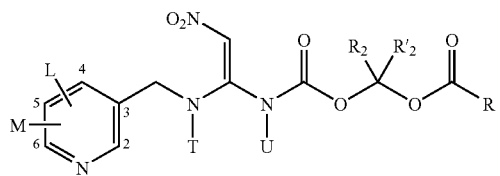

(Xa)

| No. | M | L | T | U | $R_2$ | $R'_2$ | R | Physical Data |
|---|---|---|---|---|---|---|---|---|
| 1.037 | 6-Cl | H | $C_2H_5$ | $CH_3$ | $CH_3$ | $CH_3$ | $CH_3$ | |
| 1.038 | 6-Cl | H | $C_2H_5$ | $CH_3$ | $CH_3$ | $CH_3$ | n-$C_4H_9$ | |
| 1.039 | 6-Cl | H | $C_2H_5$ | $CH_3$ | $CH_3$ | $CH_3$ | n-$C_7H_{15}$ | |
| 1.040 | 6-Cl | H | $C_2H_5$ | $CH_3$ | $C_2H_5$ | $CH_3$ | n-$C_{11}H_{23}$ | |
| 1.041 | 6-Cl | H | $C_2H_5$ | $CH_3$ | $CH_3$ | $CH_3$ | n-$C_{13}H_{27}$ | |
| 1.042 | 6-Cl | H | $C_2H_5$ | $CH_3$ | $C_2H_5$ | $C_2H_5$ | n-$C_{15}H_{31}$ | |
| 1.043 | 6-Cl | H | $C_2H_5$ | $CH_3$ | n-$C_3H_7$ | $C_2H_5$ | n-$C_{17}H_{35}$ | |
| 1.044 | 6-Cl | H | $C_2H_5$ | $CH_3$ | $CH_3$ | s-$C_4H_9$ | phenyl | |
| 1.045 | 6-Cl | H | $C_2H_5$ | $CH_3$ | $CH_3$ | n-$C_3H_7$ | biphenyl | |
| 1.046 | 6-Cl | H | $C_2H_5$ | $CH_3$ | s-$C_4H_9$ | $C_2H_5$ | phenoxyphenyl | |
| 1.047 | 6-Cl | H | $C_2H_5$ | $CH_3$ | s-$C_4H_9$ | $C_2H_5$ | 4-s-butyl-phenyl | |
| 1.048 | 6-Cl | H | $C_2H_5$ | $CH_3$ | s-$C_4H_9$ | n-$C_3H_7$ | 2-fluoro-phenyl | |
| 1.049 | 6-Cl | H | $C_2H_5$ | $C_2H_5$ | $CH_3$ | n-$C_3H_7$ | n-$C_7H_{15}$ | |
| 1.050 | 6-Cl | H | $C_2H_5$ | $CH_3$ | $C_2H_5$ | $CH_3$ | $CH_3$ | |
| 1.051 | 6-Cl | H | $C_2H_5$ | $CH_3$ | n-$C_3H_7$ | $CH_3$ | $CH_3$ | |
| 1.052 | 6-Cl | H | $C_2H_5$ | $CH_3$ | s-$C_4H_9$ | $CH_3$ | $CH_3$ | |
| 1.053 | 6-Cl | H | $C_2H_5$ | $CH_3$ | n-$C_6H_{13}$ | H | $CH_3$ | |
| 1.054 | 6-Cl | H | $C_2H_5$ | $CH_3$ | H | H | $C(CH_3)_2C_3H_7$-n | m.p. 73-74° C. |
| 1.055 | 6-Cl | H | $C_2H_5$ | $CH_3$ | H | H | $C(CH_3)_2C_3H_7$-n | m.p. 92-93° C. |
| 1.056 | 6-Cl | H | $C_2H_5$ | $CH_3$ | H | H | $C(CH_3)_2C_2H_5$ | m.p. 79-80° C. |
| 1.057 | 6-Cl | H | $C_2H_5$ | $CH_3$ | H | H | n-$C_6H_{13}$ | m.p. 84-85° C. |
| 1.058 | 6-Cl | H | $C_2H_5$ | $CH_3$ | H | H | n-$C_{10}H_{21}$ | resin |
| 1.059 | 6-Cl | H | $C_2H_5$ | $CH_3$ | H | H | $CH(CH_3)C_3H_7$n | m.p. 73-74° C. |
| 1.060 | 6-Cl | H | $C_2H_5$ | $CH_3$ | H | H | n-$C_5H_{11}$ | oil |
| 1.061 | 6-Cl | H | $C_2H_5$ | $CH_3$ | H | H | n-$C_8H_{17}$ | m.p. 53-55° C. |
| 1.062 | 6-Cl | H | $C_2H_5$ | $CH_3$ | H | H | n-$C_4H_9$ | oil |
| 1.063 | 6-Cl | H | $C_2H_5$ | $CH_3$ | H | H | 1-phenyl-1-cyclo-pentyl | m.p. 101-103° C. |
| 1.064 | 6-Cl | H | $C_2H_5$ | $CH_3$ | H | H | 1-phenyl-1-cyclo-propyl | glass |
| 1.065 | 6-Cl | H | $C_2H_5$ | $CH_3$ | H | H | 1-phenyl-1-cyclo-hexyl | m.p. 110-112° C. |
| 1.066 | 6-Cl | H | $C_2H_5$ | $CH_3$ | H | H | $C(CH_3)_2$phenyl | m.p. 104-105° C. |
| 1.067 | 6-Cl | H | $C_2H_5$ | $CH_3$ | H | H | 2,6-dimethylphenyl | m.p. 108-111° C. |
| 1.068 | 6-Cl | H | $C_2H_5$ | $CH_3$ | H | H | 2,4,6-tri-isopropyl-phenyl | m.p. 118-119° C. |
| 1.069 | 6-Cl | H | $C_2H_5$ | $CH_3$ | H | H | cyclohexyl | m.p. 94-96° C. |
| 1.070 | 6-Cl | H | $C_2H_5$ | $CH_3$ | H | H | benzyl | glass |
| 1.071 | 6-Cl | H | $C_2H_5$ | $CH_3$ | H | H | 1-adamantyl | m.p. 158-160° C. |
| 1.072 | 6-Cl | H | $C_2H_5$ | $CH_3$ | H | H | t-$C_4H_9$ | m.p. 136-137° C. |
| 1.073 | 6-Cl | H | $C_2H_5$ | $CH_3$ | H | H | $CH(phenyl)_2$ | glass |
| 1.074 | 6-Cl | H | $C_2H_5$ | $CH_3$ | H | H | cyclopropyl | m.p. 112-113° C. |
| 1.075 | 6-Cl | H | $C_2H_5$ | $CH_3$ | H | H | $CH(C_2H_5)_2$ | m.p. 69-70° C. |
| 1.076 | 6-Cl | H | $C_2H_5$ | $CH_3$ | H | H | $CH(n-C_3H_7)_2$ | m.p. 81-82° C. |
| 1.077 | 6-Cl | H | $C_2H_5$ | $CH_3$ | H | H | $CH_2$(cyclohexyl) | m.p. 71-73° C. |
| 1.078 | 6-Cl | H | $C_2H_5$ | $CH_3$ | H | H | $CH_2CH_2$(cyclo-hexyl) | m.p. 91-93° C. |
| 1.079 | 6-Cl | H | $C_2H_5$ | $CH_3$ | H | H | 3-(t-$C_4H_9$)cyclo-hex-1-yl | m.p. 107-110° C. |
| 1.080 | 6-Cl | H | $C_2H_5$ | $CH_3$ | H | H | 1-(4-chloro-phenyl)-1-cyclopentyl | m.p. 125-126° C. |
| 1.081 | 6-Cl | H | $C_2H_5$ | $CH_3$ | H | H | 1-(4-fluoro-phenyl)-1-cyclopentyl | m.p. 105-107° C. |
| 1.082 | 6-Cl | H | $C_2H_5$ | $CH_3$ | H | H | $CH_2C(CH_3)_2CH_3$ | m.p. 107-108° C. |
| 1.083 | 6-Cl | H | $C_2H_5$ | $CH_3$ | H | H | $CH_2CH(phenyl)_2$ | m.p. 91-93° C. |
| 1.084 | 6-Cl | H | $C_2H_5$ | $CH_3$ | H | H | 1-methyl-2,2-di-chloro-1-cyclopropyl | m.p. 80-82° C. |
| 1.085 | 6-Cl | H | $C_2H_5$ | $CH_3$ | H | H | 1-methyl-1-cyclohexyl | m.p. 95-96° C. |
| 1.086 | 6-Cl | H | $C_2H_5$ | $CH_3$ | H | H | cyclopentyl | m.p. 134-135° C. |
| 1.087 | 6-Cl | H | $C_2H_5$ | $CH_3$ | $CH_3$ | $CH_3$ | 4-Cl-phenyl | glass |
| 1.088 | 6-Cl | H | $CH_3$ | $CH_3$ | $CH_3$ | $CH_3$ | $CH_3$ | |
| 1.089 | 6-Cl | 5-Cl | $CH_3$ | $CH_3$ | H | H | $CH_3$ | |
| 1.090 | 6-Cl | H | $CH_3$ | $CH_3$ | H | H | $CH_3$ | |
| 1.091 | 6-Cl | H | $CH_3$ | $CH_3$ | $CH_3$ | H | $CH_3$ | |
| 1.092 | 6-Cl | H | $CH_3$ | $CH_3$ | H | H | $C_2H_5$ | |

TABLE 1-continued

Compounds of formula (Xa)

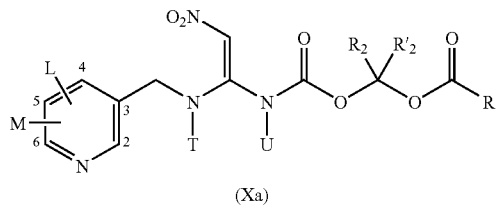

(Xa)

| No. | M | L | T | U | $R_2$ | $R'_2$ | R | Physical Data |
|---|---|---|---|---|---|---|---|---|
| 1.093 | 6-Cl | H | $CH_3$ | $CH_3$ | H | H | i-$C_3H_7$ | |
| 1.094 | 6-Cl | H | $CH_3$ | $CH_3$ | H | H | n-$C_3H_7$ | |
| 1.095 | 6-Cl | H | $CH_3$ | $CH_3$ | H | H | n-$C_4H_9$ | |
| 1.096 | 6-Cl | H | $CH_3$ | $CH_3$ | H | H | s-$C_4H_9$ | |
| 1.097 | H | 5-Cl | $CH_3$ | $CH_3$ | H | H | t-$C_4H_9$ | |
| 1.098 | 6-Cl | H | $CH_3$ | $CH_3$ | H | H | n-$C_7H_{15}$ | |
| 1.099 | 6-Cl | H | $CH_3$ | $CH_3$ | H | H | n-$C_{11}H_{23}$ | |
| 1.100 | 6-Cl | H | $CH_3$ | $CH_3$ | H | H | n-$C_{13}H_{27}$ | |
| 1.101 | 6-Cl | H | $CH_3$ | $CH_3$ | H | H | n-$C_{15}H_{31}$ | |
| 1.102 | 6-Cl | H | $CH_3$ | $CH_3$ | H | H | n-$C_{17}H_{35}$ | |
| 1.103 | 6-Cl | 5-Cl | $CH_3$ | $CH_3$ | H | H | n-$C_{11}H_{23}$ | |
| 1.104 | 6-Cl | 5-F | $CH_3$ | $CH_3$ | $CH_3$ | $CH_3$ | n-$C_7H_{15}$ | |
| 1.105 | 6-Cl | H | $CH_3$ | $CH_3$ | H | H | phenyl | |
| 1.106 | 6-Cl | H | $CH_3$ | $CH_3$ | H | H | n-$C_5H_{11}$ | |
| 1.107 | 6-Cl | H | $CH_3$ | $CH_3$ | H | H | biphenyl | |
| 1.108 | 6-Cl | H | $CH_3$ | $CH_3$ | H | H | phenoxyphenyl | |
| 1.109 | 6-Cl | H | $CH_3$ | $CH_3$ | H | H | 4-t-butyl-phenyl | |
| 1.110 | 6-Cl | H | $CH_3$ | $CH_3$ | H | H | 2-chloro-phenyl | |
| 1.111 | 6-Cl | H | $CH_3$ | $CH_3$ | H | H | 2,6-difluoro-phenyl | |
| 1.112 | 6-Cl | H | $CH_3$ | $CH_3$ | H | H | $C(CH_3)_2C_3H_7$-n | |
| 1.113 | 6-Cl | H | $CH_3$ | $CH_3$ | H | H | $C(CH_3)_2C_3H_7$-n | |
| 1.114 | 6-Cl | H | $CH_3$ | $CH_3$ | H | H | $C(CH_3)_2C_2H_5$ | |
| 1.115 | 6-Cl | H | $CH_3$ | $CH_3$ | H | H | n-$C_6H_{13}$ | |
| 1.116 | 6-Cl | H | $CH_3$ | $CH_3$ | H | H | n-$C_{10}H_{21}$ | |
| 1.117 | 6-Cl | H | $CH_3$ | $CH_3$ | H | H | $CH(CH_3)C_3H_7$n | |
| 1.118 | 6-Cl | H | $CH_3$ | $CH_3$ | H | H | n-$C_5H_{11}$ | |
| 1.119 | 6-Cl | H | $CH_3$ | $CH_3$ | H | H | n-$C_8H_{17}$ | |
| 1.120 | 6-Cl | H | $CH_3$ | $CH_3$ | H | H | n-$C_4H_9$ | |
| 1.121 | 6-Cl | H | $CH_3$ | $CH_3$ | H | H | 1-phenyl-1-cyclo-pentyl | |
| 1.122 | 6-Cl | H | $CH_3$ | $CH_3$ | H | H | 1-phenyl-1-cyclo-propyl | |
| 1.123 | 6-Cl | H | $CH_3$ | $CH_3$ | H | H | 1-phenyl-1-cyclo-hexyl | |
| 1.124 | 6-Cl | H | $CH_3$ | $CH_3$ | H | H | $C(CH_3)_2$phenyl | |
| 1.125 | 6-Cl | H | $CH_3$ | $CH_3$ | H | H | 2,6-dimethylphenyl | |
| 1.126 | 6-Cl | H | $CH_3$ | $CH_3$ | H | H | 2,4,6-tri-isopropyl-phenyl | |
| 1.127 | 6-Cl | H | $CH_3$ | $CH_3$ | H | H | cyclohexyl | |
| 1.128 | 6-Cl | H | $CH_3$ | $CH_3$ | H | H | benzyl | |
| 1.129 | 6-Cl | H | $CH_3$ | $CH_3$ | H | H | 1-adamantyl | |
| 1.130 | 6-Cl | H | $CH_3$ | $CH_3$ | H | H | t-$C_4H_9$ | |
| 1.131 | 6-Cl | H | $CH_3$ | $CH_3$ | H | H | $CH(phenyl)_2$ | |
| 1.132 | 6-Cl | H | $CH_3$ | $CH_3$ | H | H | cyclopropyl | |
| 1.133 | 6-Cl | H | $CH_3$ | $CH_3$ | H | H | $CH(C_2H_5)_2$ | |
| 1.134 | 6-Cl | H | $CH_3$ | $CH_3$ | H | H | $CH(n-C_3H_7)_2$ | |
| 1.135 | 6-Cl | H | $CH_3$ | $CH_3$ | H | H | $CH_2$(cyclohexyl) | |
| 1.136 | 6-Cl | H | $CH_3$ | $CH_3$ | H | H | $CH_2CH_2$(cyclo-hexyl) | |
| 1.137 | 6-Cl | H | $CH_3$ | $CH_3$ | H | H | 3-(t-$C_4H_9$)cyclo-hex-1-yl | |
| 1.138 | 6-Cl | H | $CH_3$ | $CH_3$ | H | H | 1-(4-chloro-phenyl)-1-cyclopentyl | |
| 1.139 | 6-Cl | H | $CH_3$ | $CH_3$ | H | H | 1-(4-fluoro-phenyl)-1-cyclopentyl | |
| 1.140 | 6-Cl | H | $CH_3$ | $CH_3$ | H | H | $CH_2C(CH_3)_2CH_3$ | |
| 1.141 | 6-Cl | H | $CH_3$ | $CH_3$ | H | H | $CH_2CH(phenyl)_2$ | |
| 1.142 | 6-Cl | H | $CH_3$ | $CH_3$ | H | H | 1-methyl-2,2-di-chloro-1-cyclopropyl | |
| 1.143 | 6-Cl | H | $CH_3$ | $CH_3$ | H | H | 1-methyl-1-cyclohexyl | |
| 1.144 | 6-Cl | H | $CH_3$ | $CH_3$ | H | H | cyclopentyl | |
| 1.145 | 6-Cl | H | $CH_3$ | $CH_3$ | $CH_3$ | $CH_3$ | 4-Cl-phenyl | |
| 1.146 | 6-Cl | H | $C_2H_5$ | $C_2H_5$ | $CH_3$ | $CH_3$ | $CH_3$ | |
| 1.147 | 6-Cl | 5-Cl | $C_2H_5$ | $C_2H_5$ | H | H | $CH_3$ | |
| 1.148 | 6-Cl | H | $C_2H_5$ | $C_2H_5$ | H | H | $CH_3$ | |

TABLE 1-continued

Compounds of formula (Xa)

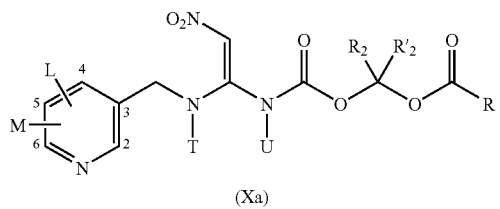

(Xa)

| No. | M | L | T | U | $R_2$ | $R'_2$ | R | Physical Data |
|---|---|---|---|---|---|---|---|---|
| 1.149 | 6-Cl | H | $C_2H_5$ | $C_2H_5$ | $CH_3$ | $C_2H_5$ | $CH_3$ | |
| 1.150 | 6-Cl | H | $C_2H_5$ | $C_2H_5$ | H | H | $C_2H_5$ | |
| 1.151 | 6-Cl | H | $C_2H_5$ | $C_2H_5$ | H | H | i-$C_3H_7$ | |
| 1.152 | 6-Cl | H | $C_2H_5$ | $C_2H_5$ | H | H | n-$C_3H_7$ | |
| 1.153 | 6-Cl | H | $C_2H_5$ | $C_2H_5$ | H | H | n-$C_4H_9$ | |
| 1.154 | 6-Cl | H | $C_2H_5$ | $C_2H_5$ | H | H | s-$C_4H_9$ | |
| 1.155 | H | 5-Cl | $C_2H_5$ | $C_2H_5$ | H | H | t-$C_4H_9$ | |
| 1.156 | 6-Cl | H | $C_2H_5$ | $C_2H_5$ | H | H | n-$C_7H_{15}$ | |
| 1.157 | 6-Cl | H | $C_2H_5$ | $C_2H_5$ | H | H | n-$C_{11}H_{23}$ | |
| 1.158 | 6-Cl | H | $C_2H_5$ | $C_2H_5$ | H | H | n-$C_{13}H_{27}$ | |
| 1.159 | 6-Cl | H | $C_2H_5$ | $C_2H_5$ | H | H | n-$C_{15}H_{31}$ | |
| 1.160 | 6-Cl | H | $C_2H_5$ | $C_2H_5$ | H | H | n-$C_{17}H_{35}$ | |
| 1.161 | 6-Cl | 5-Cl | $C_2H_5$ | $C_2H_5$ | H | H | n-$C_{11}H_{23}$ | |
| 1.162 | 6-Cl | 5-F | $C_2H_5$ | $C_2H_5$ | $CH_3$ | $CH_3$ | n-$C_7H_{15}$ | |
| 1.163 | 6-Cl | H | $C_2H_5$ | $C_2H_5$ | H | H | phenyl | |
| 1.164 | 6-Cl | H | $C_2H_5$ | $C_2H_5$ | H | H | n-$C_5H_{11}$ | |
| 1.165 | 6-Cl | H | $C_2H_5$ | $C_2H_5$ | H | H | biphenyl | |
| 1.166 | 6-Cl | H | $C_2H_5$ | $C_2H_5$ | H | H | phenoxyphenyl | |
| 1.167 | 6-Cl | H | $C_2H_5$ | $C_2H_5$ | H | H | 4-t-butyl-phenyl | |
| 1.168 | 6-Cl | H | $C_2H_5$ | $C_2H_5$ | H | H | 2-chloro-phenyl | |
| 1.169 | 6-Cl | H | $C_2H_5$ | $C_2H_5$ | H | H | 2,6-difluoro-phenyl | |
| 1.170 | 6-Cl | H | $C_2H_5$ | $C_2H_5$ | H | H | $C(CH_3)_2C_3H_7$-n | |
| 1.171 | 6-Cl | H | $C_2H_5$ | $C_2H_5$ | H | H | $C(CH_3)_2C_3H_7$-n | |
| 1.172 | 6-Cl | H | $C_2H_5$ | $C_2H_5$ | H | H | $C(CH_3)_2C_2H_5$ | |
| 1.173 | 6-Cl | H | $C_2H_5$ | $C_2H_5$ | H | H | n-$C_6H_{13}$ | |
| 1.174 | 6-Cl | H | $C_2H_5$ | $C_2H_5$ | H | H | n-$C_{10}H_{21}$ | |
| 1.175 | 6-Cl | H | $C_2H_5$ | $C_2H_5$ | H | H | $CH(CH_3)C_3H_7$n | |
| 1.176 | 6-Cl | H | $C_2H_5$ | $C_2H_5$ | H | H | n-$C_5H_{11}$ | |
| 1.177 | 6-Cl | H | $C_2H_5$ | $C_2H_5$ | H | H | n-$C_8H_{17}$ | |
| 1.178 | 6-Cl | H | $C_2H_5$ | $C_2H_5$ | H | H | n-$C_4H_9$ | |
| 1.179 | 6-Cl | H | $C_2H_5$ | $C_2H_5$ | H | H | 1-phenyl-1-cyclo-pentyl | |
| 1.180 | 6-Cl | H | $C_2H_5$ | $C_2H_5$ | H | H | 1-phenyl-1-cyclo-propyl | |
| 1.191 | 6-Cl | H | $C_2H_5$ | $C_2H_5$ | H | H | 1-phenyl-1-cyclo-hexyl | |
| 1.192 | 6-Cl | H | $C_2H_5$ | $C_2H_5$ | H | H | $C(CH_3)_2$phenyl | |
| 1.193 | 6-Cl | H | $C_2H_5$ | $C_2H_5$ | H | H | 2,6-dimethylphenyl | |
| 1.194 | 6-Cl | H | $C_2H_5$ | $C_2H_5$ | H | H | 2,4,6-tri-isopropyl-phenyl | |
| 1.195 | 6-Cl | H | $C_2H_5$ | $C_2H_5$ | H | H | cyclohexyl | |
| 1.196 | 6-Cl | H | $C_2H_5$ | $C_2H_5$ | H | H | benzyl | |
| 1.197 | 6-Cl | H | $C_2H_5$ | $C_2H_5$ | H | H | 1-adamantyl | |
| 1.198 | 6-Cl | H | $C_2H_5$ | $C_2H_5$ | H | H | t-$C_4H_9$ | |
| 1.199 | 6-Cl | H | $C_2H_5$ | $C_2H_5$ | H | H | $CH(phenyl)_2$ | |
| 1.200 | 6-Cl | H | $C_2H_5$ | $C_2H_5$ | H | H | cyclopropyl | |
| 1.201 | 6-Cl | H | $C_2H_5$ | $C_2H_5$ | H | H | $CH(C_2H_5)_2$ | |
| 1.202 | 6-Cl | H | $C_2H_5$ | $C_2H_5$ | H | H | $CH(n-C_3H_7)_2$ | |
| 1.203 | 6-Cl | H | $C_2H_5$ | $C_2H_5$ | H | H | $CH_2(cyclohexyl)$ | |
| 1.204 | 6-Cl | H | $C_2H_5$ | $C_2H_5$ | H | H | $CH_3CH_2(cyclo-hexyl)$ | |
| 1.205 | 6-Cl | H | $C_2H_5$ | $C_2H_5$ | H | H | 3-(t-$C_4H_9$)cyclo-hex-1-yl | |
| 1.206 | 6-Cl | H | $C_2H_5$ | $C_2H_5$ | H | H | 1-(4-chloro-phenyl)-1-cyclopentyl | |
| 1.207 | 6-Cl | H | $C_2H_5$ | $C_2H_5$ | H | H | 1-(4-fluoro-phenyl)-1-cyclopentyl | |
| 1.208 | 6-Cl | H | $C_2H_5$ | $C_2H_5$ | H | H | $CH_2C(CH_3)_2CH_3$ | |
| 1.209 | 6-Cl | H | $C_2H_5$ | $C_2H_5$ | H | H | $CH_2CH(phenyl)_2$ | |
| 1.210 | 6-Cl | H | $C_2H_5$ | $C_2H_5$ | H | H | 1-methyl-2,2-di-chloro-1-cyclopropyl | |
| 1.211 | 6-Cl | H | $C_2H_5$ | $C_2H_5$ | H | H | 1-methyl-1-cyclohexyl | |
| 1.212 | 6-Cl | H | $C_2H_5$ | $C_2H_5$ | H | H | cyclopentyl | |
| 1.213 | 6-Cl | H | $C_2H_5$ | $C_2H_5$ | $CH_3$ | $CH_3$ | 4-Cl-phenyl | |

TABLE 2

Compounds of formula (Xb)

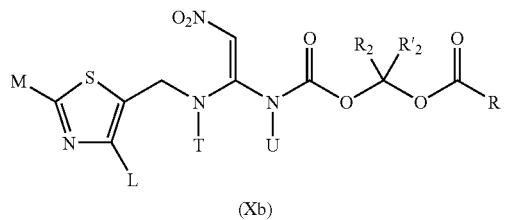

(Xb)

| No. | L | M | T | U | R$_2$ | R'$_2$ | R |
|---|---|---|---|---|---|---|---|
| 2.001 | H | Cl | C$_2$H$_5$ | CH$_3$ | H | H | CH$_3$ |
| 2.002 | Cl | Cl | C$_2$H$_5$ | CH$_3$ | H | H | CH$_3$ |
| 2.003 | H | F | CH$_3$ | CH$_3$ | H | H | CH$_3$ |
| 2.004 | H | Cl | C$_2$H$_5$ | CH$_3$ | CH$_3$ | H | CH$_3$ |
| 2.005 | F | Cl | C$_2$H$_5$ | CH$_3$ | H | H | C$_2$H$_5$ |
| 2.006 | H | Cl | C$_2$H$_5$ | CH$_3$ | H | H | i-C$_3$H$_7$ |
| 2.007 | H | Cl | C$_2$H$_5$ | CH$_3$ | H | H | n-C$_3$H$_7$ |
| 2.008 | H | Cl | C$_2$H$_5$ | CH$_3$ | H | H | n-C$_4$H$_9$ |
| 2.009 | H | Cl | H | CH$_3$ | H | H | s-C$_4$H$_9$ |
| 2.010 | H | Cl | C$_2$H$_5$ | CH$_3$ | H | H | t-C$_4$H$_9$ |
| 2.011 | H | Cl | C$_2$H$_5$ | CH$_3$ | H | H | n-C$_7$H$_{15}$ |
| 2.012 | H | Cl | C$_2$H$_5$ | CH$_3$ | H | H | n-C$_{11}$H$_{23}$ |
| 2.013 | H | Cl | C$_2$H$_5$ | CH$_3$ | H | H | n-C$_{13}$H$_{27}$ |
| 2.014 | H | Cl | C$_2$H$_5$ | CH$_3$ | H | H | n-C$_{15}$H$_{31}$ |
| 2.015 | H | Cl | C$_2$H$_5$ | CH$_3$ | H | H | n-C$_{17}$H$_{35}$ |
| 2.016 | Cl | Cl | C$_2$H$_5$ | CH$_3$ | H | H | n-C$_{11}$H$_{23}$ |
| 2.017 | Cl | F | CH$_3$ | CH$_3$ | H | H | n-C$_7$H$_{15}$ |
| 2.018 | H | Cl | C$_2$H$_5$ | CH$_3$ | H | H | phenyl |
| 2.019 | H | Cl | C$_2$H$_5$ | CH$_3$ | H | CH$_3$ | phenyl |
| 2.020 | H | Cl | C$_2$H$_5$ | CH$_3$ | H | H | biphenyl |
| 2.021 | H | Cl | C$_2$H$_5$ | CH$_3$ | H | H | phenoxyphenyl |
| 2.022 | H | Cl | C$_2$H$_5$ | CH$_3$ | H | H | 4-t-butyl-phenyl |
| 2.023 | H | Cl | C$_2$H$_5$ | CH$_3$ | H | H | 2-chloro-phenyl |
| 2.024 | H | Cl | C$_2$H$_5$ | CH$_3$ | H | H | 2,6-difluoro-phenyl |
| 2.025 | H | H | C$_2$H$_5$ | H | H | H | n-C$_{17}$H$_{35}$ |
| 2.026 | H | H | C$_2$H$_5$ | C$_2$H$_5$ | CH$_3$ | H | n-C$_7$H$_{15}$ |
| 2.027 | H | Cl | C$_2$H$_5$ | CH$_3$ | C$_2$H$_5$ | H | CH$_3$ |
| 2.028 | H | Cl | C$_2$H$_5$ | CH$_3$ | n-C$_3$H$_7$ | H | CH$_3$ |
| 2.029 | H | Cl | C$_2$H$_5$ | CH$_3$ | s-C$_4$H$_9$ | H | CH$_3$ |
| 2.030 | H | Cl | C$_2$H$_5$ | CH$_3$ | n-C$_6$H$_{13}$ | H | CH$_3$ |
| 2.031 | H | Cl | CH$_3$ | CH$_3$ | CH$_3$ | H | CH$_3$ |
| 2.032 | H | F | CH$_3$ | CH$_3$ | CH$_3$ | H | CH$_3$ |
| 2.033 | H | Cl | C$_2$H$_5$ | CH$_3$ | H | H | cyclohexyl |
| 2.034 | H | Cl | C$_2$H$_5$ | CH$_3$ | H | H | vinyl |
| 2.035 | H | Cl | C$_2$H$_5$ | CH$_3$ | H | H | allyl |
| 2.036 | H | Cl | C$_2$H$_5$ | CH$_3$ | H | H | 2-propargyl |
| 2.037 | H | Cl | C$_2$H$_5$ | CH$_3$ | H | H | C(CH$_3$)$_2$C$_3$H$_7$-n |
| 2.038 | H | Cl | C$_2$H$_5$ | CH$_3$ | H | H | C(CH$_3$)$_2$C$_3$H$_7$-n |
| 2.039 | H | Cl | C$_2$H$_5$ | CH$_3$ | H | H | C(CH$_3$)$_2$C$_2$H$_5$ |
| 2.040 | H | Cl | C$_2$H$_5$ | CH$_3$ | H | H | n-C$_6$H$_{13}$ |
| 2.041 | H | Cl | C$_2$H$_5$ | CH$_3$ | H | H | n-C$_{10}$H$_{21}$ |
| 2.042 | H | Cl | C$_2$H$_5$ | CH$_3$ | H | H | CH(CH$_3$)C$_3$H$_7$n |
| 2.043 | H | Cl | C$_2$H$_5$ | CH$_3$ | H | H | n-C$_5$H$_{11}$ |
| 2.044 | H | Cl | C$_2$H$_5$ | CH$_3$ | H | H | n-C$_8$H$_{17}$ |
| 2.045 | H | Cl | C$_2$H$_5$ | CH$_3$ | H | H | n-C$_4$H$_9$ |
| 2.046 | H | Cl | C$_2$H$_5$ | CH$_3$ | H | H | 1-phenyl-1-cyclo-pentyl |
| 2.047 | H | Cl | C$_2$H$_5$ | CH$_3$ | H | H | 1-phenyl-1-cyclo-propyl |
| 2.048 | H | Cl | C$_2$H$_5$ | CH$_3$ | H | H | 1-phenyl-1-cyclo-hexyl |
| 2.049 | 2.0H | Cl | C$_2$H$_5$ | CH$_3$ | H | H | C(CH$_3$)$_2$phenyl |
| 2.050 | H | Cl | C$_2$H$_5$ | CH$_3$ | H | H | 2,6-dimethylphenyl |
| 2.051 | H | Cl | C$_2$H$_5$ | CH$_3$ | H | H | 2,4,6-tri-isopropyl-phenyl |
| 2.052 | H | Cl | C$_2$H$_5$ | CH$_3$ | H | H | cyclohexyl |
| 2.053 | H | Cl | C$_2$H$_5$ | CH$_3$ | H | H | benzyl |
| 2.054 | H | Cl | C$_2$H$_5$ | CH$_3$ | H | H | 1-adamantyl |
| 2.055 | H | Cl | C$_2$H$_5$ | CH$_3$ | H | H | t-C$_4$H$_9$ |
| 2.056 | H | Cl | C$_2$H$_5$ | CH$_3$ | H | H | CH(phenyl)$_2$ |
| 2.057 | H | Cl | C$_2$H$_5$ | CH$_3$ | H | H | cyclopropyl |
| 2.058 | H | Cl | C$_2$H$_5$ | CH$_3$ | H | H | CH(C$_2$H$_5$)$_2$ |
| 2.059 | H | Cl | C$_2$H$_5$ | CH$_3$ | H | H | CH(n-C$_3$H$_7$)$_2$ |
| 2.060 | H | Cl | C$_2$H$_5$ | CH$_3$ | H | H | CH$_2$(cyclohexyl) |
| 2.061 | H | Cl | C$_2$H$_5$ | CH$_3$ | H | H | CH$_2$CH$_2$(cyclo-hexyl) |
| 2.062 | H | Cl | C$_2$H$_5$ | CH$_3$ | H | H | 3-(t-C$_4$H$_9$)cyclo-hex-1-yl |

TABLE 2-continued

Compounds of formula (Xb)

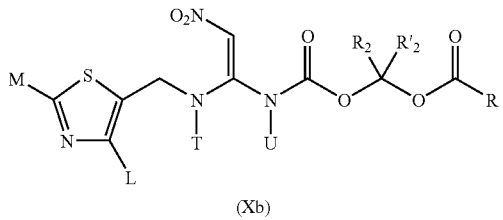

(Xb)

| No. | L | M | T | U | $R_2$ | $R'_2$ | R |
|---|---|---|---|---|---|---|---|
| 2.063 | H | Cl | $C_2H_5$ | $CH_3$ | H | H | 1-(4-chloro-phenyl)-1-cyclopentyl |
| 2.064 | H | Cl | $C_2H_5$ | $CH_3$ | H | H | 1-(4-fluoro-phenyl)-1-cyclopentyl |
| 2.065 | H | Cl | $C_2H_5$ | $CH_3$ | H | H | $CH_2C(CH_3)_2CH_3$ |
| 2.066 | H | Cl | $C_2H_5$ | $CH_3$ | H | H | $CH_2CH(phenyl)_2$ |
| 2.067 | H | Cl | $C_2H_5$ | $CH_3$ | H | H | 1-methyl-2,2-di-chloro-1-cyclopropyl |
| 2.068 | H | Cl | $C_2H_5$ | $CH_3$ | H | H | 1-methyl-1-cyclohexyl |
| 2.069 | H | Cl | $C_2H_5$ | $CH_3$ | H | H | cyclopentyl |
| 2.070 | H | Cl | $C_2H_5$ | $CH_3$ | $CH_3$ | $CH_3$ | 4-Cl-phenyl |
| 2.071 | 6-Cl | H | $CH_3$ | $CH_3$ | $CH_3$ | $CH_3$ | $CH_3$ |
| 2.073 | 6-Cl | 5-Cl | $CH_3$ | $CH_3$ | H | H | $CH_3$ |
| 2.074 | 6-Cl | H | $CH_3$ | $CH_3$ | H | H | $CH_3$ |
| 2.075 | 6-Cl | H | $CH_3$ | $CH_3$ | $CH_3$ | H | $CH_3$ |
| 2.076 | 6-Cl | H | $CH_3$ | $CH_3$ | H | H | $C_2H_5$ |
| 2.077 | 6-Cl | H | $CH_3$ | $CH_3$ | H | H | $i-C_3H_7$ |
| 2.078 | 6-Cl | H | $CH_3$ | $CH_3$ | H | H | $n-C_3H_7$ |
| 2.079 | 6-Cl | H | $CH_3$ | $CH_3$ | H | H | $n-C_4H_9$ |
| 2.080 | 6-Cl | H | $CH_3$ | $CH_3$ | H | H | $s-C_4H_9$ |
| 2.081 | H | 5-Cl | $CH_3$ | $CH_3$ | H | H | $t-C_4H_9$ |
| 2.082 | 6-Cl | H | $CH_3$ | $CH_3$ | H | H | $n-C_7H_{15}$ |
| 2.083 | 6-Cl | H | $CH_3$ | $CH_3$ | H | H | $n-C_{11}H_{23}$ |
| 2.084 | 6-Cl | H | $CH_3$ | $CH_3$ | H | H | $n-C_{13}H_{27}$ |
| 2.085 | 6-Cl | H | $CH_3$ | $CH_3$ | H | H | $n-C_{15}H_{31}$ |
| 2.086 | 6-Cl | H | $CH_3$ | $CH_3$ | H | H | $n-C_{17}H_{35}$ |
| 2.087 | 6-Cl | 5-Cl | $CH_3$ | $CH_3$ | H | H | $n-C_{11}H_{23}$ |
| 2.088 | 6-Cl | 5-F | $CH_3$ | $CH_3$ | $CH_3$ | $CH_3$ | $n-C_7H_{15}$ |
| 2.089 | 6-Cl | H | $CH_3$ | $CH_3$ | H | H | phenyl |
| 2.090 | 6-Cl | H | $CH_3$ | $CH_3$ | H | H | $n-C_5H_{11}$ |
| 2.091 | 6-Cl | H | $CH_3$ | $CH_3$ | H | H | biphenyl |
| 2.092 | 6-Cl | H | $CH_3$ | $CH_3$ | H | H | phenoxyphenyl |
| 2.093 | 6-Cl | H | $CH_3$ | $CH_3$ | H | H | 4-t-butyl-phenyl |
| 2.094 | 6-Cl | H | $CH_3$ | $CH_3$ | H | H | 2-chloro-phenyl |
| 2.095 | 6-Cl | H | $CH_3$ | $CH_3$ | H | H | 2,6-difluoro-phenyl |
| 2.096 | 6-Cl | H | $CH_3$ | $CH_3$ | H | H | $C(CH_3)_2C_3H_7-n$ |
| 2.097 | 6-Cl | H | $CH_3$ | $CH_3$ | H | H | $C(CH_3)_2C_3H_7-n$ |
| 2.098 | 6-Cl | H | $CH_3$ | $CH_3$ | H | H | $C(CH_3)_2C_2H_5$ |
| 2.099 | 6-Cl | H | $CH_3$ | $CH_3$ | H | H | $n-C_6H_{13}$ |
| 2.100 | 6-Cl | H | $CH_3$ | $CH_3$ | H | H | $n-C_{10}H_{21}$ |
| 2.101 | 6-Cl | H | $CH_3$ | $CH_3$ | H | H | $CH(CH_3)C_3H_7n$ |
| 2.102 | 6-Cl | H | $CH_3$ | $CH_3$ | H | H | $n-C_5H_{11}$ |
| 2.103 | 6-Cl | H | $CH_3$ | $CH_3$ | H | H | $n-C_8H_{17}$ |
| 2.104 | 6-Cl | H | $CH_3$ | $CH_3$ | H | H | $n-C_4H_9$ |
| 2.105 | 6-Cl | H | $CH_3$ | $CH_3$ | H | H | 1-phenyl-1-cyclo-pentyl |
| 2.106 | 6-Cl | H | $CH_3$ | $CH_3$ | H | H | 1-phenyl-1-cyclo-propyl |
| 2.107 | 6-Cl | H | $CH_3$ | $CH_3$ | H | H | 1-phenyl-1-cyclo-hexyl |
| 2.108 | 6-Cl | H | $CH_3$ | $CH_3$ | H | H | $C(CH_3)_2phenyl$ |
| 2.109 | 6-Cl | H | $CH_3$ | $CH_3$ | H | H | 2,6-dimethylphenyl |
| 2.110 | 6-Cl | H | $CH_3$ | $CH_3$ | H | H | 2,4,6-tri-isopropyl-phenyl |
| 2.111 | 6-Cl | H | $CH_3$ | $CH_3$ | H | H | cyclohexyl |
| 2.112 | 6-Cl | H | $CH_3$ | $CH_3$ | H | H | benzyl |
| 2.113 | 6-Cl | H | $CH_3$ | $CH_3$ | H | H | 1-adamantyl |
| 2.114 | 6-Cl | H | $CH_3$ | $CH_3$ | H | H | $t-C_4H_9$ |
| 2.115 | 6-Cl | H | $CH_3$ | $CH_3$ | H | H | $CH(phenyl)_2$ |
| 2.116 | 6-Cl | H | $CH_3$ | $CH_3$ | H | H | cyclopropyl |
| 2.117 | 6-Cl | H | $CH_3$ | $CH_3$ | H | H | $CH(C_2H_5)_2$ |
| 2.118 | 6-Cl | H | $CH_3$ | $CH_3$ | H | H | $CH(n-C_3H_7)_2$ |
| 2.119 | 6-Cl | H | $CH_3$ | $CH_3$ | H | H | $CH_2(cyclohexyl)$ |
| 2.120 | 6-Cl | H | $CH_3$ | $CH_3$ | H | H | $CH_2CH_2(cyclo-hexyl)$ |
| 2.121 | 6-Cl | H | $CH_3$ | $CH_3$ | H | H | $3-(t-C_4H_9)cyclo-hex-1-yl$ |

TABLE 2-continued

Compounds of formula (Xb)

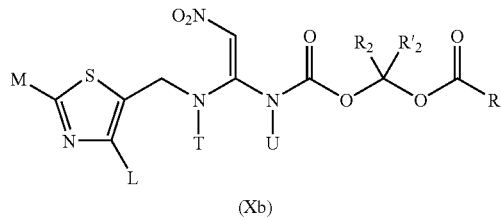

(Xb)

| No. | L | M | T | U | R$_2$ | R'$_2$ | R |
|---|---|---|---|---|---|---|---|
| 2.122 | 6-Cl | H | CH$_3$ | CH$_3$ | H | H | 1-(4-chloro-phenyl)-1-cyclopentyl |
| 2.123 | 6-Cl | H | CH$_3$ | CH$_3$ | H | H | 1-(4-fluoro-phenyl)-1-cyclopentyl |
| 2.124 | 6-Cl | H | CH$_3$ | CH$_3$ | H | H | CH$_2$C(CH$_3$)$_2$CH$_3$ |
| 2.125 | 6-Cl | H | CH$_3$ | CH$_3$ | H | H | CH$_2$CH(phenyl)$_2$ |
| 2.126 | 6-Cl | H | CH$_3$ | CH$_3$ | H | H | 1-methyl-2,2-di-chloro-1-cyclopropyl |
| 2.127 | 6-Cl | H | CH$_3$ | CH$_3$ | H | H | 1-methyl-1-cyclohexyl |
| 2.128 | 6-Cl | H | CH$_3$ | CH$_3$ | H | H | cyclopentyl |
| 2.129 | 6-Cl | H | CH$_3$ | CH$_3$ | CH$_3$ | CH$_3$ | 4-Cl-phenyl |
| 2.130 | 6-Cl | H | C$_2$H$_5$ | C$_2$H$_5$ | CH$_3$ | CH$_3$ | CH$_3$ |
| 2.131 | 6-Cl | 5-Cl | C$_2$H$_5$ | C$_2$H$_5$ | H | H | CH$_3$ |
| 2.132 | 6-Cl | H | C$_2$H$_5$ | C$_2$H$_5$ | H | H | CH$_3$ |
| 2.133 | 6-Cl | H | C$_2$H$_5$ | C$_2$H$_5$ | CH$_3$ | C$_2$H$_5$ | CH$_3$ |
| 2.134 | 6-Cl | H | C$_2$H$_5$ | C$_2$H$_5$ | H | H | C$_2$H$_5$ |
| 2.135 | 6-Cl | H | C$_2$H$_5$ | C$_2$H$_5$ | H | H | i-C$_3$H$_7$ |
| 2.136 | 6-Cl | H | C$_2$H$_5$ | C$_2$H$_5$ | H | H | n-C$_3$H$_7$ |
| 2.137 | 6-Cl | H | C$_2$H$_5$ | C$_2$H$_5$ | H | H | n-C$_4$H$_9$ |
| 2.138 | 6-Cl | H | C$_2$H$_5$ | C$_2$H$_5$ | H | H | s-C$_4$H$_9$ |
| 2.139 | H | 5-Cl | C$_2$H$_5$ | C$_2$H$_5$ | H | H | t-C$_4$H$_9$ |
| 2.140 | 6-Cl | H | C$_2$H$_5$ | C$_2$H$_5$ | H | H | n-C$_7$H$_{15}$ |
| 2.141 | 6-Cl | H | C$_2$H$_5$ | C$_2$H$_5$ | H | H | n-C$_{11}$H$_{23}$ |
| 2.142 | 6-Cl | H | C$_2$H$_5$ | C$_2$H$_5$ | H | H | n-C$_{13}$H$_{27}$ |
| 2.143 | 6-Cl | H | C$_2$H$_5$ | C$_2$H$_5$ | H | H | n-C$_{15}$H$_{31}$ |
| 2.144 | 6-Cl | H | C$_2$H$_5$ | C$_2$H$_5$ | H | H | n-C$_{17}$H$_{35}$ |
| 2.145 | 6-Cl | 5-Cl | C$_2$H$_5$ | C$_2$H$_5$ | H | H | n-C$_{11}$H$_{23}$ |
| 2.146 | 6-Cl | 5-F | C$_2$H$_5$ | C$_2$H$_5$ | CH$_3$ | CH$_3$ | n-C$_7$H$_{15}$ |
| 2.147 | 6-Cl | H | C$_2$H$_5$ | C$_2$H$_5$ | H | H | phenyl |
| 2.148 | 6-Cl | H | C$_2$H$_5$ | C$_2$H$_5$ | H | H | n-C$_5$H$_{11}$ |
| 2.149 | 6-Cl | H | C$_2$H$_5$ | C$_2$H$_5$ | H | H | biphenyl |
| 2.150 | 6-Cl | H | C$_2$H$_5$ | C$_2$H$_5$ | H | H | phenoxyphenyl |
| 2.151 | 6-Cl | H | C$_2$H$_5$ | C$_2$H$_5$ | H | H | 4-t-butyl-phenyl |
| 2.152 | 6-Cl | H | C$_2$H$_5$ | C$_2$H$_5$ | H | H | 2-chloro-phenyl |
| 2.153 | 6-Cl | H | C$_2$H$_5$ | C$_2$H$_5$ | H | H | 2,6-difluoro-phenyl |
| 2.154 | 6-Cl | H | C$_2$H$_5$ | C$_2$H$_5$ | H | H | C(CH$_3$)$_2$C$_3$H$_7$-n |
| 2.155 | 6-Cl | H | C$_2$H$_5$ | C$_2$H$_5$ | H | H | C(CH$_3$)$_2$C$_3$H$_7$-n |
| 2.156 | 6-Cl | H | C$_2$H$_5$ | C$_2$H$_5$ | H | H | C(CH$_3$)$_2$C$_2$H$_5$ |
| 2.157 | 6-Cl | H | C$_2$H$_5$ | C$_2$H$_5$ | H | H | n-C$_6$H$_{13}$ |
| 2.158 | 6-Cl | H | C$_2$H$_5$ | C$_2$H$_5$ | H | H | n-C$_{10}$H$_{21}$ |
| 2.159 | 6-Cl | H | C$_2$H$_5$ | C$_2$H$_5$ | H | H | CH(CH$_3$)C$_3$H$_7$n |
| 2.160 | 6-Cl | H | C$_2$H$_5$ | C$_2$H$_5$ | H | H | n-C$_5$H$_{11}$ |
| 2.161 | 6-Cl | H | C$_2$H$_5$ | C$_2$H$_5$ | H | H | n-C$_8$H$_{17}$ |
| 2.162 | 6-Cl | H | C$_2$H$_5$ | C$_2$H$_5$ | H | H | n-C$_4$H$_9$ |
| 2.163 | 6-Cl | H | C$_2$H$_5$ | C$_2$H$_5$ | H | H | 1-phenyl-1-cyclo-pentyl |
| 2.164 | 6-Cl | H | C$_2$H$_5$ | C$_2$H$_5$ | H | H | 1-phenyl-1-cyclo-propyl |
| 2.165 | 6-Cl | H | C$_2$H$_5$ | C$_2$H$_5$ | H | H | 1-phenyl-1-cyclo-hexyl |
| 2.166 | 6-Cl | H | C$_2$H$_5$ | C$_2$H$_5$ | H | H | C(CH$_3$)$_2$phenyl |
| 2.167 | 6-Cl | H | C$_2$H$_5$ | C$_2$H$_5$ | H | H | 2,6-dimethylphenyl |
| 2.168 | 6-Cl | H | C$_2$H$_5$ | C$_2$H$_5$ | H | H | 2,4,6-tri-isopropyl-phenyl |
| 2.169 | 6-Cl | H | C$_2$H$_5$ | C$_2$H$_5$ | H | H | cyclohexyl |
| 2.170 | 6-Cl | H | C$_2$H$_5$ | C$_2$H$_5$ | H | H | benzyl |
| 2.171 | 6-Cl | H | C$_2$H$_5$ | C$_2$H$_5$ | H | H | 1-adamantyl |
| 2.172 | 6-Cl | H | C$_2$H$_5$ | C$_2$H$_5$ | H | H | t-C$_4$H$_9$ |
| 2.173 | 6-Cl | H | C$_2$H$_5$ | C$_2$H$_5$ | H | H | CH(phenyl)$_2$ |
| 2.174 | 6-Cl | H | C$_2$H$_5$ | C$_2$H$_5$ | H | H | cyclopropyl |
| 2.175 | 6-Cl | H | C$_2$H$_5$ | C$_2$H$_5$ | H | H | CH(C$_2$H$_5$)$_2$ |
| 2.176 | 6-Cl | H | C$_2$H$_5$ | C$_2$H$_5$ | H | H | CH(n-C$_3$H$_7$)$_2$ |
| 2.177 | 6-Cl | H | C$_2$H$_5$ | C$_2$H$_5$ | H | H | CH$_2$(cyclohexyl) |
| 2.178 | 6-Cl | H | C$_2$H$_5$ | C$_2$H$_5$ | H | H | CH$_2$CH$_2$(cyclo-hexyl) |
| 2.179 | 6-Cl | H | C$_2$H$_5$ | C$_2$H$_5$ | H | H | 3-(t-C$_4$H$_9$)cyclo-hex-1-yl |

TABLE 2-continued

Compounds of formula (Xb)

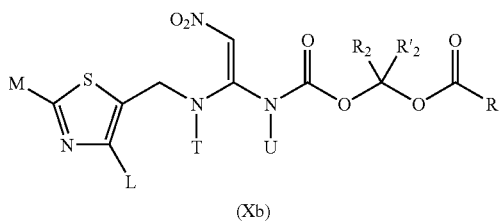

(Xb)

| No. | L | M | T | U | R₂ | R'₂ | R |
|---|---|---|---|---|---|---|---|
| 2.180 | 6-Cl | H | C₂H₅ | C₂H₅ | H | H | 1-(4-chloro-phenyl)-1-cyclopentyl |
| 2.181 | 6-Cl | H | C₂H₅ | C₂H₅ | H | H | 1-(4-fluoro-phenyl)-1-cyclopentyl |
| 2.182 | 6-Cl | H | C₂H₅ | C₂H₅ | H | H | CH₂C(CH₃)₂CH₃ |
| 2.183 | 6-Cl | H | C₂H₅ | C₂H₅ | H | H | CH₂CH(phenyl)₂ |
| 2.184 | 6-Cl | H | C₂H₅ | C₂H₅ | H | H | 1-methyl-2,2-di-chloro-1-cyclopropyl |
| 2.185 | 6-Cl | H | C₂H₅ | C₂H₅ | H | H | 1-methyl-1-cyclohexyl |
| 2.186 | 6-Cl | H | C₂H₅ | C₂H₅ | H | H | cyclopentyl |
| 2.187 | 6-Cl | H | C₂H₅ | C₂H₅ | CH₃ | CH₃ | 4-Cl-phenyl |

TABLE 3

Compounds of formula (XIa)

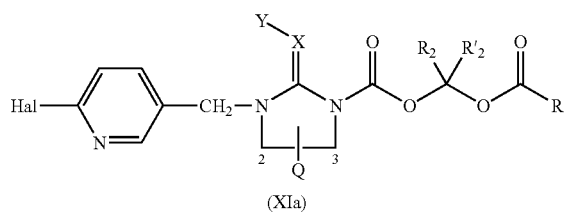

(XIa)

| No. | Hal | Y | X | Q | R₂ | R'₂ | R |
|---|---|---|---|---|---|---|---|
| 3.001 | Cl | NO₂ | CH | H | H | H | CH₃ |
| 3.002 | Cl | NO₂ | N | H | H | H | CH₃ |
| 3.003 | F | NO₂ | CH | H | H | H | CH₃ |
| 3.004 | Cl | NO₂ | CH | 3-CH₃ | H | H | CH₃ |
| 3.005 | Cl | CN | CH | H | H | H | CH₃ |
| 3.006 | Cl | CN | N | H | H | H | CH₃ |
| 3.007 | Cl | NO₂ | CH | H | H | H | C₂H₅ |
| 3.008 | Cl | NO₂ | N | H | H | H | C₂H₅ |
| 3.009 | F | NO₂ | CH | H | H | H | C₂H₅ |
| 3.010 | Cl | NO₂ | CH | 2-CH₃ | H | H | C₂H₅ |
| 3.011 | Cl | CN | CH | H | H | H | C₂H₅ |
| 3.012 | Cl | NO₂ | CH | H | H | H | n-C₃H₇ |
| 3.013 | Cl | NO₂ | N | H | H | H | n-C₄H₉ |
| 3.014 | F | NO₂ | CH | H | H | H | s-C₄H₉ |
| 3.015 | Cl | NO₂ | CH | 3-CH₃ | H | H | t-C₄H₉ |
| 3.016 | Cl | CN | CH | H | H | H | n-C₇H₁₅ |
| 3.017 | Cl | CN | N | H | H | H | n-C₁₁H₂₃ |
| 3.018 | Cl | NO₂ | CH | H | H | H | n-C₁₃H₂₇ |
| 3.019 | Cl | NO₂ | N | H | H | H | n-C₁₅H₃₁ |
| 3.020 | F | NO₂ | CH | H | H | H | n-C₁₇H₃₅ |
| 3.021 | Cl | NO₂ | CH | 2-CH₃ | H | H | n-C₁₁H₂₃ |
| 3.022 | Cl | CN | CH | H | H | H | n-C₇H₁₅ |
| 3.023 | Cl | NO₂ | CH | H | H | H | phenyl |
| 3.024 | Cl | NO₂ | N | H | H | CH₃ | phenyl |
| 3.025 | F | NO₂ | CH | H | H | H | biphenyl |
| 3.026 | Cl | NO₂ | CH | 3-CH₃ | H | H | phenoxyphenyl |
| 3.027 | Cl | CN | CH | H | H | H | 4-t-butyl-phenyl |
| 3.028 | Cl | CN | N | H | H | H | 2-chloro-phenyl |
| 3.029 | Cl | NO₂ | CH | 3-C₂H₅ | H | H | 2,6-difluoro-phenyl |
| 3.030 | Cl | CN | CH | 2-CH₃ | H | H | n-C₁₇H₃₅ |
| 3.031 | Cl | CN | N | 3-CH₃ | CH₃ | H | n-C₇H₁₅ |

TABLE 3-continued

Compounds of formula (XIa)

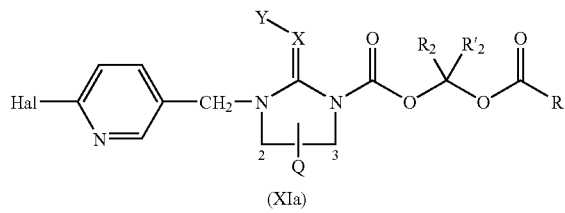

(XIa)

| No. | Hal | Y | X | Q | $R_2$ | $R'_2$ | R |
|---|---|---|---|---|---|---|---|
| 3.032 | Cl | CN | N | H | H | H | cyclohexyl |
| 3.033 | Cl | CN | N | H | H | H | vinyl |
| 3.034 | Cl | CN | CH | H | H | H | allyl |
| 3.035 | Cl | CN | N | H | H | H | 2-propargyl |
| 3.036 | Cl | $NO_2$ | N | H | H | H | cyclohexyl |
| 3.037 | Cl | $NO_2$ | N | H | H | H | vinyl |
| 3.038 | Cl | $NO_2$ | N | H | H | H | allyl |
| 3.039 | Cl | $NO_2$ | CH | H | H | H | 2-propargyl |
| 3.040 | Cl | CN | CH | H | $C_2H_5$ | H | $C_2H_5$ |
| 3.041 | Br | $NO_2$ | CH | H | H | H | n-$C_3H_7$ |
| 3.042 | Cl | $NO_2$ | N | H | $C_2H_5$ | $CH_3$ | n-$C_4H_9$ |
| 3.043 | F | $NO_2$ | CH | H | $C_2H_5$ | H | s-$C_4H_9$ |
| 3.044 | Br | $NO_2$ | CH | 3-$CH_3$ | $C_2H_5$ | H | t-$C_4H_9$ |
| 3.045 | Cl | CN | CH | H | $C_2H_5$ | H | n-$C_7H_{15}$ |
| 3.046 | Cl | $NO_2$ | CH | H | H | H | $C(CH_3)_2C_3H_7$-n |
| 3.047 | Cl | CN | CH | H | H | H | $C(CH_3)_2C_3H_7$-n |
| 3.048 | Cl | $NO_2$ | CH | H | H | H | $C(CH_3)_2C_2H_5$ |
| 3.049 | Cl | $NO_2$ | CH | H | H | H | n-$C_6H_{13}$ |
| 3.050 | Cl | $NO_2$ | CH | H | H | H | n-$C_{10}H_{21}$ |
| 3.051 | Cl | CN | $C_2H_5$ | $CH_3$ | H | H | $CH(CH_3)C_3H_7$n |
| 3.052 | Cl | $NO_2$ | $C_2H_5$ | $CH_3$ | H | H | n-$C_5H_{11}$ |
| 3.053 | Cl | CN | $C_2H_5$ | $CH_3$ | H | H | n-$C_8H_{17}$ |
| 3.054 | Cl | $NO_2$ | $C_2H_5$ | $CH_3$ | H | H | n-$C_4H_9$ |
| 3.055 | Cl | $NO_2$ | $C_2H_5$ | $CH_3$ | H | H | 1-phenyl-1-cyclo-pentyl |
| 3.056 | Cl | CN | $C_2H_5$ | $CH_3$ | H | H | 1-phenyl-1-cyclo-propyl |
| 3.057 | Cl | $NO_2$ | $C_2H_5$ | $CH_3$ | H | H | 1-phenyl-1-cyclo-hexyl |
| 3.058 | Cl | CN | $C_2H_5$ | $CH_3$ | H | H | $C(CH_3)_2$phenyl |
| 3.059 | Cl | $NO_2$ | $C_2H_5$ | $CH_3$ | H | H | 2,6-dimethylphenyl |
| 3.060 | Cl | $NO_2$ | $C_2H_5$ | $CH_3$ | H | H | 2,4,6-tri-isopropyl-phenyl |
| 3.061 | Cl | CN | $C_2H_5$ | $CH_3$ | H | H | cyclohexyl |
| 3.062 | Cl | $NO_2$ | $C_2H_5$ | $CH_3$ | H | H | benzyl |
| 3.063 | Cl | CN | $C_2H_5$ | $CH_3$ | H | H | 1-adamantyl |
| 3.064 | Cl | $NO_2$ | $C_2H_5$ | $CH_3$ | H | H | t-$C_4H_9$ |
| 3.065 | Cl | $NO_2$ | $C_2H_5$ | $CH_3$ | H | H | CH(phenyl)$_2$ |
| 3.066 | Cl | CN | $C_2H_5$ | $CH_3$ | H | H | cyclopropyl |
| 3.067 | Cl | $NO_2$ | $C_2H_5$ | $CH_3$ | H | H | $CH(C_2H_5)_2$ |
| 3.068 | Cl | CN | $C_2H_5$ | $CH_3$ | H | H | $CH(n-C_3H_7)_2$ |
| 3.069 | Cl | $NO_2$ | $C_2H_5$ | $CH_3$ | H | H | $CH_2$(cyclohexyl) |
| 3.070 | Cl | $NO_2$ | $C_2H_5$ | $CH_3$ | H | H | $CH_2CH_2$(cyclo-hexyl) |
| 3.071 | Cl | CN | $C_2H_5$ | $CH_3$ | H | H | 3-(t-$C_4H_9$)cyclo-hex-1-yl |
| 3.072 | Cl | $NO_2$ | $C_2H_5$ | $CH_3$ | H | H | 1-(4-chloro-phenyl)-1-cyclopentyl |
| 3.073 | Cl | CN | $C_2H_5$ | $CH_3$ | H | H | 1-(4-fluoro-phenyl)-1-cyclopentyl |
| 3.074 | Cl | $NO_2$ | $C_2H_5$ | $CH_3$ | H | H | $CH_2C(CH_3)_2CH_3$ |
| 3.075 | Cl | $NO_2$ | $C_2H_5$ | $CH_3$ | H | H | $CH_2CH$(phenyl)$_2$ |
| 3.076 | Cl | $NO_2$ | $C_2H_5$ | $CH_3$ | H | H | 1-methyl-2,2-di-chloro-1-cyclopropyl |
| 3.077 | Cl | $NO_2$ | $C_2H_5$ | $CH_3$ | H | H | 1-methyl-1-cyclohexyl |
| 3.078 | Cl | CN | $C_2H_5$ | $CH_3$ | H | H | cyclopentyl |
| 3.079 | Cl | $NO_2$ | $C_2H_5$ | $CH_3$ | $CH_3$ | $CH_3$ | 4-Cl-phenyl |

TABLE 4

Compounds of formula (XIIa)

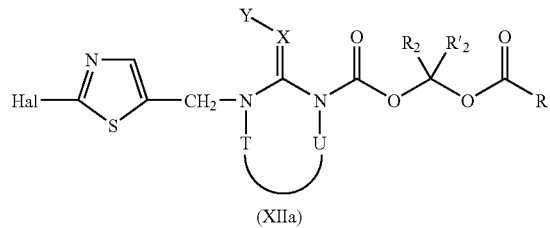

(XIIa)

| No. | Hal | Y | X | T-U | $R_2$ | $R'_2$ | R |
|---|---|---|---|---|---|---|---|
| 4.001 | Cl | $NO_2$ | CH | —$(CH_2)_3$— | H | H | $CH_3$ |
| 4.002 | Cl | $NO_2$ | N | —$(CH_2)_3$— | H | H | $CH_3$ |
| 4.003 | F | $NO_2$ | CH | —$(CH_2)_3$— | H | H | $CH_3$ |
| 4.004 | F | $NO_2$ | N | —$(CH_2)_3$— | H | H | $CH_3$ |
| 4.005 | Cl | CN | CH | —$(CH_2)_3$— | H | H | $CH_3$ |
| 4.006 | Cl | CN | N | —$(CH_2)_3$— | H | H | $CH_3$ |
| 4.007 | Cl | $NO_2$ | CH | —$(CH_2)_3$— | H | H | $C_2H_5$ |
| 4.008 | Cl | $NO_2$ | N | —$(CH_2)_3$— | H | H | $C_2H_5$ |
| 4.009 | F | $NO_2$ | CH | —$(CH_2)_3$— | H | H | $C_2H_5$ |
| 4.010 | Cl | $NO_2$ | CH | —$(CH_2)_3$— | $CH_3$ | H | $C_2H_5$ |
| 4.011 | Cl | CN | CH | —$(CH_2)_3$— | H | H | $C_2H_5$ |
| 4.012 | Cl | $NO_2$ | CH | —$(CH_2)_3$— | H | H | $n-C_3H_7$ |
| 4.013 | Cl | $NO_2$ | N | —$(CH_2)_3$— | H | H | $n-C_4H_9$ |
| 4.014 | F | $NO_2$ | CH | —$(CH_2)_3$— | H | H | $s-C_4H_9$ |
| 4.015 | Cl | $NO_2$ | CH | —$(CH_2)_3$— | H | H | $t-C_4H_9$ |
| 4.016 | Cl | CN | CH | —$(CH_2)_3$— | H | H | $n-C_7H_{15}$ |
| 4.017 | Cl | CN | N | —$(CH_2)_3$— | H | H | $n-C_{11}H_{23}$ |
| 4.018 | Cl | $NO_2$ | CH | —$(CH_2)_3$— | H | H | $n-C_{13}H_{27}$ |
| 4.019 | Cl | $NO_2$ | N | —$(CH_2)_3$— | H | H | $n-C_{15}H_{31}$ |
| 4.020 | F | $NO_2$ | CH | —$(CH_2)_3$— | H | H | $n-C_{17}H_{35}$ |
| 4.021 | Cl | $NO_2$ | CH | —$(CH_2)_3$— | $CH_3$ | $CH_3$ | $n-C_{11}H_{23}$ |
| 4.022 | Cl | CN | CH | —$(CH_2)_3$— | $CH_3$ | H | $n-C_7H_{15}$ |
| 4.023 | Cl | $NO_2$ | CH | —$(CH_2)_3$— | H | H | phenyl |
| 4.024 | Cl | $NO_2$ | N | —$(CH_2)_3$— | H | $CH_3$ | phenyl |
| 4.025 | F | CN | CH | —$(CH_2)_3$— | H | H | biphenyl |
| 4.026 | Cl | $NO_2$ | CH | —$(CH_2)_3$— | H | H | phenoxyphenyl |
| 4.027 | Cl | CN | CH | —$(CH_2)_3$— | H | H | 4-t-butyl-phenyl |
| 4.028 | Cl | CN | N | —$(CH_2)_3$— | H | H | 2-chloro-phenyl |
| 4.029 | Cl | $NO_2$ | CH | —$(CH_2)_3$— | H | H | 2,6-difluoro-phenyl |
| 4.030 | Cl | CN | CH | —$(CH_2)_3$— | H | H | $n-C_{17}H_{35}$ |
| 4.031 | Br | CN | N | —$(CH_2)_3$— | $CH_3$ | H | $n-C_7H_{15}$ |
| 4.032 | Cl | CN | N | —$(CH_2)_3$— | H | H | cyclohexyl |
| 4.033 | Cl | CN | N | —$(CH_2)_3$— | H | H | vinyl |
| 4.034 | Cl | CN | CH | —$(CH_2)_3$— | H | H | allyl |
| 4.035 | Cl | CN | N | —$(CH_2)_3$— | H | H | 2-propargyl |
| 4.036 | Cl | $NO_2$ | N | —$(CH_2)_3$— | H | H | cyclohexyl |
| 4.037 | Cl | $NO_2$ | N | —$(CH_2)_3$— | H | H | vinyl |
| 4.038 | Cl | $NO_2$ | N | —$(CH_2)_3$— | H | H | allyl |
| 4.039 | Cl | $NO_2$ | CH | —$CH_2OCH_2$— | H | H | 2-propargyl |
| 4.040 | Cl | $NO_2$ | CH | —$CH_2OCH_2$— | H | H | $CH_3$ |
| 4.041 | Cl | $NO_2$ | N | —$CH_2OCH_2$— | H | H | $CH_3$ |
| 4.042 | F | $NO_2$ | CH | —$CH_2OCH_2$— | H | H | $CH_3$ |
| 4.043 | F | $NO_2$ | N | —$CH_2OCH_2$— | H | H | $CH_3$ |
| 4.044 | Cl | CN | CH | —$CH_2OCH_2$— | H | H | $CH_3$ |
| 4.045 | Cl | CN | N | —$CH_2OCH_2$— | H | H | $CH_3$ |
| 4.045 | Cl | $NO_2$ | CH | —$CH_2OCH_2$— | H | H | $C_2H_5$ |
| 4.047 | Cl | $NO_2$ | N | —$CH_2OCH_2$— | H | H | $C_2H_5$ |
| 4.048 | F | $NO_2$ | CH | —$CH_2OCH_2$— | H | H | $C_2H_5$ |
| 4.049 | Cl | $NO_2$ | CH | —$CH_2OCH_2$— | $CH_3$ | H | $C_2H_5$ |
| 4.050 | Cl | CN | CH | —$CH_2OCH_2$— | H | H | $C_2H_5$ |
| 4.051 | Cl | $NO_2$ | CH | —$CH_2OCH_2$— | H | H | $n-C_3H_7$ |
| 4.052 | Cl | $NO_2$ | N | —$CH_2OCH_2$— | H | H | $n-C_4H_9$ |
| 4.053 | F | $NO_2$ | CH | —$CH_2OCH_2$— | H | H | $s-C_4H_9$ |
| 4.054 | Cl | $NO_2$ | CH | —$CH_2OCH_2$— | H | H | $t-C_4H_9$ |
| 4.055 | Cl | CN | CH | —$CH_2OCH_2$— | H | H | $n-C_7H_{15}$ |
| 4.056 | Cl | CN | N | —$CH_2OCH_2$— | H | H | $n-C_{11}H_{23}$ |
| 4.057 | Cl | $NO_2$ | CH | —$CH_2OCH_2$— | H | H | $n-C_{13}H_{27}$ |
| 4.058 | Cl | $NO_2$ | N | —$CH_2OCH_2$— | H | H | $n-C_{15}H_{31}$ |
| 4.059 | F | $NO_2$ | CH | —$CH_2OCH_2$— | H | H | $n-C_{17}H_{35}$ |
| 4.060 | Cl | $NO_2$ | CH | —$CH_2OCH_2$— | $CH_3$ | $CH_3$ | $n-C_{11}H_{23}$ |
| 4.061 | Cl | CN | CH | —$CH_2OCH_2$— | $CH_3$ | H | $n-C_7H_{15}$ |
| 4.062 | Cl | $NO_2$ | CH | —$CH_2OCH_2$— | H | H | phenyl |
| 4.063 | Cl | $NO_2$ | N | —$CH_2OCH_2$— | H | $CH_3$ | phenyl |

TABLE 4-continued

Compounds of formula (XIIa)

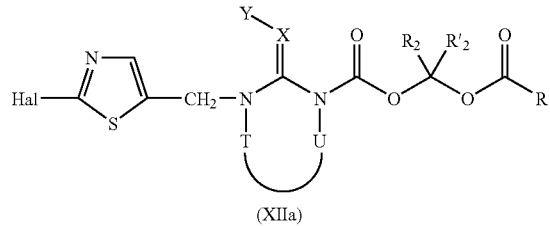

(XIIa)

| No. | Hal | Y | X | T-U | $R_2$ | $R'_2$ | R |
|---|---|---|---|---|---|---|---|
| 4.064 | F | CN | CH | —CH$_2$OCH$_2$— | H | H | biphenyl |
| 4.065 | Cl | NO$_2$ | CH | —CH$_2$OCH$_2$— | H | H | phenoxyphenyl |
| 4.066 | Cl | CN | CH | —CH$_2$OCH$_2$— | H | H | 4-t-butyl-phenyl |
| 4.067 | Cl | CN | N | —CH$_2$OCH$_2$— | H | H | 2-chloro-phenyl |
| 4.068 | Cl | NO$_2$ | CH | —CH$_2$OCH$_2$— | H | H | 2,6-difluoro-phenyl |
| 4.069 | Cl | CN | CH | —CH$_2$OCH$_2$— | H | H | n-C$_{17}$H$_{35}$ |
| 4.070 | Br | CN | N | —CH$_2$OCH$_2$— | CH$_3$ | H | n-C$_7$H$_{15}$ |
| 4.071 | Cl | CN | N | —CH$_2$OCH$_2$— | H | H | cyclohexyl |
| 4.072 | Cl | CN | N | —CH$_2$OCH$_2$— | H | H | vinyl |
| 4.073 | Cl | CN | CH | —CH$_2$OCH$_2$— | H | H | allyl |
| 4.074 | Cl | CN | N | —CH$_2$OCH$_2$— | H | H | 2-propargyl |
| 4.075 | Cl | NO$_2$ | N | —CH$_2$OCH$_2$— | H | H | cyclohexyl |
| 4.076 | Cl | NO$_2$ | N | —CH$_2$OCH$_2$— | H | H | vinyl |
| 4.077 | Cl | NO$_2$ | N | —CH$_2$OCH$_2$— | H | H | allyl |
| 4.078 | Cl | NO$_2$ | CH | —CH$_2$OCH$_2$— | H | H | 2-propargyl |
| 4.079 | Cl | NO$_2$ | CH | —CH$_2$N(CH$_3$)CH$_2$— | H | H | CH$_3$ |
| 4.080 | Cl | NO$_2$ | N | —CH$_2$N(CH$_3$)CH$_2$— | H | H | CH$_3$ |
| 4.081 | F | NO$_2$ | CH | —CH$_2$N(CH$_3$)CH$_2$— | H | H | CH$_3$ |
| 4.082 | F | NO$_2$ | N | —CH$_2$N(CH$_3$)CH$_2$— | H | H | CH$_3$ |
| 4.083 | Cl | CN | CH | —CH$_2$N(CH$_3$)CH$_2$— | H | H | CH$_3$ |
| 4.084 | Cl | CN | N | —CH$_2$N(CH$_3$)CH$_2$— | H | H | CH$_3$ |
| 4.085 | Cl | NO$_2$ | CH | —CH$_2$N(CH$_3$)CH$_2$— | H | H | C$_2$H$_5$ |
| 4.086 | Cl | NO$_2$ | N | —CH$_2$N(CH$_3$)CH$_2$— | H | H | C$_2$H$_5$ |
| 4.087 | F | NO$_2$ | CH | —CH$_2$N(CH$_3$)CH$_2$— | H | H | C$_2$H$_5$ |
| 4.088 | Cl | NO$_2$ | CH | —CH$_2$N(CH$_3$)CH$_2$— | CH$_3$ | H | C$_2$H$_5$ |
| 4.089 | Cl | CN | CH | —CH$_2$N(CH$_3$)CH$_2$— | H | H | C$_2$H$_5$ |
| 4.090 | Cl | NO$_2$ | CH | —CH$_2$N(CH$_3$)CH$_2$— | H | H | n-C$_3$H$_7$ |
| 4.091 | Cl | NO$_2$ | N | —CH$_2$N(CH$_3$)CH$_2$— | H | H | n-C$_4$H$_9$ |
| 4.092 | F | NO$_2$ | CH | —CH$_2$N(CH$_3$)CH$_2$— | H | H | s-C$_4$H$_9$ |
| 4.093 | Cl | NO$_2$ | CH | —CH$_2$N(CH$_3$)CH$_2$— | H | H | t-C$_4$H$_9$ |
| 4.094 | Cl | CN | CH | —CH$_2$N(CH$_3$)CH$_2$— | H | H | n-C$_7$H$_{15}$ |
| 4.095 | Cl | CN | N | —CH$_2$N(CH$_3$)CH$_2$— | H | H | n-C$_{11}$H$_{23}$ |
| 4.096 | Cl | NO$_2$ | N | —(CH$_2$)$_3$— | H | H | CH(CH$_3$)C$_3$H$_7$-n |
| 4.097 | Cl | CN | N | —(CH$_2$)$_3$— | H | H | C(CH$_3$)$_2$C$_3$H$_7$-n |
| 4.098 | Cl | NO$_2$ | N | —(CH$_2$)$_3$— | H | H | C(CH$_3$)$_2$C$_2$H$_5$ |
| 4.099 | Cl | NO$_2$ | N | —(CH$_2$)$_3$— | H | H | n-C$_6$H$_{13}$ |
| 4.100 | Cl | NO$_2$ | N | —(CH$_2$)$_3$— | H | H | n-C$_{10}$H$_{21}$ |
| 4.101 | Cl | CN | C$_2$H$_5$ | CH$_3$ | H | H | CH(CH$_3$)C$_3$H$_7$n |
| 4.102 | Cl | NO$_2$ | C$_2$H$_5$ | CH$_3$ | H | H | n-C$_5$H$_{11}$ |
| 4.103 | Cl | NO$_2$ | C$_2$H$_5$ | CH$_3$ | H | H | n-C$_8$H$_{17}$ |
| 4.104 | F | NO$_2$ | C$_2$H$_5$ | CH$_3$ | H | H | n-C$_4$H$_9$ |
| 4.105 | Cl | NO$_2$ | C$_2$H$_5$ | CH$_3$ | H | H | 1-phenyl-1-cyclo-pentyl |
| 4.106 | Cl | CN | C$_2$H$_5$ | CH$_3$ | H | H | 1-phenyl-1-cyclo-propyl |
| 4.107 | Cl | CN | C$_2$H$_5$ | CH$_3$ | H | H | 1-phenyl-1-cyclo-hexyl |
| 4.108 | Cl | NO$_2$ | C$_2$H$_5$ | CH$_3$ | H | H | C(CH$_3$)$_2$phenyl |
| 4.109 | Cl | CN | C$_2$H$_5$ | CH$_3$ | H | H | 2,6-dimethylphenyl |
| 4.110 | Cl | NO$_2$ | C$_2$H$_5$ | CH$_3$ | H | H | 2,4,6-tri-isopropyl-phenyl |
| 4.111 | Cl | NO$_2$ | C$_2$H$_5$ | CH$_3$ | H | H | cyclohexyl |
| 4.112 | Cl | NO$_2$ | C$_2$H$_5$ | CH$_3$ | H | H | benzyl |
| 4.113 | Cl | CN | C$_2$H$_5$ | CH$_3$ | H | H | 1-adamantyl |
| 4.114 | Cl | NO$_2$ | C$_2$H$_5$ | CH$_3$ | H | H | t-C$_4$H$_9$ |
| 4.115 | Cl | NO$_2$ | C$_2$H$_5$ | CH$_3$ | H | H | CH(phenyl)$_2$ |
| 4.116 | F | NO$_2$ | C$_2$H$_5$ | CH$_3$ | H | H | cyclopropyl |
| 4.117 | Cl | NO$_2$ | C$_2$H$_5$ | CH$_3$ | H | H | CH(C$_2$H$_5$)$_2$ |
| 4.118 | Cl | CN | C$_2$H$_5$ | CH$_3$ | H | H | CH(n-C$_3$H$_7$)$_2$ |
| 4.119 | Cl | CN | C$_2$H$_5$ | CH$_3$ | H | H | CH$_2$(cyclohexyl) |
| 4.120 | Cl | NO$_2$ | C$_2$H$_5$ | CH$_3$ | H | H | CH$_2$CH$_2$(cyclo-hexyl) |
| 4.121 | Cl | CN | C$_2$H$_5$ | CH$_3$ | H | H | 3-(t-C$_4$H$_9$)cyclo-hex-1-yl |
| 4.122 | Cl | NO$_2$ | C$_2$H$_5$ | CH$_3$ | H | H | 1-(4-chloro-phenyl)-1-cyclopentyl |
| 4.123 | Cl | NO$_2$ | C$_2$H$_5$ | CH$_3$ | H | H | 1-(4-fluoro-phenyl)-1-cyclopentyl |

TABLE 4-continued
Compounds of formula (XIIa)
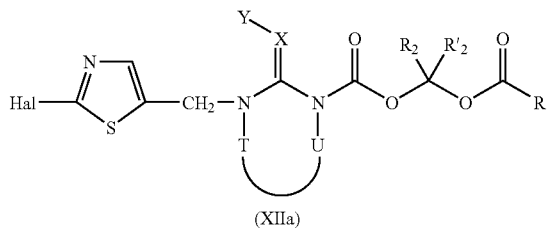
(XIIa)
| No. | Hal | Y | X | T-U | $R_2$ | $R'_2$ | R |
|---|---|---|---|---|---|---|---|
| 4.124 | Cl | $NO_2$ | $C_2H_5$ | $CH_3$ | H | H | $CH_2C(CH_3)_2CH_3$ |
| 4.125 | Cl | $NO_2$ | $C_2H_5$ | $CH_3$ | H | H | $CH_2CH(phenyl)_2$ |
| 4.126 | Cl | CN | $C_2H_5$ | $CH_3$ | H | H | 1-methyl-2,2-di-chloro-1-cyclopropyl |
| 4.127 | Cl | $NO_2$ | $C_2H_5$ | $CH_3$ | H | H | 1-methyl-1-cyclohexyl |
| 4.128 | Cl | $NO_2$ | $C_2H_5$ | $CH_3$ | H | H | cyclopentyl |
| 4.129 | Cl | $NO_2$ | $C_2H_5$ | $CH_3$ | $CH_3$ | $CH_3$ | 4-Cl-phenyl |
Further typical and interesting compounds of formula (I) are:
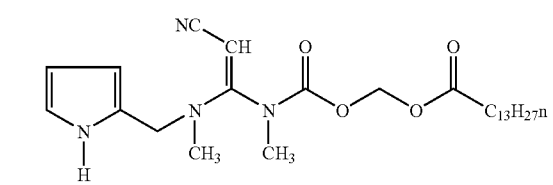
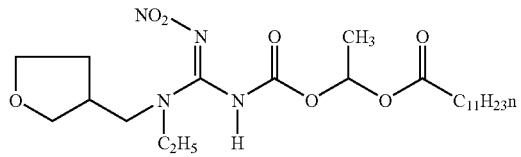
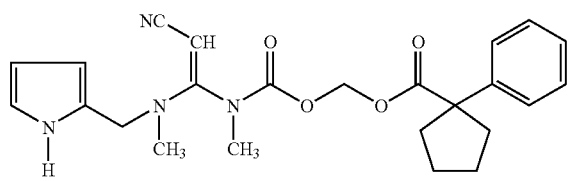
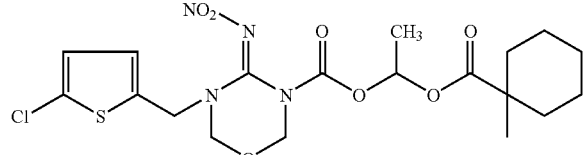
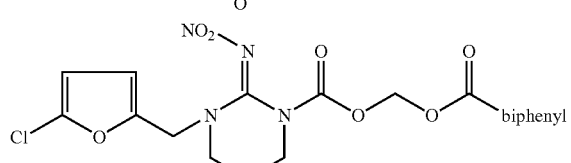
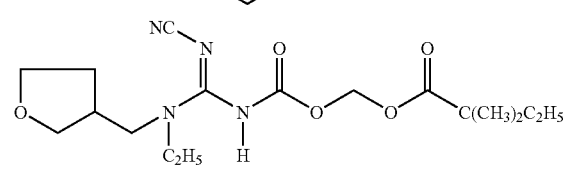
-continued
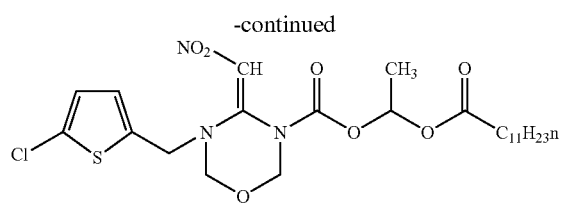
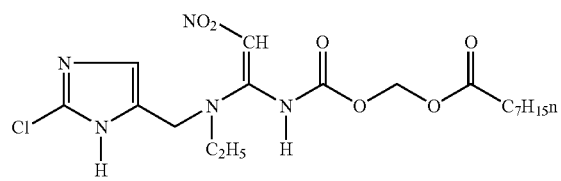
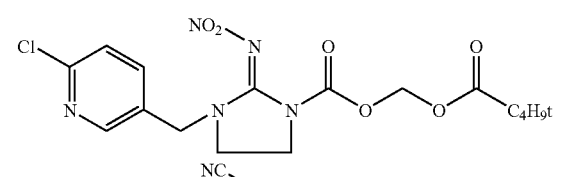
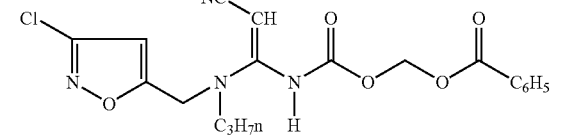
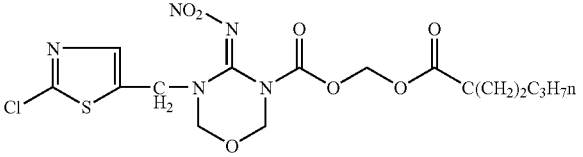
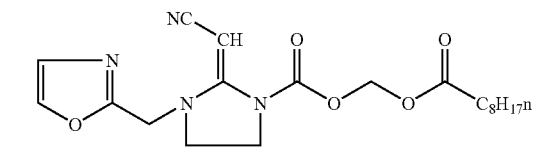

TABLE 5

Compounds of formula (XXa)

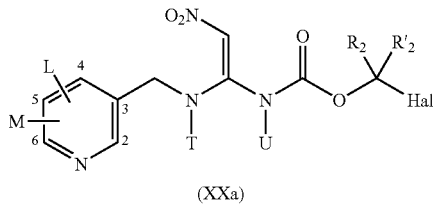

(XXa)

| No.   | M    | L    | T        | U        | R$_2$      | R'$_2$    | Hal | Physical Data |
|-------|------|------|----------|----------|------------|-----------|-----|---------------|
| 5.001 | 6-Cl | H    | C$_2$H$_5$ | CH$_3$   | H          | H         | F   |               |
| 5.002 | 6-Cl | 5-Cl | C$_2$H$_5$ | CH$_3$   | H          | H         | F   |               |
| 5.003 | 6-Cl | H    | CH$_3$   | CH$_3$   | H          | H         | F   |               |
| 5.004 | 6-Cl | H    | C$_2$H$_5$ | CH$_3$   | CH$_3$     | H         | F   |               |
| 5.005 | 6-Cl | H    | C$_2$H$_5$ | CH$_3$   | H          | H         | Cl  | m.p. 142-143° C. |
| 5.006 | 6-Cl | H    | C$_2$H$_5$ | CH$_3$   | H          | H         | Br  |               |
| 5.007 | 6-Cl | H    | C$_2$H$_5$ | CH$_3$   | H          | H         | I   |               |
| 5.008 | 6-Cl | H    | C$_2$H$_5$ | CH$_3$   | CH$_3$     | H         | Cl  |               |
| 5.009 | 6-Cl | H    | H        | CH$_3$   | CH$_3$     | H         | Br  |               |
| 5.010 | H    | 5-Cl | C$_2$H$_5$ | CH$_3$   | H          | H         | Cl  |               |
| 5.011 | 6-Cl | H    | C$_2$H$_5$ | CH$_3$   | H          | H         | Cl  |               |
| 5.012 | 6-Cl | H    | C$_2$H$_5$ | H        | H          | H         | Br  |               |
| 5.013 | 6-Cl | H    | C$_2$H$_5$ | C$_2$H$_5$ | CH$_3$   | H         | Br  |               |
| 5.014 | 6-Cl | H    | C$_2$H$_5$ | CH$_3$   | C$_2$H$_5$ | H         | F   |               |
| 5.015 | 6-Cl | H    | C$_2$H$_5$ | CH$_3$   | n-C$_3$H$_7$ | H       | F   |               |
| 5.016 | 6-Cl | H    | C$_2$H$_5$ | CH$_3$   | s-C$_4$H$_9$ | H       | F   |               |
| 5.017 | 6-Cl | H    | C$_2$H$_5$ | CH$_3$   | n-C$_6$H$_{13}$ | H    | F   |               |
| 5.018 | 6-Cl | H    | CH$_3$   | CH$_3$   | CH$_3$     | H         | F   |               |
| 5.019 | 6-Cl | 4-F  | CH$_3$   | CH$_3$   | CH$_3$     | H         | F   |               |
| 5.020 | 6-Cl | H    | C$_2$H$_5$ | CH$_3$   | CH$_3$     | CH$_3$    | I   |               |
| 5.021 | 6-Cl | H    | C$_2$H$_5$ | CH$_3$   | CH$_3$     | CH$_3$    | F   |               |
| 5.022 | 6-Cl | H    | C$_2$H$_5$ | CH$_3$   | C$_2$H$_5$ | CH$_3$    | Cl  |               |
| 5.023 | 6-Cl | H    | C$_2$H$_5$ | CH$_3$   | CH$_3$     | CH$_3$    | Br  |               |
| 5.024 | 6-Cl | H    | C$_2$H$_5$ | CH$_3$   | C$_2$H$_5$ | C$_2$H$_5$ | I  |               |
| 5.025 | 6-Cl | H    | C$_2$H$_5$ | CH$_3$   | n-C$_3$H$_7$ | C$_2$H$_5$ | Cl |               |
| 5.026 | 6-Cl | H    | C$_2$H$_5$ | CH$_3$   | CH$_3$     | s-C$_4$H$_9$ | Br |               |
| 5.027 | 6-Cl | H    | C$_2$H$_5$ | CH$_3$   | CH$_3$     | n-C$_3$H$_7$ | I |               |
| 5.028 | 6-Cl | H    | C$_2$H$_5$ | CH$_3$   | s-C$_4$H$_9$ | C$_2$H$_5$ | F |               |
| 5.029 | 6-Cl | H    | C$_2$H$_5$ | CH$_3$   | s-C$_4$H$_9$ | n-C$_3$H$_7$ | Cl |              |
| 5.030 | 6-Cl | H    | C$_2$H$_5$ | C$_2$H$_5$ | CH$_3$   | n-C$_3$H$_7$ | I |               |
| 5.031 | 6-Cl | H    | C$_2$H$_5$ | CH$_3$   | C$_2$H$_5$ | CH$_3$    | F   |               |
| 5.032 | 6-Cl | H    | C$_2$H$_5$ | CH$_3$   | n-C$_3$H$_7$ | CH$_3$  | F   |               |
| 5.033 | 6-Cl | H    | C$_2$H$_5$ | CH$_3$   | s-C$_4$H$_9$ | CH$_3$  | F   |               |
| 5.034 | 6-Cl | H    | C$_2$H$_5$ | CH$_3$   | n-C$_6$H$_{13}$ | H    | F   |               |

TABLE 6

Compounds of formula (XXb)

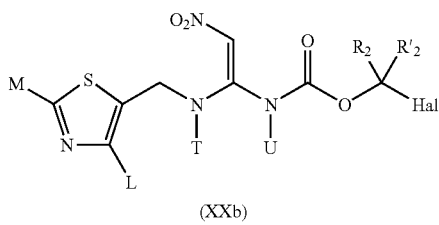

(XXb)

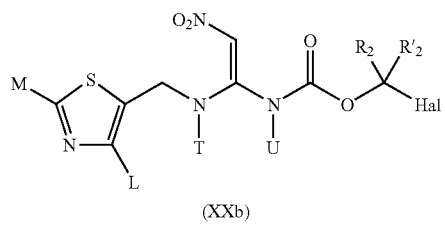

(XXb)

| No.   | L  | M  | T        | U      | R$_2$   | R'$_2$ | Hal | No.   | L | M  | T        | U        | R$_2$      | R'$_2$ | Hal |
|-------|----|----|----------|--------|---------|--------|-----|-------|---|----|----------|----------|------------|--------|-----|
| 6.001 | H  | Cl | C$_2$H$_5$ | CH$_3$ | H       | H      | Cl  | 6.009 | H | Cl | H        | CH$_3$   | H          | H      | Cl  |
| 6.002 | Cl | Cl | C$_2$H$_5$ | CH$_3$ | H       | H      | Cl  | 6.010 | H | Cl | C$_2$H$_5$ | C$_2$H$_5$ | H        | H      | Cl  |
| 6.003 | H  | F  | CH$_3$   | CH$_3$ | H       | H      | Cl  | 6.011 | H | Cl | C$_2$H$_5$ | CH$_3$   | H          | H      | I   |
| 6.004 | H  | Cl | C$_2$H$_5$ | CH$_3$ | CH$_3$  | H      | Cl  | 6.012 | H | Cl | C$_2$H$_5$ | CH$_3$   | CH$_3$     | H      | I   |
| 6.005 | F  | Cl | C$_2$H$_5$ | CH$_3$ | H       | H      | F   | 6.013 | H | Cl | C$_2$H$_5$ | CH$_3$   | CH$_3$     | CH$_3$ | I   |
| 6.006 | H  | Cl | C$_2$H$_5$ | CH$_3$ | H       | H      | F   | 6.014 | H | H  | C$_2$H$_5$ | CH$_3$   | CH$_3$     | H      | F   |
| 6.007 | H  | Cl | C$_2$H$_5$ | CH$_3$ | H       | H      | Br  | 6.015 | H | Cl | C$_2$H$_5$ | CH$_3$   | C$_2$H$_5$ | H      | Cl  |
| 6.008 | H  | Cl | C$_2$H$_5$ | CH$_3$ | CH$_3$  | H      | F   | 6.016 | H | Cl | C$_2$H$_5$ | CH$_3$   | n-C$_3$H$_7$ | H    | Cl  |

TABLE 6-continued

Compounds of formula (XXb)

| No. | L | M | T | U | R₂ | R'₂ | Hal |
|---|---|---|---|---|---|---|---|
| 6.017 | H | Cl | $C_2H_5$ | $CH_3$ | $s-C_4H_9$ | H | Cl |
| 6.018 | H | Cl | $C_2H_5$ | $CH_3$ | $n-C_6H_{13}$ | H | Cl |
| 6.019 | H | Cl | $CH_3$ | $CH_3$ | $CH_3$ | H | Cl |
| 6.020 | H | F | $CH_3$ | $CH_3$ | $CH_3$ | H | Cl |
| 6.021 | H | Cl | $C_2H_5$ | $CH_3$ | $C_2H_5$ | $CH_3$ | I |
| 6.022 | H | Cl | $C_2H_5$ | $CH_3$ | $CH_3$ | H | Br |
| 6.023 | H | Cl | $C_2H_5$ | $CH_3$ | $CH_3$ | $CH_3$ | F |

TABLE 7

Compounds of formula (XXc)

| No. | Hal | Y | X | Q | R₂ | R'₂ | Hal' |
|---|---|---|---|---|---|---|---|
| 7.001 | Cl | $NO_2$ | CH | H | H | H | Cl |
| 7.002 | Cl | $NO_2$ | N | H | H | H | Cl |
| 7.003 | F | $NO_2$ | CH | H | H | H | Cl |
| 7.004 | Cl | $NO_2$ | CH | $3-CH_3$ | H | H | Cl |
| 7.005 | Cl | CN | CH | H | H | H | Cl |
| 7.006 | Cl | CN | N | H | H | H | Cl |
| 7.007 | Cl | $NO_2$ | CH | H | H | H | F |
| 7.008 | Cl | $NO_2$ | N | H | H | H | F |
| 7.009 | F | $NO_2$ | CH | H | H | H | F |
| 7.010 | Cl | $NO_2$ | CH | $2-CH_3$ | H | H | F |
| 7.011 | Cl | CN | CH | H | H | H | Br |
| 7.012 | Cl | $NO_2$ | CH | H | H | H | Br |
| 7.013 | Cl | $NO_2$ | N | H | H | H | I |
| 7.014 | F | $NO_2$ | CH | H | H | H | I |
| 7.015 | Cl | $NO_2$ | CH | $3-CH_3$ | H | H | Cl |
| 7.016 | Cl | CN | CH | H | $CH_3$ | H | Cl |
| 7.017 | Cl | CN | N | H | $CH_3$ | H | Cl |
| 7.018 | Cl | $NO_2$ | CH | H | $CH_3$ | H | Cl |
| 7.019 | Cl | $NO_2$ | N | H | $CH_3$ | H | Cl |
| 7.020 | F | $NO_2$ | CH | H | $CH_3$ | H | Cl |
| 7.021 | Cl | $NO_2$ | CH | $2-CH_3$ | $CH_3$ | H | Cl |
| 7.022 | Cl | CN | CH | H | $CH_3$ | H | F |
| 7.023 | Cl | $NO_2$ | CH | H | $CH_3$ | H | F |
| 7.024 | Cl | $NO_2$ | N | H | $CH_3$ | $CH_3$ | F |
| 7.025 | F | $NO_2$ | CH | H | $CH_3$ | H | F |
| 7.026 | Cl | $NO_2$ | CH | $3-CH_3$ | $CH_3$ | H | F |
| 7.027 | Cl | CN | CH | H | $CH_3$ | H | Br |
| 7.028 | Cl | CN | N | H | $CH_3$ | H | Br |
| 7.029 | Cl | $NO_2$ | CH | $3-C_2H_5$ | H | H | Cl |
| 7.030 | Cl | CN | CH | $2-CH_3$ | $CH_3$ | $CH_3$ | Cl |

TABLE 8

Compounds of formula (XXd)

| No. | Hal | Y | X | T–U | R₂ | R₂' | Hal' |
|---|---|---|---|---|---|---|---|
| 8.001 | Cl | $NO_2$ | CH | $-(CH_2)_3-$ | H | H | Cl |
| 8.002 | Cl | $NO_2$ | N | $-(CH_2)_3-$ | H | H | Cl |
| 8.003 | F | $NO_2$ | CH | $-(CH_2)_3-$ | H | H | Cl |
| 8.004 | F | $NO_2$ | N | $-(CH_2)_3-$ | H | H | Cl |
| 8.005 | Cl | CN | CH | $-(CH_2)_3-$ | H | H | Cl |
| 8.006 | Cl | CN | N | $-(CH_2)_3-$ | H | H | Cl |
| 8.007 | Cl | $NO_2$ | CH | $-(CH_2)_3-$ | H | H | F |
| 8.008 | Cl | $NO_2$ | N | $-(CH_2)_3-$ | H | H | F |
| 8.009 | F | $NO_2$ | CH | $-(CH_2)_3-$ | H | H | F |
| 8.010 | Cl | $NO_2$ | CH | $-(CH_2)_3-$ | $CH_3$ | H | F |
| 8.011 | Cl | CN | CH | $-(CH_2)_3-$ | H | H | Br |
| 8.012 | Cl | $NO_2$ | CH | $-(CH_2)_3-$ | H | H | Br |
| 8.013 | Cl | $NO_2$ | N | $-(CH_2)_3-$ | H | H | I |
| 8.014 | F | $NO_2$ | CH | $-(CH_2)_3-$ | H | H | I |
| 8.015 | Cl | $NO_2$ | CH | $-(CH_2)_3-$ | $CH_3$ | H | Cl |
| 8.016 | Cl | CN | CH | $-(CH_2)_3-$ | $CH_3$ | H | Cl |
| 8.017 | Cl | CN | N | $-(CH_2)_3-$ | $CH_3$ | H | Cl |
| 8.018 | Cl | $NO_2$ | CH | $-(CH_2)_3-$ | $CH_3$ | H | Cl |
| 8.019 | Cl | $NO_2$ | N | $-(CH_2)_3-$ | $CH_3$ | $CH_3$ | Cl |
| 8.020 | F | $NO_2$ | CH | $-(CH_2)_3-$ | $CH_3$ | $CH_3$ | Cl |
| 8.021 | Cl | $NO_2$ | CH | $-(CH_2)_3-$ | $CH_3$ | $CH_3$ | Cl |
| 8.022 | Cl | CN | CH | $-(CH_2)_3-$ | $CH_3$ | H | F |
| 8.023 | Cl | $NO_2$ | CH | $-(CH_2)_3-$ | H | H | F |
| 8.024 | Cl | $NO_2$ | N | $-(CH_2)_3-$ | H | $CH_3$ | F |
| 8.025 | F | CN | CH | $-(CH_2)_2-$ | $CH_3$ | $CH_3$ | F |
| 8.026 | Cl | $NO_2$ | CH | $-(CH_2)_2-$ | $CH_3$ | $CH_3$ | F |
| 8.027 | Cl | CN | CH | $-(CH_2)_3-$ | H | H | Br |
| 8.028 | Cl | CN | N | $-(CH_2)_3-$ | H | H | Br |
| 8.029 | Cl | $NO_2$ | CH | $-(CH_2)_3-$ | $C_2H_5$ | H | Cl |
| 8.030 | Cl | CN | CH | $-(CH_2)_3-$ | $C_2H_5$ | H | Cl |

It has now been found that systemic administration, for example by oral, percutaneous administration, or preferably topical application, for example in pour-on, spot-on or spray form, of a compound of formula (I) in an amount effective against insects is able drastically to reduce or completely to prevent attack by parasites on warm-blooded animals over a prolonged period.

The present invention therefore relates to the long-term control of parasites, especially blood-sucking insects but more especially the long-term control of fleas.

The compounds of formula (I) are distinguished inter alia by excellent activity against fleas, not only adult fleas being rapidly killed but also, by a circuitous route, the juvenile stages of the fleas. Flea larvae hatching out from the flea eggs feed mainly on the excreta of the adult fleas. Since the compounds of formula (I) according to the invention kill the adult fleas very rapidly, the necessary excreta are absent and the juvenile stages are deprived of the nutrient medium, so that they perish before reaching the adult stage.

The present invention therefore relates preferably to a method of controlling parasites on human beings, domestic animals, productive livestock and pets, which comprises administering systemically or preferably topically to the warm-blooded animal an effective amount of a composition comprising at least one compound of formula (I) or a physiologically tolerable salt thereof.

Long-term action is achieved by the compounds of formula (I) according to the invention using various forms of administration, for example by administering the active ingredient to the animal to be treated externally or internally in a formulated form. "Formulated" in this case means, e.g., in the form of a powder, a tablet or granules, in liposomes or a capsule, in the form of an emulsion, a foam or a spray, in microencapsulated form or in pour-on or spot-on form. It will be understood that all orally administrable compositions may comprise, in addition to customary formulation substances, further additives that encourage the host animal to take the composition orally voluntarily, e.g., suitable odoronts and flavorings.

Percutaneous administration, for example by subcutaneous or intramuscular injection or as a depot preparation in the form of an implant, and topical application, e.g., in pour-on or spot-on form, represent preferred subjects of this invention on account of their being easy to carry out. A further mode of administration is oral administration, e.g., in the form of a tablet. Percutaneous and topical forms of administration are of particular interest and give excellent results.

Percutaneous forms of administration include, e.g., subcutaneous, intramuscular and even intravenous administration of injectable forms. In addition to the customary syringes with needles, it is also possible to use needle-less high-pressure syringe devices.

Pour-on and spot-on formulations are especially preferred as topical forms of administration but administration in the form of sprays, ointments, solutions or powders may also be expedient.

By selection of a suitable formulation it is possible to enhance the ability of the active ingredients to penetrate into the living tissue of the host animal and/or to maintain its availability. That is important when, for example, rather sparingly soluble active ingredients are used, the low solubility of which requires means for enhancing solubility, since in such cases the animal's body fluid will be capable of dissolving only small amounts of active ingredient at a time.

In order to obtain a greatly delayed release of active ingredient, a compound of formula (I) according to the invention may also be present in a matrix formulation which physically prevents the active ingredient from being released and excreted prematurely and maintains the bioavailability of the active ingredient. Such a matrix formulation is injected into the body, e.g., intramuscularly or subcutaneously, and remains there as a form of depot from which active ingredient is released continuously. Such matrix formulations are known to a person skilled in the art. They are generally wax-like, semi-solid substances, e.g., vegetable waxes and polyethylene glycols having a high molecular weight, or solid polymer formulations, e.g., so-called microspheres.

The rate of release of the active ingredient from the implant and thus the period of time over which the implant exhibits an action is generally determined by the accuracy with which the implant has been calibrated (amount of active ingredient in the implant), the environment around the implant and the polymer formulation from which the implant has been made.

The administration of veterinary medicinal additives to animal food is well-known in the field of animal health. It is usual first to prepare a so-called premix in which the active ingredient is dispersed in a liquid or is present in finely divided form in solid carriers. The premix can normally comprise about 1-800 mg of compound per kg of premix, depending on the desired final concentration in the food.

Since the compounds of formula (I) according to the invention may be hydrolysed by the constituents of the food, they should be formulated in a protective matrix, e.g., in gelatin, before being added to the premix.

The present invention accordingly relates also to the aspect of controlling parasites by administering to the host animal with its food a compound of formula (I) that has been protected against hydrolysis.

A compound of formula (I) according to the invention is advantageously administered in a dose of from 0.01-800 mg/kg, preferably from 0.1-200 mg/kg, especially from 0.5-30 mg/kg body weight, based on the host animal.

A good dose that can be administered regularly to the host animal is from 0.5-100 mg/kg, preferably from 0.1-40 mg/kg body weight. The administration is effected at suitable intervals in dependence upon the mode of administration and body weight.

The total dose may vary for the same active ingredient from one species of animal to another and also within a species of animal, since it depends inter alia on the weight, age and constitution of the host animal.

When used according to the invention, the compound of formula (I) according to the invention will normally be administered not in pure form but preferably in the form of a composition that comprises, in addition to the active ingredient, constituents that assist administration, suitable constituents being those which are tolerated by the host animal. It is of course possible, as well as controlling the adult parasites in accordance with the invention, additionally to use conventional methods to control the juvenile stages of the fleas, although the latter is not absolutely essential.

Such compositions to be administered in accordance with the invention generally comprise from 0.1-99% by weight, especially from 0.1-95% by weight, of a compound of formula (I) according to the invention and from 99.9-1% by weight, especially from 99.9-5% by weight, of a solid or liquid, physiologically tolerable carrier, including from 0-25% by weight, especially from 0.1-25% by weight, of a non-toxic dispersant.

Whereas commercial products will preferably be formulated as concentrates, the end user will normally employ dilute formulations.

Such formulations may also comprise further ingredients, such as stabilisers, antifoams, viscosity regulators, binders and tackifiers, as well as other active ingredients for obtaining special effects.

The physiologically tolerable carriers known from veterinary medicinal practice for oral, percutaneous and topical administration can be used as formulation adjuvants. Some examples are given below.

Suitable carriers are especially fillers, such as sugars, e.g., lactose, saccharose, mannitol or sorbitol, cellulose preparations and/or calcium phosphates, e.g., tricalcium phosphate or calcium hydrogen phosphate; and binders, such as starch pastes using, e.g., maize, wheat, rice or potato starch, gelatin, tragacanth, methylcellulose and/or, if desired, disintegrators, such as the above-mentioned starches, also carboxymethyl starch, cross-linked polyvinylpyrrolidone, agar, alginic acid or a salt thereof, such as sodium alginate. Adjuvants are especially flow conditioners and lubricants, e.g., silicic acid, talc, stearic acid or salts thereof, such as magnesium or calcium stearate, and/or polyethylene glycol. Dragée cores can be provided with suitable, optionally enteric, coatings, there being used inter alia concentrated sugar solutions which may comprise gum arabic, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropylmethylcellulose phthalate. Dyes, flavorings or pigments may be added to the tablets or dragée coatings, e.g., for identification purposes or to indicate different doses of active ingredient.

Other orally administrable compositions are hard gelatin capsules, and also soft-sealed capsules made of gelatin and a plasticiser, such as glycerol or sorbitol. The hard gelatin capsules may comprise the active ingredient in the form of granules, e.g., in admixture with fillers, such as lactose, binders, such as starches, and/or glidants, such as talc or magnesium stearate, and, optionally, stabilizers. In soft capsules, the active ingredient is preferably dissolved or suspended in suitable liquids, such as fatty oils, paraffin oil or liquid polyethylene glycols, to which stabilizers may also have been added. Preference is given inter alia to capsules that may easily be bitten through or swallowed without being chewed.

The pour-on or spot-on method comprises applying the compound of formula (I) to a locally limited area of the skin or coat, advantageously on the back of the neck or the backbone of the animal. This is carried out, for example, by applying the pour-on or spot-on formulation using a swab or spray to a relatively small area of the coat from where the active ingredient becomes distributed over a wide area of the coat almost automatically as a result of the spreading constituents of the formulation assisted by the movements of the animal.

Pour-on and spot-on formulations advantageously comprise carriers that assist rapid distribution over the surface of the skin and in the coat of the host animal and are generally termed spreading oils. There are suitable, e.g., oily solutions; alcoholic and isopropanolic solutions, e.g., solutions of 2-octyl dodecanol or oleyl alcohol; solutions in esters of monocarboxylic acids, such as isopropyl myristate, isopropyl palmitate, lauric acid oxalic ester, oleic acid oleyl ester, oleic acid decyl ester, hexyl laurate, oleyl oleate, decyl oleate, caproic acid esters of saturated fatty alcohols of chain length $C_{12}$-$C_{18}$; solutions of esters of dicarboxylic acids, such as dibutyl phthalate, diisopropyl isophthalate, adipic acid diisopropyl ester, di-n-butyl adipate or solutions of esters of aliphatic acids, e.g., glycols. It may be advantageous for a dispersant known from the pharmaceutical or cosmetic industry also to be present. Examples are pyrrolidin-2-one, N-alkylpyrrolidin-2-one, acetone, polyethylene glycol and its ethers and esters, propylene glycol or synthetic triglycerides.

The oily solutions include, e.g., vegetable oils, such as olive oil, groundnut oil, sesame oil, pine oil, linseed oil and castor oil. The vegetable oils may also be in epoxidised form. It is also possible to use paraffins and silicone oils.

Generally a pour-on or spot-on formulation will contain from 1-20% by weight of a compound of formula (I), from 0.1-50% by weight dispersant and from 45-98.9% by weight solvent.

The pour-on and spot-on methods can be used especially advantageously for herd animals, such as cattle, horses, sheep and pigs, where it is difficult or time-consuming to treat all the animals orally or via injection. By virtue of its simplicity, this method can of course also be used for all other animals, including individual domestic animals and pets, and is welcomed especially by the keepers of the animals because it can frequently be carried out without the expert assistance of a veterinary surgeon.

Suitable for parenteral and percutaneous administration are oily injection solutions or suspensions, there being used suitable lipophilic solvents or vehicles, such as fatty oils, for example sesame oil, or synthetic fatty acid esters, e.g., ethyl oleate, or triglycerides, or aqueous injection solutions or suspensions that comprise viscosity-increasing substances, e.g., sodium carboxymethylcellulose, sorbitol and/or dextran, and, optionally, stabilizers.

The compositions of the present invention can be prepared in a manner known per se, e.g., by means of conventional mixing, granulating, confectioning, dissolving or lyophilizing processes. For example, pharmaceutical compositions for oral administration can be obtained by combining the active ingredient with solid carriers, optionally granulating a resulting mixture, and processing the mixture or granules, if desired or necessary, after the addition of suitable excipients, to form tablets or dragée cores.

The following Examples and patent claims illustrate the invention described above, but do not limit its scope in any way. Temperatures are given in degrees Celsius. In the following Formulation Examples the expression "compound of formula (I)" is used to represent a compound of Tables 1-3, especially benzoic acid({1-[(6-chloro-pyridin-3-ylmethyl)-ethyl-amino]-2-nitro-vinyl}-methyl-carbamoyloxy)-methyl ester.

FORMULATION EXAMPLES

Example 1

Tablets Comprising 25 mg of a Compound of Formula (I) can be Prepared as Follows

| Constituents (for 1000 tablets) | |
|---|---|
| compound of formula (I) | 25.0 g |
| lactose | 100.7 g |
| wheat starch | 7.5 g |

-continued

| Constituents (for 1000 tablets) | |
|---|---|
| polyethylene glycol 6000 | 5.0 g |
| talcum | 5.0 g |
| magnesium stearate | 1.8 g |
| demineralized water | q.s. |

Preparation: All the solid ingredients are first forced through a sieve of 0.6 mM mesh size. Then the active ingredient, the lactose, the talcum and half the starch are mixed together. The other half of the starch is suspended in 40 mL of water and the suspension is added to a boiling solution of the polyethylene glycol in 100 mL of water. The resulting starch paste is added to the main batch and the mixture is granulated, if necessary with the addition of water. The granules are dried overnight at 35° C., forced through a sieve of 1.2 mM mesh size, mixed with the magnesium stearate and compressed to form tablets which have a mesh size of about 6 mM and which are concave on both sides.

Example 2

Injection Solution

| compound of formula (I) | 0.1-10%, preferably 0.5-5% |
|---|---|
| non-ionic surfactant | 0.1-30%, preferably 0.5-10% |
| mixture of ethanol and propylene glycol | 60-99%, preferably 85-90% |

Example 3

Injection Suspension (Aqueous or Oily)

| compound of formula (I) | 0.1-20%, preferably 1-10% |
|---|---|
| non-ionic surfactant | 0.1-20%, preferably 1-10% |
| water or vegetable oil | 60-99%, preferably 85-95% |

Example 4

Oily Injectable

| Oily vehicle (slow release) | | |
|---|---|---|
| A. | compound of formula (I) groundnut oil | 0.1-1.0 g ad 100 mL |
| or | | |
| B. | compound of formula (I) sesame oil | 0.1-1.0 g ad 100 mL |

Preparation: The active ingredient is dissolved in a portion of the oil, with stirring and optionally with gentle heating, and after cooling the solution is made up to the desired volume and sterile-filtered through a suitable 0.22 mM membrane filter.

Example 5

Pour-on

| A. | compound of formula (I) | 10% |
|---|---|---|
| | epoxidized soybean oil | 5% |
| | oleyl alcohol | 85% |
| B. | compound of formula (I) | 20% |
| | pyrrolidin-2-one | 15% |
| | isopropyl myristate | 65% |

It is also possible to add to the described compositions biologically active substances or additives that have neutral behaviour towards the compounds of formula (I) and have no adverse effect on the host animal to be treated, and also mineral salts or vitamins.

Analogously to the described formulations of Examples 1-8 it is also possible to prepare further preparations having active ingredients of formula (I).

Example 6

Control of Adult Fleas in Cats by Means of Pour-on Application Test Protocol for Each Test Compound In order to determine the effectiveness of the test compounds against fully grown fleas, four groups each of two cats are used. Each cat is infested with 100 cat fleas [*Ctenocephalides felis* (Bouche)] and treated with 20 mg of active ingredient per kg body weight. The treatment is effected by applying the formulation to a locally limited area on the back of the cat's neck. While one group is infested with fleas but is treated only with a placebo, that is to say a formulation without active ingredient, and serves as control, another group is treated with nitenpyram as comparison substance; the two remaining groups receive the test compounds. Evaluation is made in each case by combing surviving fleas out of the animal's coat and comparing the number counted with the number of fleas in the control group and in the group treated with nitenpyram.

The procedure in detail is as follows: each cat is infested with 100 fleas immediately after treatment on day 0. On day +1, each animal is combed and the number of surviving fleas is determined; the surviving fleas are then replaced on the same cat and after 24 hours the combing and evaluation are repeated. The fleas still surviving after those 24 hours are not returned to the cat. The described procedure is then repeated on days +3, +7, +9, +14, +21, +28, +35, +42, +49, +56 and +63 and in this way the effectiveness and duration of action are determined. The effectiveness is determined in accordance with the following formula:

$$\% \text{ effectiveness} = \frac{\text{number of living fleas on the control animal} \text{ minus } \text{number of living fleas on the test animal}}{\text{number of living fleas on the control animal}} \times 100$$

It is shown that the compounds of formula (I) according to the invention achieve excellent long-term action. Very good action is obtained, e.g., with Compound Nos. 1.001, 1.008, 1.011, 1.012, 1.013, 1.014, 1.015, 1.018, 1.020, 1.021 and 1.022. An especially high level of long-term activity is exhibited by Compound Nos. 1.008, 1.011 and 1.012. Full action (100% effectiveness) is observed over a period of at least 7 weeks and after 7 weeks the action gradually declines to 26%. In comparison, nitenpyram exhibits full action (100% effectiveness) only for a maximum of 3 weeks. In a further, fully analogous test, Compound Nos. 1.019, 1.056, 1.057 and 1.058 also exhibit a long-term action equally as excellent as the compounds mentioned above.

In dogs the test proceeds in an entirely analogous manner. In order to investigate the total action and any side-effects after administration in the form of a pour-on formulation, Compound No. 1.008 is selected and tested on 11 dogs. The test protocol and the results are given in Example 7.

Example 7

Control of Adult Fleas in Dogs by Means of Pour-on Application with Compound No. 1.008 of Table 1

Test protocol for each test compound: in order to determine the effectiveness of the test compounds against fully grown fleas, three groups each of three dogs (1 male and 2 female beagles) are used; one group consists of two dogs (2 male beagles) and serves as control group. The entire test group consists of 11 beagles between 1 and 3.5 years of age. Each dog is infested with a total of 100 dog fleas [*Ctenocephalides canis*], 50 male and 50 female. Group 1 is treated with 2 mg, group 2 with 10 mg and group 3 with 20 mg of active ingredient per kg body weight. The treatment is effected by applying the pour-on formulation to a locally limited area on the back of the dog's neck. The fourth group is the control group. The latter is infested with fleas but is treated only with a placebo, that is to say a formulation without active ingredient, and serves for control purposes. Evaluation is made in each case by combing surviving fleas out of the animal's coat and comparing the number counted with the number of fleas in the control group. The procedure in detail is as follows: after treatment with the test formulation (day 0) each dog is infested on each of the subsequent days +1, +7, +14, +23, +28, +35, +49, +56, +63, +70, +77, +84 and +98 with 100 fleas. On the following day, each animal is combed and the number of surviving fleas is determined. The surviving fleas are then replaced on the same dog and after 24 hours the combing and evaluation are repeated. The fleas still surviving after those further 24 hours ($2^{nd}$ day after infestation with 100 fleas) are not returned to the dog. Then on days +3, +7, +9, +14, +21, +28, +35, +42 etc. the described procedure is repeated and in this way the effectiveness and the duration of action are determined. The effectiveness is determined using the formula given in Example 6.

Seventy-nine days after application of the pour-on formulation, the test compound exhibits 100% action; it is still 98.6% effective on day 86 and even on day 98 it continues to be 92.3% effective. Whereas the dogs from the three test groups exhibit no skin irritation or any other undesirable side effects, the two dogs in the control group have to be removed from the test program on day 84, because they exhibit serious allergy symptoms and skin irritation as a result of the numerous flea bites.

Corresponding effects are also observed when the substances are administered not in pour-on form but in the form of an injection solution.

Example 8

Control of Adult Fleas in Cats by Means of Subcutaneous Injection

Test protocol for each test compound: in order to determine the effectiveness of the test compounds against fully grown fleas, four groups each of two cats from 1.5-4 years of age are used. Each cat is infested with 100 cat fleas [*Ctenocephalides felis* (Bouche)]. Two groups are treated with 20 mg of active ingredient per kg body weight. The treatment is effected by subcutaneous injection of a solution of the active ingredient behind the left shoulder blade. While one group is infested with fleas but is treated only with a placebo, that is to say a formulation without active ingredient, and serves as control, another group is treated with nitenpyram as comparison substance. Evaluation is made in each case by combing surviving fleas out of the animal's coat and comparing the number counted with the number of fleas in the control group and in the group treated with nitenpyram. The procedure in detail is as follows: each cat is infested with 100 fleas immediately after treatment on day 0. On day +1, each animal is combed and the number of surviving fleas is determined; the surviving fleas are then replaced on the same cat and after 24 hours the combing and evaluation are repeated. The fleas still surviving after those 24 hours are not returned to the cat. The described procedure is then repeated on days +3, +7, +9, +14, +21 and +28 and in this way the effectiveness and duration of action is determined. The effectiveness is determined using the same formula as in the preceding Example.

It is found that the compounds of formula (I) according to the invention achieve excellent long-term action after subcutaneous injection. Very good action is achieved, e.g., with Compound Nos. 1.001, 1.008, 1.011, 1.012, 1.013, 1.014, 1.015, 1.018, 1.020, 1.021 and 1.022. An especially high level of long-term activity is exhibited by Compound No. 1.012.

Full action is observed for a period of at least 20 days in comparison with 2 days in the case of nitenpyram. The analogous test with dogs leads to absolutely comparable results.

Compound Nos. 1.059-1.087 also exhibit very similar results to those described in Examples 6-8.

What is claimed is:

1. A compound of formula (I)

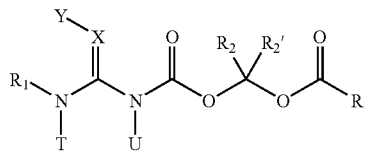

wherein
$R_1$ thiazolyl-substituted $C_1$-$C_6$alkyl, wherein the thiazolyl moiety is unsubstituted or mono- or poly-substituted by identical or different halogen atoms;
X is CH;
Y is $NO_2$;
T is hydrogen or $C_1$-$C_6$alkyl;
U is hydrogen or $C_1$-$C_6$alkyl;
$R_2$ is hydrogen or $C_1$-$C_6$alkyl;
$R_{2'}$ is hydrogen or $C_1$-$C_6$alkyl; and
R is $C_1$-$C_{20}$alkyl, being unsubstituted or substituted by one or more identical or different substituents, the said substituents being selected from the group halogen, cyano, nitro, hydroxy, $C_1$-$C_6$alkoxy, $C_1$-$C_6$alkylthio, $C_1$-$C_6$haloalkyl, $C_1$-$C_6$haloalkoxy and phenyl.

2. A compound according to claim 1, which is a compound of formula (X)

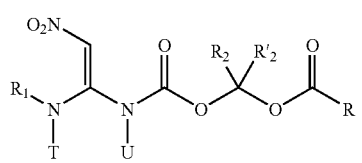

wherein
$R_1$ is —$CH_2$-thiazolyl, which is unsubstituted or mono- or poly-substituted by identical or different halogen atoms;
R is $C_1$-$C_{20}$alkyl, being unsubstituted or mono- or poly-substituted by identical or different substituents, the said substituents being selected from the group halogen, cyano, nitro, hydroxy, $C_1$-$C_6$alkoxy, $C_1$-$C_6$alkylthio, $C_1$-$C_6$haloalkyl, $C_1$-$C_6$haloalkoxy and phenyl;

T and U are each independently of the other hydrogen, methyl or ethyl;
$R_2$ is hydrogen or $C_1$-$C_6$alkyl; and
$R_{2'}$ is hydrogen or $C_1$-$C_6$alkyl.

3. A compound of formula (I) according to claim 1, wherein U is methyl or ethyl.

4. A compound of formula (I) according to claim 1, wherein T is methyl or ethyl.

5. A compound of formula (I) according to claim 1, wherein $R_2$, $R_{2'}$ are each independently of the other hydrogen, methyl, or ethyl.

6. A compound of formula (I) according to claim 1, wherein $R_1$ is —$CH_2$— thiazolyl, that is unsubstituted or mono- or di-substituted by halogen.

7. A compound of formula (I) according to claim 6, wherein thiazolyl in $R_1$ is 2-chlorothiazol-5-yl.

8. A compound according to claim 1, wherein R is straight-chain or branched $C_6$-$C_{20}$alkyl.

9. A preparation for controlling parasites on warm-blooded animals, comprising a compound according to claim 1, one further parasiticide, and a physiologically tolerable carrier.

10. A parasiticidal composition comprising a compound of formula (I) according to claim 1 and at least one physiologically tolerable carrier.

11. A parasiticidal composition according to claim 10, comprising from 0.1 to 99% by weight of a compound of formula (I) according to claim 1 and from 99.9 to 1% by weight of a solid or liquid, physiologically tolerable carrier, including from 0 to 25% by weight of a non-toxic dispersant.

12. A parasiticidal composition according to claim 11, which is a pour-on or spot-on formulation.

13. A method of controlling parasites on warm-blooded animals, which comprises administering to a warm blooded animal a parasiticidally effective compound of formula (I) according to claim 1.

14. A method according to claim 13 comprising the topical application of a compound of formula (I) according to claim 1.

15. A method according to claim 13, wherein a compound of formula (I) according to claim 1 is administered in a dose of from 0.01 to 800 mg/kg/body weight.

16. A veterinary medicinal preparation against parasites comprising a compound of claim 1 and a physiologically acceptable carrier.

* * * * *